(12) United States Patent
Purcell et al.

(10) Patent No.: US 9,117,140 B2
(45) Date of Patent: Aug. 25, 2015

(54) SYSTEM AND METHOD OF IN-SEASON NITROGEN MEASUREMENT AND FERTILIZATION OF NON-LEGUMINOUS CROPS FROM DIGITAL IMAGE ANALYSIS

(71) Applicant: Board of Trustees of the University of Arkansas, Little Rock, AR (US)

(72) Inventors: Larry C. Purcell, Fayetteville, AR (US); Upton G. Siddons, Little Rock, AR (US); Douglas E. Karcher, Fayetteville, AR (US); Robert L. Rorie, South Fulton, TN (US)

(73) Assignee: Board of Trustees of the University of Arkansas, Little Rock, AR (US)

( * ) Notice: Subject to any disclaimer, the term of this patent is extended or adjusted under 35 U.S.C. 154(b) by 211 days.

(21) Appl. No.: 13/652,605

(22) Filed: Oct. 16, 2012

(65) Prior Publication Data
US 2013/0044919 A1      Feb. 21, 2013

Related U.S. Application Data

(63) Continuation-in-part of application No. 12/800,849, filed on May 24, 2010, now Pat. No. 8,391,565.

(51) Int. Cl.
| | |
|---|---|
| *G06K 9/00* | (2006.01) |
| *G06K 9/46* | (2006.01) |
| *G01N 21/25* | (2006.01) |
| *G01N 21/84* | (2006.01) |

(Continued)

(52) U.S. Cl.
CPC .............. *G06K 9/4652* (2013.01); *G01N 21/25* (2013.01); *G01N 21/84* (2013.01); *G06T 7/0012* (2013.01); *G06T 7/408* (2013.01); *G01N 2021/8466* (2013.01); *G06T 2207/10024* (2013.01); *G06T 2207/30128* (2013.01)

(58) Field of Classification Search
None
See application file for complete search history.

(56) References Cited

U.S. PATENT DOCUMENTS

| | | | |
|---|---|---|---|
| 5,606,821 | A | 3/1997 | Sadjadi et al. |
| 6,160,902 | A | 12/2000 | Dickson et al. |

(Continued)

OTHER PUBLICATIONS

Choi et al ("Color Correction for Object Identification from Images with Different Colo Illumination", Seol University, Korea, 2009).*

(Continued)

*Primary Examiner* — Shervin Nakhjavan
(74) *Attorney, Agent, or Firm* — Head, Johnson & Kachigian, P.C.

(57) ABSTRACT

Systems and methods of determining nitrogen levels from a digital image and in-season nitrogen measurement and fertilization of non-leguminous crops from digital image analysis are disclosed herein. In particular, a method of determining leaf nitrogen concentration and yield from a digital photograph of a fully developed leaf (collared leaf) of a crop of non-legumes, such as corn, wheat, rice, cotton, potatoes sugarcane, turfgrass or forage grass species. The digital image is processed to determine a dark green color index ("DGCI"), which is closely related to leaf nitrogen concentration and yield. Standardized color disks having known DGCI values are included in the digital photograph and serve as an comparative standard. The comparative standard allows correction of DGCI of samples when using different cameras and/or when lighting conditions change. The DGCI values can then be used to determine the amount of nitrogen fertilizer that should be applied to recover crop yield potential.

46 Claims, 32 Drawing Sheets

(51) Int. Cl.
*G06T 7/00* (2006.01)
*G06T 7/40* (2006.01)

(56) References Cited

U.S. PATENT DOCUMENTS

| | | | |
|---|---|---|---|
| 6,466,321 | B1 | 10/2002 | Satake et al. |
| 6,529,615 | B2 | 3/2003 | Hendrickson et al. |
| 6,567,537 | B1 | 5/2003 | Anderson |
| 6,683,970 | B1 | 1/2004 | Satake et al. |
| 6,734,973 | B1 | 5/2004 | Mutters et al. |
| 6,792,882 | B2 | 9/2004 | Aspelin et al. |
| 6,813,544 | B2 | 11/2004 | Hood et al. |
| 7,068,816 | B1* | 6/2006 | Knoblauch et al. ........... 382/110 |
| 7,103,451 | B2 | 9/2006 | Seal et al. |
| 7,184,859 | B2 | 2/2007 | Hood et al. |
| 7,362,439 | B2 | 4/2008 | Franzen et al. |
| 7,408,145 | B2 | 8/2008 | Holland |
| 7,723,660 | B2 | 5/2010 | Holland |
| 7,929,141 | B2 | 4/2011 | Franzen et al. |
| 8,208,680 | B2 | 6/2012 | Scharf et al. |
| 2001/0016053 | A1* | 8/2001 | Dickson et al. ............... 382/110 |
| 2001/0036295 | A1* | 11/2001 | Hendrickson et al. ........ 382/110 |
| 2004/0032973 | A1 | 2/2004 | Robeson et al. |
| 2005/0150160 | A1* | 7/2005 | Norgaard et al. ......... 47/58.1 SE |
| 2005/0241285 | A1* | 11/2005 | Maertens et al. .................... 56/1 |
| 2006/0039603 | A1 | 2/2006 | Koutsky |
| 2007/0014434 | A1* | 1/2007 | Wei et al. ...................... 382/104 |
| 2008/0304711 | A1* | 12/2008 | Scharf et al. .................. 382/110 |
| 2009/0164281 | A1* | 6/2009 | Norgaard et al. ................. 705/7 |
| 2009/0220645 | A1* | 9/2009 | Martinez et al. ................ 426/45 |
| 2011/0047867 | A1 | 3/2011 | Holland |
| 2012/0250962 | A1 | 10/2012 | Scharf et al. |

OTHER PUBLICATIONS

Walsh ("Effect of Delayed Nitrogen Fertilization on Corn Grain Yields",Thesis submitted to the Faculty of the Graduate College of the Oklahoma State University in partial fulfillment of the requirements for the Degree of Master of Science Dec. 2006).*

Karcher, Douglas E., Quantifying Turfgrass Color Using Digital Image Analysis, Crop Science, vol. 43: 943-951; May-Jun. 2003. Dept. of Horiculture, Univ. of Arkansas; U.S.

Murakami, Paula F., An Instructional Guide for Leaf Color Analysis using Digital Imaging Software, Forest Service, Northeastern Research Station, General Technical Report NE-327; May 2005. USDA Forest Service Publications Distribution. U.S.

Yaju, Liu, et al., A Research in the Application of Computer-Vision to Plant Growth Monitoring Oct. 2007; pp. 522-526; School of Mechanical and Electrical Engineering, Hebei Agricultural University;Hebei, China.

Patton, Aaron, et. al., Using Digital Image Analysis to Quantify Turfgrass Cover and Disease. Nov. 2009; U.S.

Kyveryga, P.M., Using Late-Season Uncalibrated Digital Aerial Imagery for Predicting Corn Nitrogen Status within Fields; Jul. 2010; Laboratory for Applied Spatial Analysis, Southern Illinois University, Edwardsville, Illinois; U.S.

Peter C. Scharf et al. Calibrating Reflectance Measurements to Predict Optimal Sidedress Nitrogen Rate for Corn, Agronomy Journal, 2009, vol. 101, Issue 3, Columbia, Missouri.

Peter C. Scharf et al. Chlorophyll Meter Readings Can Predict Nitrogen Need and Yield Response of Corn in the North-Central USA, Reproduced from Agronomy Journal, 2006, Columbia, Missouri.

Simone Graeff et al. Quantifying Nitrogen Status of Corn (*Zea mays* L.) in the Field by Reflectance Measurements, European Journal of Agronomy, 2003, Stuttgart, Germany.

Schepers, J. S., D.D. Francis, M. Vigil, and F. E. Below. 1992. Comparison of corn leaf nitrogen concentration and CM readings. Commun. Soil Sci. Plant Anal. 23:2173-2187. SPAD Patent? U.S. Appl. No. 60/738,752.

Siddons, U.G., L.C. Purcell, M. Mozaffari. In-season corn nitrogen measurement and fertilization via image analysis. ASA-CSSA-SSSA Annual Meeting. San Antonio, TX. Oct. 17, 2011.

Siddons, U.G., L.C. Purcell, M. Mozaffari. Dark green color index as a method of real-time, in-season corn nitrogen measurement and fertilization. ASA-CSSA-SSSA Annual Meeting. San Antonio, TX. Oct. 17, 2011.

Rorie, R.L, L.C. Purcell, M. Mozaffari, D.E. Karcher, C.A. King, M.C. Marsh, and D.E. Longer. 2011. Association of "greenness" in corn with yield and leaf nitrogen concentration. Agron. J. 103:529-535.

Rorie, R.L, L.C. Purcell, D.E. Karcher, C.A. King. 2011. The assessment of leaf nitrogen in corn from digital images. Crop Sci. 51:2174-2180.

Raper, T.B., D.M. Oosterhuis, U. Siddons, L.C. Purcell, and M. Mozaffari. 2012. Effectiveness of the dark green color index in determining cotton nitrogen status from multiple camera angles. Int. J. Appl. Sci. Tech. 2:71-74.

* cited by examiner

SYSTEM AND METHOD OF IN-SEASON NITROGEN MEASUREMENT AND FERTILIZATION OF NON-LEGUMINOUS CROPS FROM DIGITAL IMAGE ANALYSIS

CROSS REFERENCE TO RELATED APPLICATIONS

This application is a continuation-in-part of and claims priority to U.S. patent application Ser. No. 12/800,849, entitled "System and Method of Determining Nitrogen Levels from a Digital Image," filed May 24, 2010, which is incorporated herein by reference in its entirety.

STATEMENT REGARDING FEDERALLY SPONSORED RESEARCH OR DEVELOPMENT

Not Applicable.

NAMES OF THE PARTIES TO A JOINT RESEARCH AGREEMENT

Not Applicable.

REFERENCE TO A SEQUENCE LISTING, A TABLE, OR A COMPUTER PROGRAM LISTING APPENDIX

Not Applicable.

BACKGROUND OF THE INVENTION

1. Field of the Invention

This invention relates generally to a system and method of in-season nitrogen measurement and fertilization of non-leguminous crops from digital image analysis, and more particularly to a system and method of measuring leaf nitrogen concentration using dark green color index values from a digital image of a non-legume crop and determining the amount of in-season nitrogen fertilization to be applied to maximize crop yield potential.

2. Description of the Related Art

Management of fertilizer nitrogen is a critical component for producing consistent crop yields. Nitrogen fertilizer also represents a considerable input cost and has serious environmental consequences if over applied. The prevalence of nitrogen in the cells of agronomic crops means that harvest removes large quantities of nitrogen from a field, and, in doing so, creates of a paucity of the nutrient residual in the soil for future production. This, coupled with nitrogen loss from soils by leaching, volatilization and denitrification, establishes a situation in which nitrogen is the nutritional factor most commonly limiting crop yield potential. To remedy this, plant-available nitrogen forms are provided to the crop in the form of chemical fertilizers, such as anhydrous ammonia and urea. Synthetic nitrogen fertilization is a cornerstone of modern agriculture because it provides the nutrients needed for elevated grain yield and quality. Therefore, it is important to apply the correct amount of fertilizer to meet the crop's need but not to supply more than is required because of the cost and environmental concerns.

The diagnosis of in-season nitrogen deficiencies must be followed by corrective nitrogen applications to recover potential yield. A key to corrective nitrogen fertilization action is up-to-date knowledge of advent and degree of nitrogen deficiency. Immediate knowledge of plant nitrogen concentration is often not obtainable due to a lag time for processing. This lag time can negatively affect the value of the derived information due to the short window during which nitrogen demand is increasing and deficiencies can be most effectively corrected. Nitrogen requirements of the crop increase dramatically beginning with the V6 development stage, and the final chance for practical application of non-foliar nitrogen fertilization (due to increasing plant height) occurs about a week later at the V8 stage. The V8 development stage is also the final point at which corrective applications can re-establish near complete yield potential.

In addition to timing, spatial variability exists within any field relative to the amount of nitrogen required by a particular crop. An attempt to reduce nitrogen fertilizer losses must take this into account. A field-wide map for variable-rate nitrogen application can be achieved several ways, but must have as high a level of accuracy and resolution as possible to maximize fertilizer efficiency.

There are few tools that are currently available to help farmers determine if crop nitrogen levels during the season are adequate, and several techniques have been used to objectively measure crop color, including reflectance measurements, chlorophyll and amino acid analysis, and comparison with standardized colors. All of these techniques have certain disadvantages compared with subjective color ratings. Reflectance, chlorophyll, and amino acid measurements all require relatively expensive equipment, and transport of samples to a laboratory for analysis. Shipping these measurements to a qualified testing service can compromise the brief window in which the information might be of value. In addition, correlations between color and chlorophyll or amino acid measurements are either species or cultivar dependent. A hand-held SPAD meter (Minolta) gives real-time chlorophyll concentration of leaves in the field, and chlorophyll concentration has a close relationship to leaf nitrogen concentration. Disadvantages of the SPAD meter include a large initial equipment cost and that a large number of measurements may be required to make a representative measurement.

Digital image analysis is an emerging method of nitrogen status diagnosis that addresses the needs of time, cost, and data resolution. Through digital photography, farmers can instantaneously obtain millions of bits of information on a relatively large crop canopy. For example, a digital image taken of a crop using a 1280×960 pixel resolution contains 1,228,800 pixels, with each pixel containing independent color information about the crop.

The information contained in each digital image includes the amount of red, green and blue ("RGB") light emitted for each pixel in the digital image. Although it may be intuitive to use the green levels of the RGB information to quantify the green color of the digital image, the intensity of red and blue will confound how green the digital image appears. To ease the interpretation of digital color data, RGB values can be converted directly to hue, saturation and brightness ("HSB") values that are based on human perception of color. In HSB color description, hue is defined as an angle on a continuous circular scale from 0° to 360° (0°=red, 60°=yellow, 120°=green, 180°=cyan, 240°=blue, 300°=magenta), saturation is the purity of the color from 0% (gray) to 100% (fully saturated color), and brightness is the relative lightness or darkness of the color from 0% (black) to 100% (white).

It is therefore desirable to provide a system and method of determining nitrogen levels from a digital image and in-season nitrogen measurement and fertilization of non-leguminous crops from digital image analysis that does not require specialized, expensive equipment.

It is further desirable to provide the systems and methods disclosed herein that can easily be sent electronically, such as via email or to a web-based server, for immediate analysis.

It is still further desirable to the systems and methods disclosed herein that integrate values over a much larger leaf sample than does the SPAD meter.

It is yet further desirable to provide the systems and methods disclosed herein that do not rely on chemical processes of measuring leaf nitrogen.

It is yet further desirable to provide the systems and methods disclosed herein having quick turn-around times to provide farmers with real-time nitrogen concentration and yield information for the crop.

It is still yet further desirable to provide the systems and methods disclosed herein that provide early, precise and accurate measurements of current nitrogen status crucial for maintaining high nitrogen use efficiencies in the crop.

It is still yet further desirable to provide the systems and methods disclosed herein that provide favorable nutrient conditions for maximizing potential yield of the crop.

It is still further desirable to provide the systems and methods disclosed herein that employ DGCI as a means of correcting nitrogen deficiencies in the crop at specific development stages.

It is yet further desirable to provide the systems and methods disclosed herein that improve nitrogen-use efficiency, thereby benefiting farmers, crop producers and consumers with lower costs of production, less environmental pollutants, and greater energy efficiency.

BRIEF SUMMARY OF THE INVENTION

In general, in a first aspect, the invention relates to a computer-implemented method of determining an in-season nitrogen fertilization rate for a non-legume crop using digital image analysis. The method includes receiving a dark green color index obtained from analysis of a digital image of the crop. The image includes a comparative standard to account for differences in cameras or lighting conditions or both. The method also includes determining the nitrogen fertilization rate from the dark green color index to achieve a predetermined yield potential for the crop.

The method can also include acquiring the digital image of a colored leaf from the crop of non-legume plants. The image includes the comparative standard and may also include a contrasting standard having a color in a portion of the visible spectrum away from the visible spectrum of the color of the leaf. The method can then perform an algorithm to determine the dark green color index of the leaf in the image.

The comparative standard may include standardized color disks having a predetermined shape and a color representing a color value ranging from severely nitrogen deficient to nitrogen sufficient of the leaf, such as a first standardized color disk having a yellow color representing a severely nitrogen deficient leaf and a second standardized disk having a dark green color representing a nitrogen sufficient leaf against a pink background. The method may include placing the standardized color disks a distance away from the leaf during the digital photography to minimize any shadows between the leaf and the standardized color disks. In addition, the algorithm recognizes the shape of the standardized color disks and uses the standardized color disks as the comparative standard to adjust for different cameras and/or lighting conditions.

The algorithm of the method can further include the steps of calculating a dark green color index of the leaf in the digital image, calculating a dark green color index of the standardized color disks in the image, and calculating a corrected leaf dark green color index from the dark green color index of the leaf and the dark green color index of the standardized color disks. The step of calculating the dark green color index of the leaf in the image may include obtaining absolute red, green and blue values of the leaf in the image, converting the absolute red, green and blue values to percentage red, green and blue values of the leaf in the image, converting the percentage red, green and blue values to absolute hue, saturation and brightness values of the leaf in the image, calculating average hue, saturation and brightness values from the absolute hue, saturation and brightness values of the leaf in the image, and converting the average hue, saturation and brightness values to the dark green color index of the leaf in the image. Similarly, the step of calculating a dark green color index of the standardized color disks may include obtaining absolute red, green and blue values of the standardized color disks in the image, converting the absolute red, green and blue values to percentage red, green and blue values of the standardized color disks in the image, converting the percentage red, green and blue values to absolute hue, saturation and brightness values of the standardized color disks in the image, calculating average hue, saturation and brightness values from the absolute hue, saturation and brightness values of the standardized color disks in the image, and converting the average hue, saturation and brightness values to the dark green color index of the standardized color disks in the image.

The average hue, saturation and brightness values can be converted to the dark green color index of the leaf in the image using $DGCI=[(H-60)/60+(1-S)+(1-B)]/3$, where DGCI is equal to dark green color index of the leaf, H is equal to the average hue value, S is equal to the average saturation value, and B is equal to the average brightness value. The dark green color index of the leaf and/or the standardized color disks in the image encompasses a dark green color on a scale of zero (0) to one (1) with values closer to one (1) representing a darker green.

Moreover, the method may also include the steps of determining yield of the crop from the image as a function of the corrected dark green color index and further transmitting the yield of the crop. Additionally, the method may include estimating yield of the crop from the image based on the leaf nitrogen sufficiency or deficiency, such as corn when measured at tasseling, and/or transmitting the leaf nitrogen sufficiency or deficiency.

The nitrogen fertilization rate can be a recommended amount of nitrogen per unit area to be applied at in-season in order to maximize the predetermined yield potential for the crop, such as corn at V6 through V10 development stage. The nitrogen fertilization rate can be provided using a quadratic mathematical model forming a yield potential response curve as a function the nitrogen fertilization rate. The quadratic mathematical model is a function of $f(x)=ax^2+bx+c$, and the nitrogen fertilization rate at which yield is maximized is equal to $-b/2a$.

In general, in a second aspect, the invention relates to a computer system programmed to determine an in-season nitrogen fertilization rate for a non-legume crop using digital image analysis. The system can include at least one electronic device for taking the digital image of the crop of the non-legume plant. The electronic device can be programed with an application program. A central processing unit can be communicably attached to the electronic device via a network connection for performing an algorithm to estimate the nitrogen fertilization rate based on the dark green color index.

In addition, the comparative standard may be standardized color disks having a predetermined shape and a color representing a color value ranging from severely nitrogen deficient to nitrogen sufficient of the leaf, such as a first standardized color disk having a yellow color representing a severely nitrogen deficient leaf and a second standardized disk having a dark green color representing a nitrogen sufficient leaf.

Furthermore, the non-legume plant may be corn, rice, wheat, cotton, potatoes, sugarcane, turfgrass or forage grass species.

Other advantages and features will be apparent from the following description and from the claims.

DETAILED DESCRIPTION OF THE INVENTION

The systems and methods discussed herein are merely illustrative of specific manners in which to make and use this invention and are not to be interpreted as limiting in scope.

While the systems and methods have been described with a certain degree of particularity, it is to be noted that many modifications may be made in the details of the construction and the arrangement of the devices, components and/or steps without departing from the spirit and scope of this disclosure. It is understood that the systems and methods are not limited to the embodiments set forth herein for purposes of exemplification.

A system and method of determining nitrogen levels in non-legume crops from a digital image is an aspect of the invention provided herein. A system and method of in-season nitrogen measurement and fertilization of non-leguminous crops from digital image analysis is another aspect of the invention provided herein. The systems and methods can determine the amount of in-season nitrogen fertilization to be applied to maximize crop yield potential.

Figure 1B:
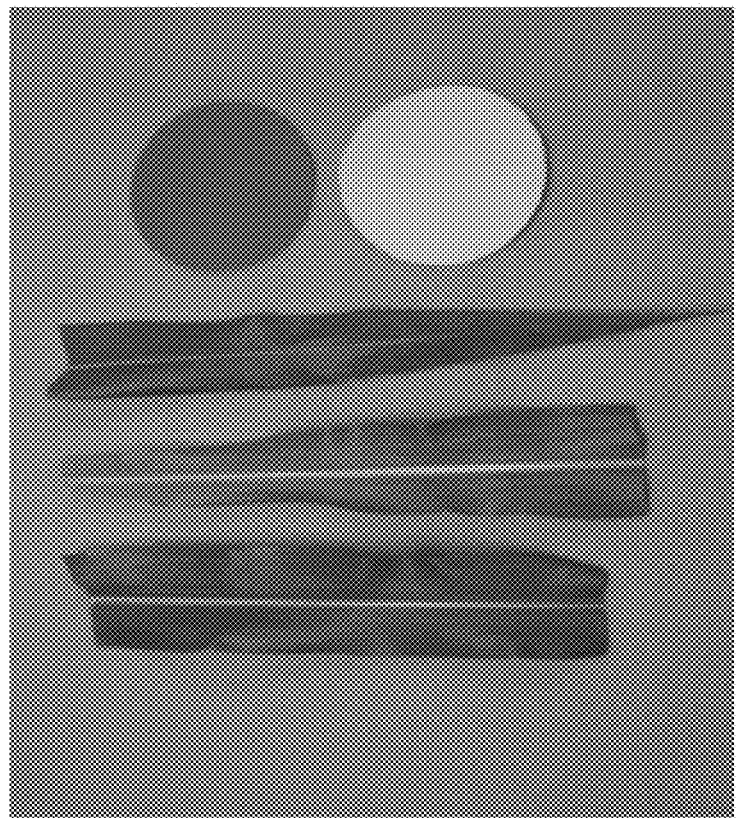
FIGS. 1A and 1B are digital images of uppermost collared corn leaves and standardized color disks against a black felt background (FIG. 1A) and a pink felt background (FIG. 1B) under normal fluorescent lighting in accordance with an illustrative embodiment of the systems and methods disclosed herein.
Figures 2A, 2B:
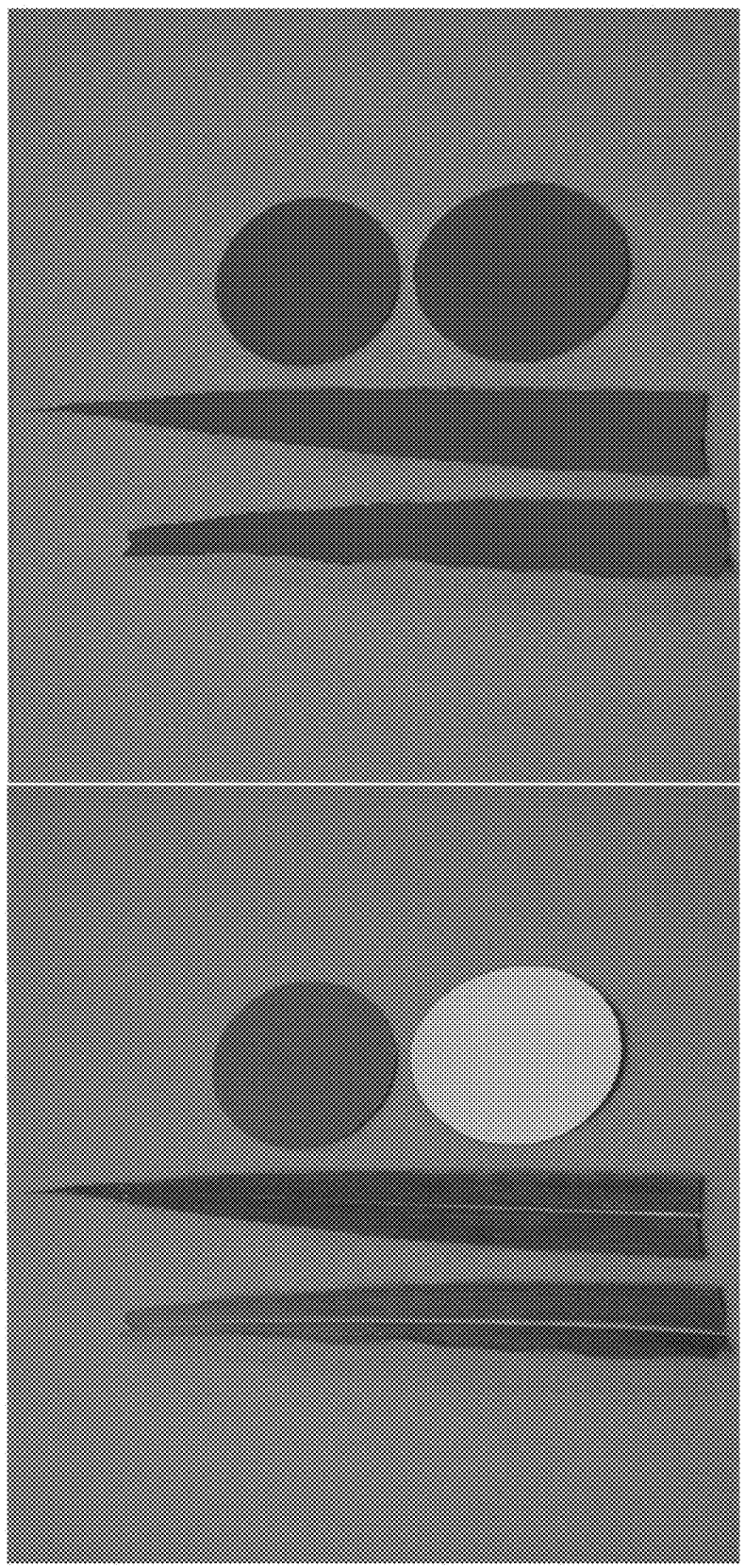
FIGS. 2A and 2B are digital images of uppermost collared corn leaves and standardized color disks before (FIG. 2A) and after (FIG. 2B) analysis using SigmaScan in accordance with an illustrative embodiment of the systems and methods herein.
Figure 9:
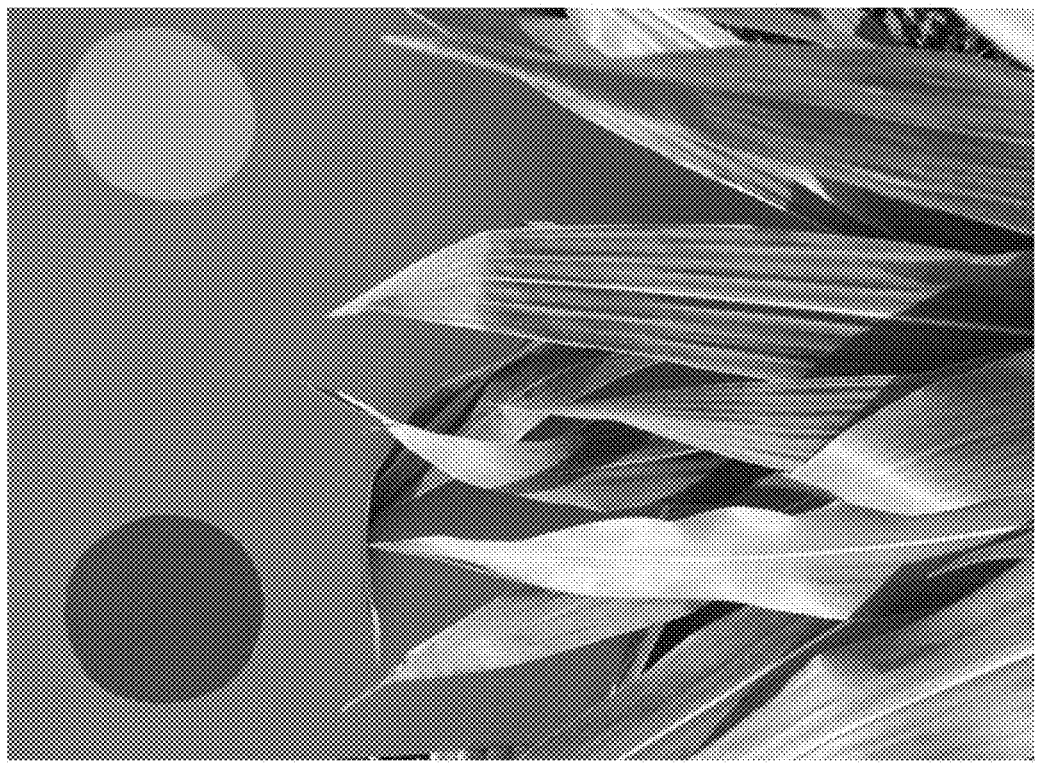
FIG. 9 is a digital image of uppermost collared corn leaves and standardized color disks against a pink background under natural outdoor lighting conditions in a field located in the state of Arkansas in accordance with an illustrative embodiment of the systems and methods disclosed herein.

As shown in FIGS. 1B, 2A and 9, the leaf nitrogen sufficiency or deficiency and yield can be determined from a digital image of a leaf of a non-legume crop, such as corn, rice, wheat, cotton, potatoes, sugarcane or turfgrass, with a contrasting standard. The contrasting standard can be a background, border or other portion of the digital image colored in a portion of the visible spectrum furthest away from the green spectrum, in order to eliminate interference from reflection and other non-target sources. In addition to the leaf, a comparative standard is included in each digital image to account for differences in cameras and/or lighting conditions. The comparative standard serves as an internal standard and may include a plurality of standardized color disks representing the range of green values typically found in the crop, ranging from severely nitrogen deficient to nitrogen sufficient. For example, the digital images of FIGS. 1B, 2A and 9 include uppermost, fully developed leaves and standardized color disks having green colors typically found in corn ranging from severely nitrogen deficient (yellow) to nitrogen sufficient (dark green) placed against a pink background. The standardized color disks should be placed a distance away from any leaf during photography to minimize any shadows between the leaf and the standardized color disks.

An algorithm of the systems and methods recognizes the standardized color disks by their shape and uses them as the comparative standard to adjust for different cameras and/or lighting conditions. The algorithm also converts the RGB spectra of the digital image to values of HSB, which are then converted to a DGCI value. The DGCI is a single value between zero (0) and one (1) and represents the "greenness" of the leaf samples and is closely related to the sufficiency or deficiency of nitrogen within the leaf and the yield. For each leaf segment in the digital image, the algorithm determines the DGCI and the area for that leaf segment. The algorithm calculates a single DGCI value for all of the leaf segments in the digital image from a weighted average of DGCI values of all leaf segments. The DGCI values of the standardized color disks are calibrated to the measured DGCI values using linear regression in order to eliminate any differences among the different cameras and/or lighting conditions. A two-point linear calibration for the known DGCI values of the comparative standard is compared to the two-point linear calibration of the measured DGCI values of the comparative standard, as determined by a particular camera. Correcting a camera's calibration to known values eliminates differences among cameras and/or lighting conditions. As can be seen from FIGS. 3 through 8, after correction, all combinations of DGCI values among the different cameras had correlation coefficients greater than 0.99 using the systems and methods disclosed herein.

In general, the systems and methods determine the average color of leaf sections by: (i) acquiring an image by digital photography, (ii) obtaining average RGB pixel values for the leaf sections within the digital image, and (iii) converting the RGB values to HSB values. The average RGB values of the digital images may be calculated using SigmaScan Pro 5.0 (SPSS, 1998). Using the predetermined threshold settings and the algorithm to average weighted RGB values, each digital image can be analyzed for individual objects within a predetermined threshold. The average red, average green, and average blue measurement settings are then used to obtain the average RGB levels for leaf sections in the digital image. Using the algorithm, the average RGB values can then be transferred into a spreadsheet (Microsoft Corporation, 1999) to facilitate the conversion of the RGB values to HSB values. The algorithm converts absolute RGB values (measured on a scale of 0 to 255) to percentage RGB values by dividing each value by 255. Percentage RGB values can then be converted to average HSB values using the algorithm as follows:

Hue:

$$\text{If } \max(R,G,B)=R, 60\{(G-B)/[\max(R,G,B)-\min(R,G,B)]\}$$

$$\text{If } \max(R,G,B)=G, 60(2+\{(B-R)/[\max(R,G,B)-\min(R,G,B)]\})$$

$$\text{If } \max(R,G,B)=B, 60(4+\{(R-G)/[\max(R,G,B)-\min(R,G,B)]\})$$

Saturation:

$$[\max(R,G,B)-\min(R,G,B)]/\max(R,G,B)$$

Brightness:

$$\text{Max}(R,G,B).$$

The HSB values can then be further developed into the DGCI, which encompasses dark green color on a scale of zero (0) to one (1) with values closer to one (1) representing a darker green. The DGCI is created to measure the relative dark green color of the digital image using the following equation:

$$\text{DGCI value}=[(H-60)/60+(1-S)+(1-B)]/3. \qquad \text{Equation 1}$$

The DGCI is calculated from the average of transformed HSB values. Each transformed value measures dark green color on a scale of zero (0) to one (1). Since the hue of most crop images range between 60° (yellow) and 120° (green), the maximum dark green hue is assigned as 120°. Therefore, the dark green hue transform can be calculated as (hue−60)/60, so that hues of 60° and 120° yield dark green hue transforms of zero (0) and one (1), respectively. Since lower saturation and brightness values corresponded to darker green colors, (1—saturation) and (1—brightness) may be used to calculate the dark green saturation and brightness transforms, respectively. The average of the transformed HSB values yield a single measure of dark green color, the DGCI value, which ranges from zero (0) to one (1) with higher values corresponding to darker green color.

The algorithm also separately analyzes each object in the digital image and gives individual values, such as on a separate line in the spreadsheet. After all the objects are scanned, the algorithm can exclude values that have a shape factor near the standardized color disks and average all other values in order to provide a final leaf DGCI value. A separate DGCI value is calculated for each of the standardized color disks, along with a corrected DGCI value for each digital image taken with each camera. The difference between actual and known DGCI values from the cameras is linear. The first step in calibration is to determine the difference between observed DGCI values and the known DGCI values for the standardized color disks. The slope of this relationship is:

$$\text{Slope} = \frac{(\text{Known } DGCI \text{ of } 1^{st} \text{ Disk} - \text{Known } DGCI \text{ of } 2^{nd} \text{Disk})}{(\text{Observed } DGCI \text{ of } 1^{st} \text{ Disk} - \text{Observed } DGCI \text{ of } 2^{nd} \text{ Disk})} \quad \text{Equation 2}$$

Once the slope is determined, the Y intercept can be calculated as:

$$Y \text{ intercept} = \text{Known DGCI of } 2^{nd} \text{ Disk} - (\text{Slope} \times \text{Observed DGCI for } 2^{nd} \text{ Disk}) \quad \text{Equation 3}$$

The corrected DGCI, based on the comparative standard, may then be calculated as follows:

$$\text{Corrected leaf DGCI} = (\text{Slope} \times \text{Observed Leaf DGCI}) + Y \text{ intercept} \quad \text{Equation 4}$$

The systems and methods are also directed to a predictive tool for determining nitrogen fertilizer requirements from DGCI measurements. For example, the systems and methods may utilize the crop's measured DGCI values to predict the amount of nitrogen fertilizer that should be applied to recover a predetermined crop yield potential, such as 90 to 95% of the maximum potential yield with a mid-season nitrogen application. The systems and methods utilize a mathematical model to form a calibrated yield potential response curve as a function based on the DGCI measurements. The mathematical model is a quadratic model described by:

$$f(x) = ax^2 + bx + c \quad \text{Equation 5}$$

The amount of nitrogen fertilizer required to achieve the maximum yield can be determined by taking the first derivative of Equation 5, setting $f(x)$ equal to 0, and solving for x, such that:

$$x = -b/2a \quad \text{Equation 6}$$

In practice, a yield potential would be between about 90 and 95% of the theoretical maximum yield because this relatively small decrease in yield requires substantially less nitrogen than required for the maximum yield.

The systems and methods disclosed herein may be implemented on various electronic delivery platforms capable of taking the digital image and running the appropriate analysis or fee-based, web-submission system. For example, the electronic delivery platform may be a stand-alone computer program/application designed to be packaged/embedded with any standard computer program/application ("host software application"). The electronic delivery platform may include a client application, a server application, a file repository and database for storage of images and information, and/or a database for storage of unique member and group identifier numbers. The electronic delivery platform may be implemented with one or more mainframe, desktop or other computer. For example, a computer device may use a 64-bit processor. Each computing device of the electronic delivery platform includes a central processor that controls the overall operation of the computing device and a system bus that connects the central processor to one or more conventional components, such as a network card or modem. Each computing device may also include a variety of interface units and drives for reading and writing data or files. Depending on the type of computing device, a user can interact with the computer with a keyboard, pointing device, microphone, pen device or other input device. The electronic delivery platform may be connected via a suitable network connection, such as a dial-up connection, a local area network ("LAN") connection, virtual private network connection or other network connection for computing devices.

In addition, the electronic delivery platform may include an application program that is resident on and run by a handheld, portable electronic device, such as a cell phone platform, for example Blackberry®, iPhone® or other smart phone electronic device or personal digital assistant ("PDA"). The handheld electronic device could take a digital photograph with the comparative standard. The digital image may be marked for processing, and a library of digital images may be stored in a file repository and database of the remote computing device of the systems and methods. Each digital image can be referenced by a unique identifier. The systems and methods may be implemented as a client/server application where the client electronic device having the digital image resident thereon connects to and communicates with the remote computing having the software and the algorithm loaded and resident thereon via the network connection. Upon submission, the client electronic device passes the digital image to the remote computer; the remote computer would perform the necessary steps to determine the nitrogen concentrations of the leaf and recommended nitrogen applications to maximize the potential crop yield from the submitted digital image. The remote computing device transmits the HSB values, the calculated DGCI and/or crop yield information back to the client electronic device via the network connection. After transmitting the results from the remote computing to the client electronic device, the network connection may be disconnected. The client electronic device may then either display in real-time or print the results or allow the user to manipulate the results for the needs of the particular situation.

Materials and Methods

Determining Nitrogen Levels in Non-legume Crops from Digital Image Analysis

The invention, in a first aspect, generally relates to the system and method of determining nitrogen levels in non-legume crops from a digital image. Measurement data below was collected from crop and field experiments within the state of Arkansas, with each field having a different soil type. A variety of non-legume corps, namely a range of corn hybrids, wheat, rice and turfgrass, were planted in respective fields and then subjected to a wide range of nitrogen fertilizer treatments. Photographs were taken of the crops with on the contrasting standard, either a bright pink, felt cloth or pink colored background/border, to provide greater contrast between leaves and standard for ensuing image analysis. The photographs included standardized color discs of yellow and green to serve as standards and to account for subtle lighting changes over the course of the process and for differences among cameras. SigmaScan Pro 5 (SyStat Software Inc., San Jose, Calif.) software was used to quantify greenness and determine DGCI. The yield and DGCI values from the experiments were expressed as a fraction of the treatment receiving the highest amount of nitrogen fertilizer for each field. The resultant relative yield and relative DGCI were then compared to each other with a single function. The system and method eliminated inter-field error and created a standard index by including a small area that was fertilized at a very high rate at each location, which established a benchmark for relative measurements and accounted for environmental factors.

Corn Greenhouse Study 2008

A greenhouse study was conducted to compare SPAD, leaf nitrogen sufficiency or deficiency and the DGCI in corn (*Zea mays* L.). Seeds of G90 sweet corn were sown on Jan. 8, 2008, in twenty-five (25) centimeter pots with an approximate soil volume of three (3) liters. The potting medium was a mixture of two-thirds LB2 potting mix having a vermiculite, perlite and peat mix (Sun Gro Co., Bellvue, Wash.) and one-third sifted Captina Silt Loam having a fine-silty, siliceous, active, mesic Typic Fragiudults (Arkansas Agriculture and Extension Center, Fayetteville, Ariz.). Four (4) seeds were planted per pot and thinned to two (2) plants after emergence. Pots were supplied nitrogen from a modified Hoagland solution containing 0, 168, 336, 504, 672, or 840 milligrams nitrogen per two (2) liters in the form of nitrate ($NO_3^-$). Solution pH was adjusted to approximately 6.8 before being applied to a thirty (30) centimeter saucer underneath each of the pots. All pots were kept well-watered using deionized water. The study design was a randomized complete block with two (2) replications.

Figure 1A:
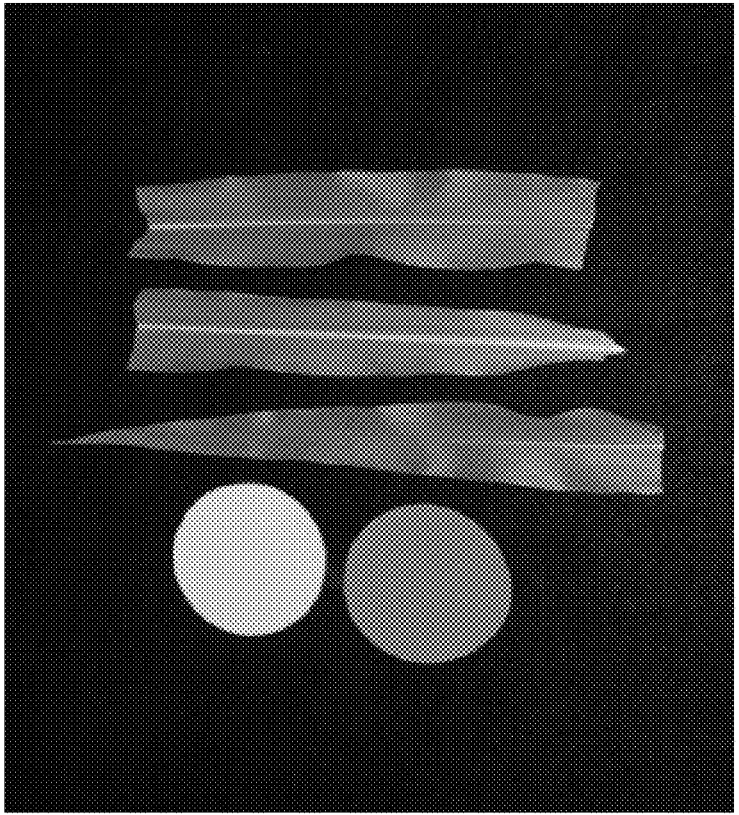

Plant sampling occurred at V3 to V5 stages and the uppermost collared leaf, i.e., youngest leaf with a ligule, was removed from each treatment. Leaves were placed against a black felt background under normal fluorescent lighting and photographed from a stationary camera pole set to a height of approximately fifty-eight (58) centimeters, and at an angle of approximately 40° offset from vertical. (FIG. 1A). An Olympus C-3030 (Olympus America Inc., Melville, N.Y.) digital camera was set to an ISO of 100, a shutter speed of ⅟15 seconds, an aperature of 2.0, exposure compensation of 0, and to fluorescent light balance with the flash turned off. The threshold ranges in SigmaScan were set at 30 to 120 for hue, and 27 to 100 for saturation. Leaf images were taken with and without a green and yellow comparative standard. The comparative standard was nine (9) centimeter circular standardized color disks with RGB values of 0, 135 and 0 for the green standardized color disk and 225, 225 and 0 for the yellow standardized color disk. The digital images were collected in JPEG (Joint Photographic Experts Group) format with a color depth of 16.7 million colors, and an image size of 1280×960 pixels (260 kilobytes per image). After the leaves were photographed, average SPAD readings were taken from each leaf. The leaves were then dried at 85° C. until the weight was constant, at which point they were ground through a twenty (20) mesh screen and submitted for total nitrogen analysis via Micro-Dumas combustion by the Soil Test and Plant Analysis Laboratory at the University of Arkansas.

Corn Greenhouse Study 2009

A greenhouse study was conducted in 2009 to further compare digital image color values with SPAD and leaf nitrogen sufficiency or deficiency, as well as to evaluate the ability to calibrate cameras of varying quality using an comparative standard within the digital images. Experimental design, treatment structure and sampling procedure were similar to the 2008 greenhouse study discussed infra except for number of cameras used, background color, threshold settings and calibration procedure.

Leaves were photographed against a pink felt background under normal fluorescent lighting. (FIG. 1B). Three (3) cameras were used to evaluate the comparative standard for camera calibration, a Canon Power Shot S51S (Canon U.S.A., Inc., Lake Success, N.Y.), a Fugi Fine Pix A400 (Fuji Photo Film Co., Ltd, Minato-Ku, Tokyo, Japan), and a Canon Power Shot A20 (Canon U.S.A., Inc., Lake Success, N.Y.). Threshold ranges in SigmaScan were set at 7 to 126 for hue and 0 to 100 for saturation, which allowed for a complete analysis of the entire leaf without including any of the background in the final leaf color value. Differences among cameras DGCI values before and after calibration with the comparative standard was evaluated by covariate analysis in which individual cameras served as the covariate.

The comparative standard comprised a green and yellow nine (9) centimeter diameter circular standardized color disks, which were cut from X-Rite color paper (X-Rite Inc., Kentwood, Mich.). The standardized color disks were placed a minimum of about 1.5 inches away from the leaf so that the shadow between the leaf and standardized color disks did not cause the algorithm to see the objects as one, and therefore, would not exclude the value of the standardized color disks from the final leaf value. Also, placement of the standardized color disks was closest to the camera during photographing because the digital images were not taken from a direct vertical angle, and therefore, the further away the standardized color disks, the more they appeared oval instead of round. If oval, the algorithm would not recognize the standardized color disks as objects to be removed from the final leaf value. The green standardized color disk had a Munsell color value of 6.7GY 4.2/4.1, hue of 91, saturation of 38, brightness of 42, and DGCI of 0.5722, and the yellow standardized color disk had a Munsell color value of 5Y 8/11.1, hue of 66, saturation of 88, brightness of 100, and DGCI of 0.0733. After all the objects were scanned, the algorithm excluded values that were near circular (shape factor≥0.8), and averaged all other values, giving one final leaf DGCI value.

Corn Greenhouse Results

The 2008 and 2009 greenhouse studies demonstrate that the SPAD and DGCI values are in correlation with $r^2$ being greater than 0.91. Using the lighter background in the 2009 greenhouse study having a color in the visible spectrum away from the green spectrum allowed the threshold ranges to be expanded and the precision of the method and system of determining nitrogen levels from a digital image to be increased. The SPAD and DGCI values were closely associated with leaf nitrogen sufficiency or deficiency.

Figure 3A:
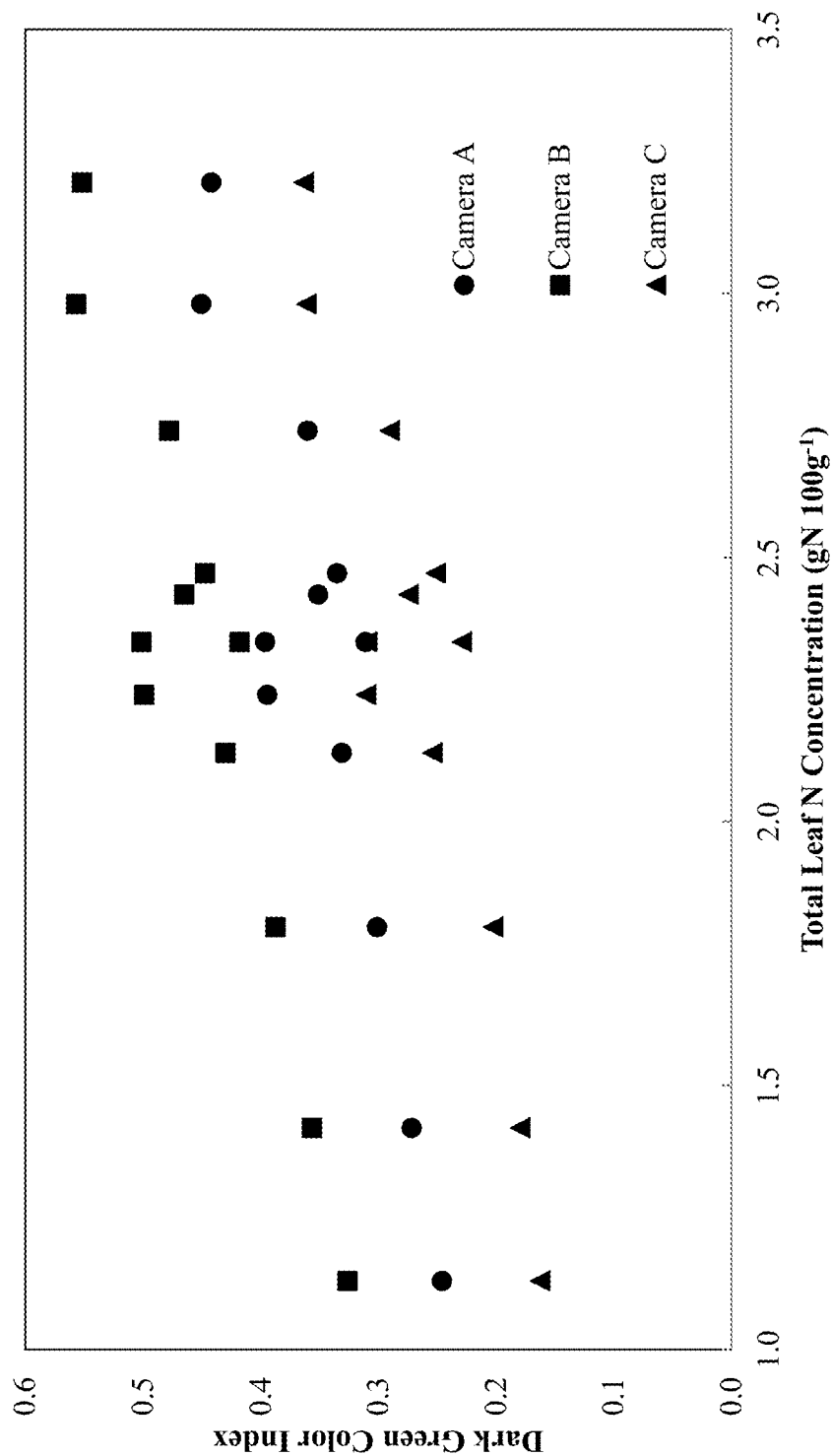
FIGS. 3A and 3B are graphical illustrations of dark green color index ("DGCI") values versus total leaf nitrogen concentration prior to (FIG. 3A) and after (FIG. 3B) using an comparative standard to correct for differences among the three (3) cameras used to photograph the leaves.
Figure 3B:
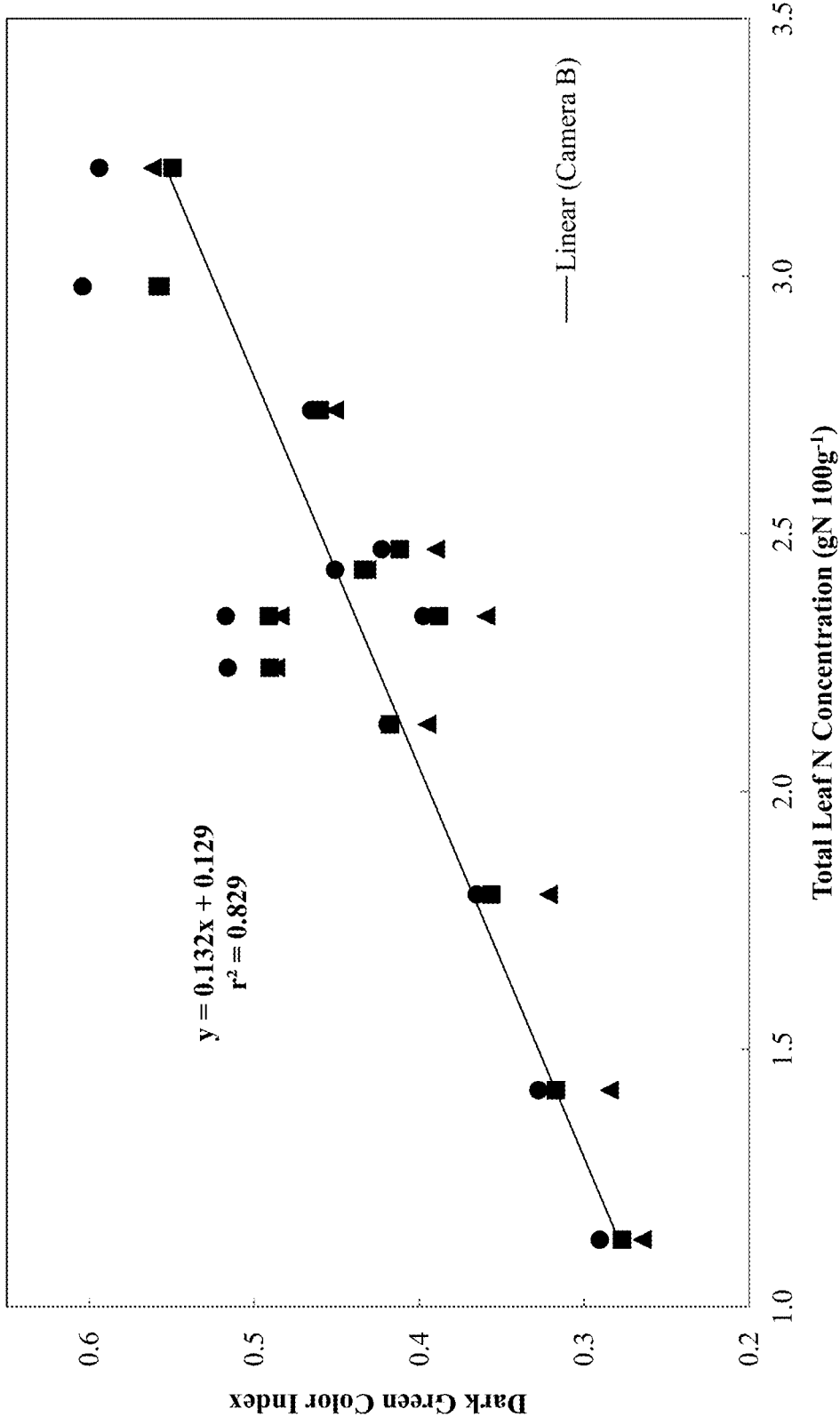
Figure 4A:
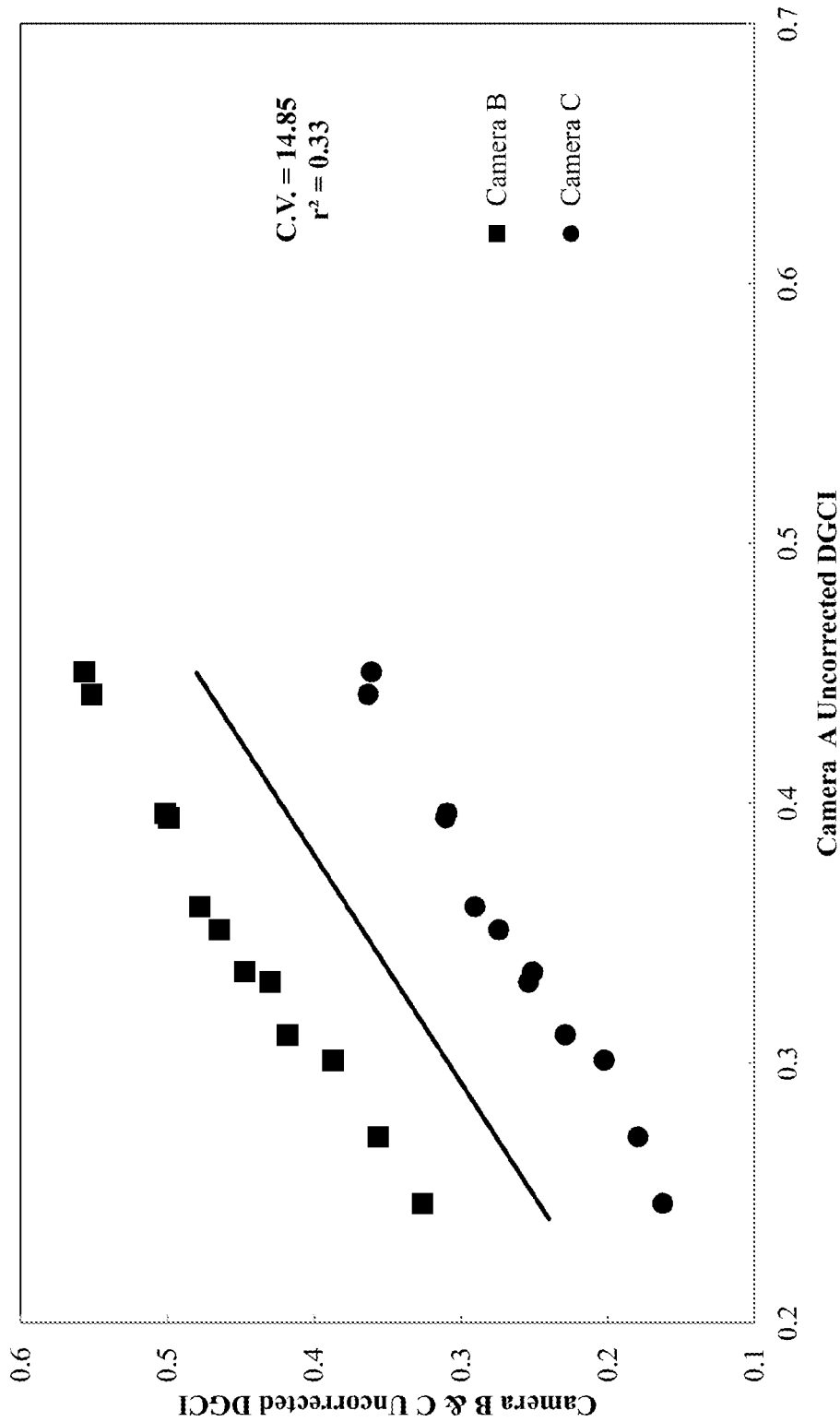
FIGS. 4A and 4B are graphical illustrations of DGCI values for cameras B and C versus the uncorrected DGCI value of camera A (FIG. 4A) and the corrected DGCI value of camera A (FIG. 4B)
Figure 4B:
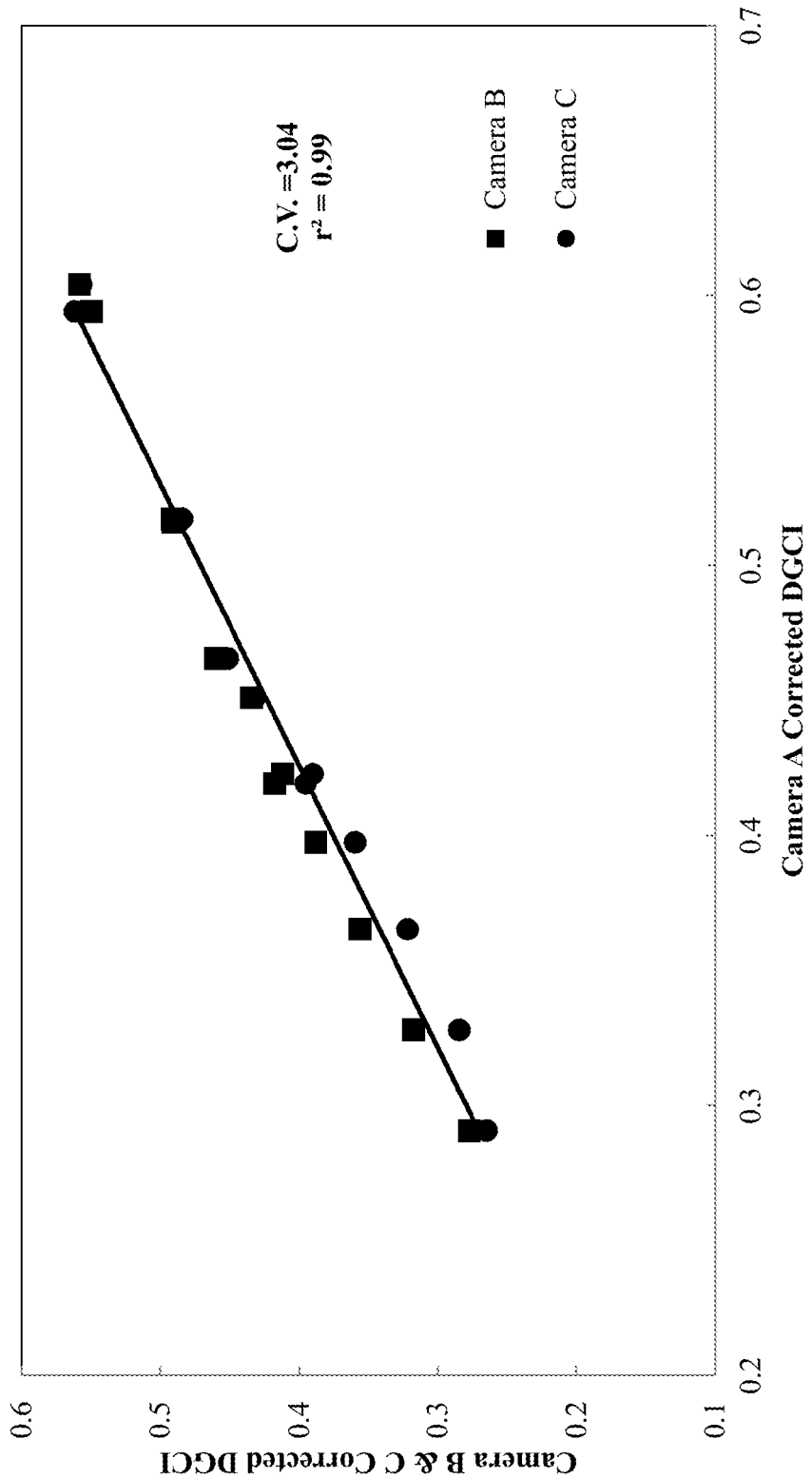

After calibration, the slope and intercepts for different cameras plotted against leaf nitrogen concentrations were not statistically different ($\alpha=0.05$). FIGS. 3A and 3B are graphs illustrating the relationship of uncorrected DGCI values (FIG. 3A) and corrected DGCI values (FIG. 3B) versus leaf nitrogen concentration among the three (3) different cameras for plants sampled on Mar. 3, 2009. FIG. 4A shows the uncorrected DGCI values for cameras B and C plotted against the uncorrected value of camera A. As can be seen from FIG. 4B, calibration reduces the coefficient of variation from 14.85 to 3.04 and increases the adjusted $r^2$ from 0.33 to 0.99.

Corn Field Study

A field study was conducted in five (5) fields located in Fayetteville, Marianna, Keiser and Rohwer, Ark. The study design was a randomized complete block with three (3) to five (5) replications. Nitrogen treatments ranged from 0 to 336 kg/ha$^{-1}$ (hand applied urea). The sampling procedure was similar to the greenhouse studies discussed infra. Rows were spaced at approximately one-hundred (100) centimeters, and the plots were fertilized to meet soil test recommendations for nutrients, except nitrogen. The plots were kept well-watered, and a crop yield was obtained.

Figure 5:
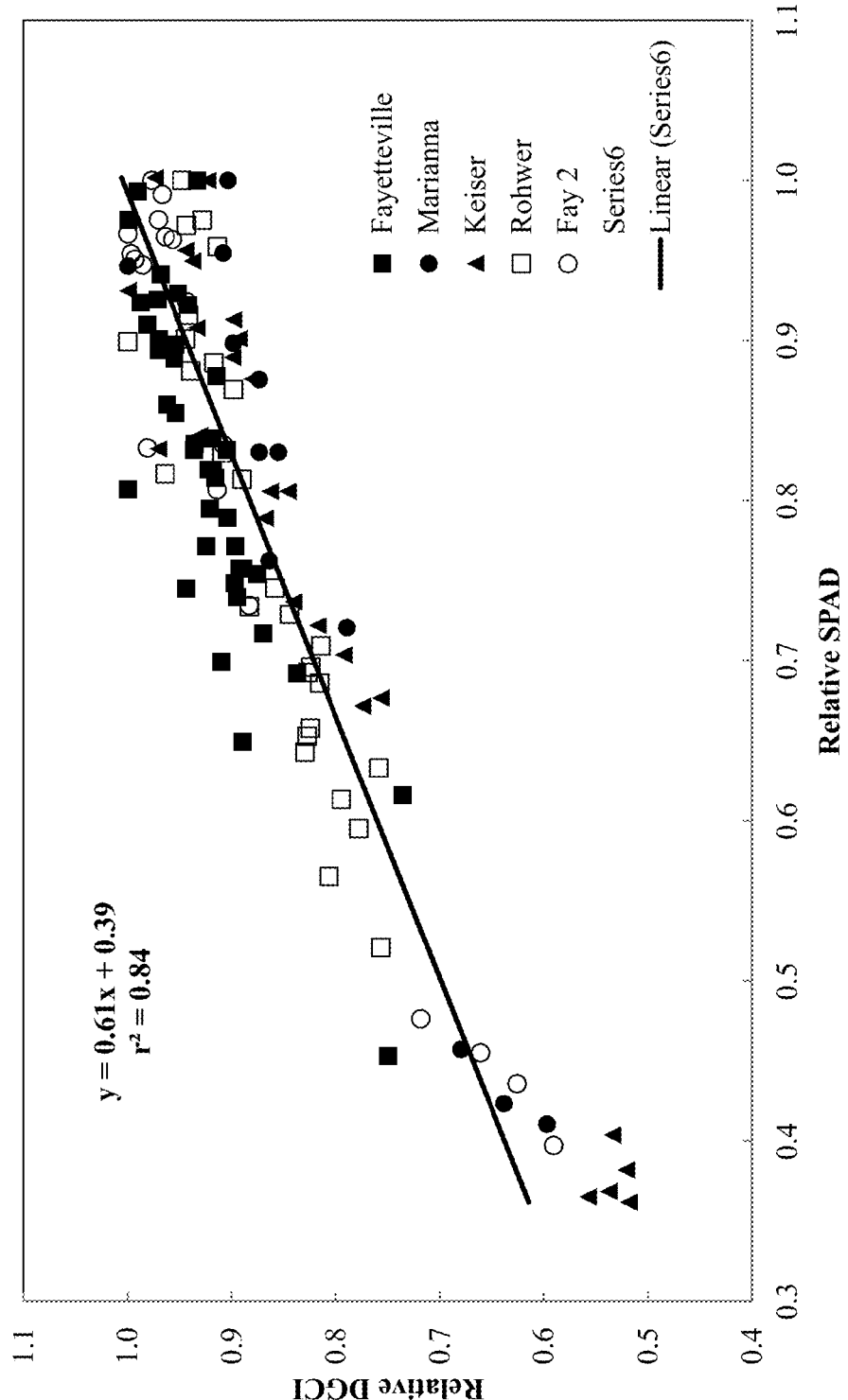
FIG. 5 is a graphical illustration of the relationship between relative DGCI values and relative SPAD values for all five (5) field locations.

Corn Field Results: Relationship Among DGCI, SPAD, and Leaf Nitrogen Concentration DGCI and SPAD correlated for all field locations with coefficients of determination ranging from 0.72 to 0.95. The ability to use the comparative standard as a means of calibrating the cameras greatly increased the agreement of SPAD and DGCI from 2008 to 2009. The relationship between relative DGCI and relative SPAD measurements for all locations is illustrated in FIG. 5, where the relative values of DGCI and SPAD can be used to show the correlation among treatments for multiple locations. Utilizing relative values lessens the effect of hybrid, soil type or environmental conditions. Composite regression data for all five (5) individual field locations and variables are listed in Table 1.

TABLE 1

| | Nc = Nitrogen concentration (g 100 g$^{-1}$) and Yield (kg ha$^{-1}$) | | | | | |
|---|---|---|---|---|---|---|
| Location | DGCI vs SPAD | DGCI vs leaf Nc | SPAD vs leaf Nc | Yield vs DGCI | Yield vs SPAD | Yield vs leaf Nc |
| Fayetteville 1 (Fay 1) | | | | | | |
| Slope | 0.004 | 0.083 | 14.08 | 46663 | 240.2 | 4795 |
| Intercept | 0.347 | 0.382 | 14.89 | −19825 | −4436 | −3999 |
| r$^2$ | 0.72 | 0.74 | 0.67 | 0.66 | 0.56 | 0.75 |
| n | 40 | 40 | 40 | 40 | 40 | 40 |
| Marianna | | | | | | |
| Slope | 0.006 | 0.134 | 20.91 | 42420 | 280.5 | 6138 |
| Intercept | 0.29 | 0.301 | 2.029 | −17127 | −5207 | −5221 |
| r$^2$ | 0.93 | 0.86 | 0.92 | 0.88 | 0.86 | 0.87 |
| n | 12 | 12 | 12 | 12 | 12 | 12 |
| Keiser | | | | | | |
| Slope | 0.008 | 0.165 | 18.79 | 28340 | 244.5 | 5339 |
| Intercept | 0.195 | 0.214 | 2.596 | −10858 | −5254 | −6485 |
| r$^2$ | 0.94 | 0.73 | 0.77 | 0.84 | 0.84 | 0.86 |
| n | 28 | 28 | 28 | 20 | 20 | 20 |
| Rohwer | | | | | | |
| Slope | 0.004 | 0.065 | 12.7 | 65302 | 344.8 | 4871 |
| Intercept | 0.341 | 0.423 | 19.65 | −29055 | −8440 | −2705 |
| r$^2$ | 0.82 | 0.85 | 0.87 | 0.81 | 0.83 | 0.90 |
| n | 28 | 28 | 28 | 28 | 28 | 28 |
| Fayetteville 2 (Fay 2) | | | | | | |
| Slope | 0.007 | 0.138 | 21.17 | 27217 | 206.6 | 4715 |
| Intercept | 0.247 | 0.28 | 1.07 | −9099 | −3038 | −3675 |
| r$^2$ | 0.95 | 0.80 | 0.92 | 0.83 | 0.90 | 0.87 |
| n | 18 | 18 | 18 | 18 | 18 | 18 |

Figure 6:
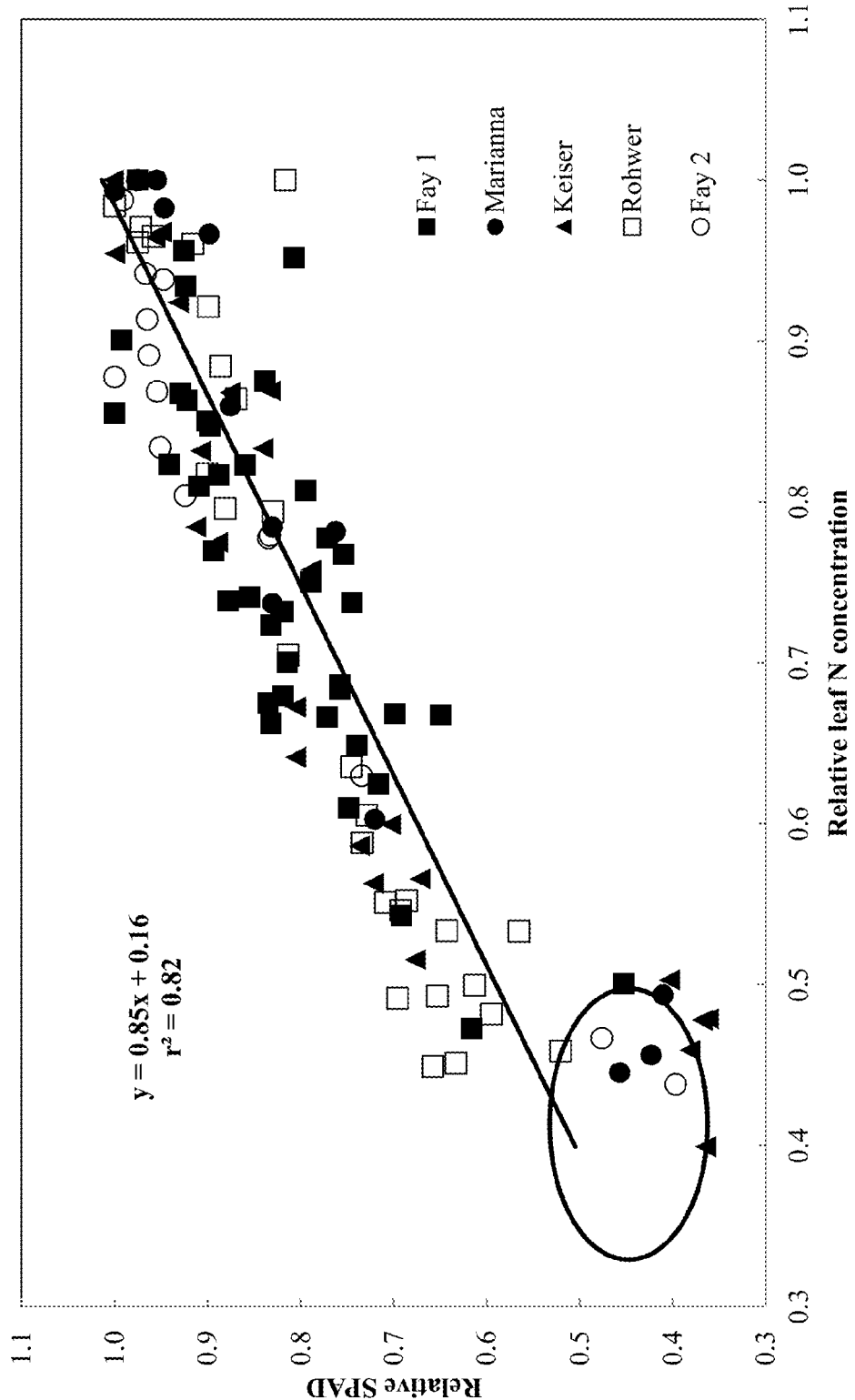
FIG. 6 is a graphical illustration of the response of the relative SPAD to an increase in the relative leaf nitrogen concentration.
Figure 7:
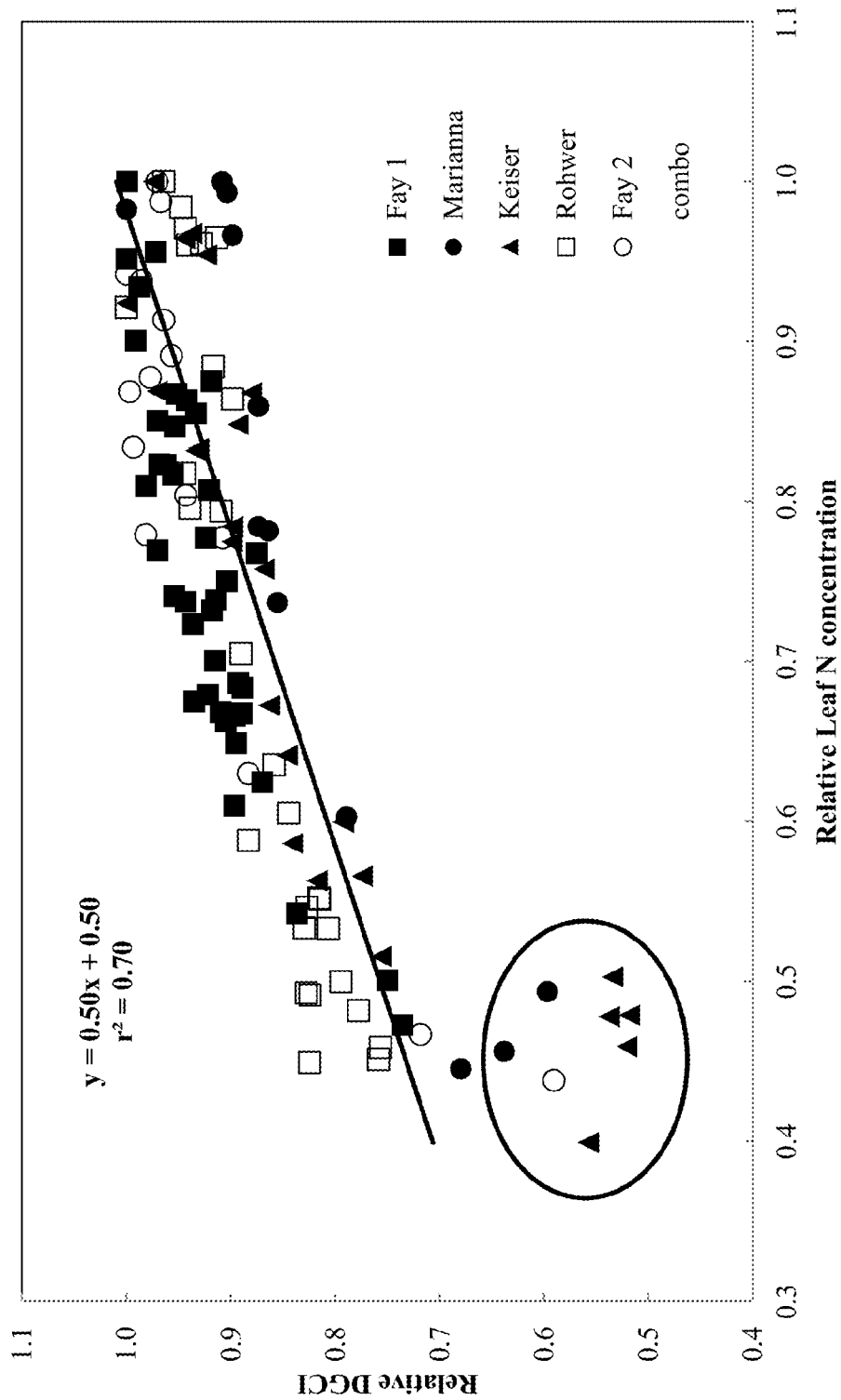
FIG. 7 is a graphical illustration of the response of the relative DGCI to an increase in the relative leaf nitrogen.

As can be seen, DGCI and SPAD values correlated with leaf nitrogen concentration for all field locations with average correlation coefficients of 0.80 for DGCI and 0.83 for SPAD. FIG. 6 graphically illustrates the response of relative SPAD to increasing relative leaf nitrogen concentration, while FIG. 7 graphically illustrates the relative DGCI response to increasing the relative leaf nitrogen concentration. As can be seen, the relative values of SPAD (FIG. 6) and DGCI (FIG. 7) to relative leaf nitrogen concentration were closely correlated even with five (5) different hybrids and multiple soil types for the five (5) different testing locations (FIG. 6). DGCI and SPAD both demonstrated accuracy in assessing leaf nitrogen concentration at tasseling. As illustrated in FIGS. 6 and 7, respectively, when relative leaf nitrogen concentration was less than 0.5 there was a poor association with either relative SPAD (FIG. 6) or relative DGCI (FIG. 7), and removing the circled values in FIGS. 6 and 7 increased the overall fit.

Figure 8A:
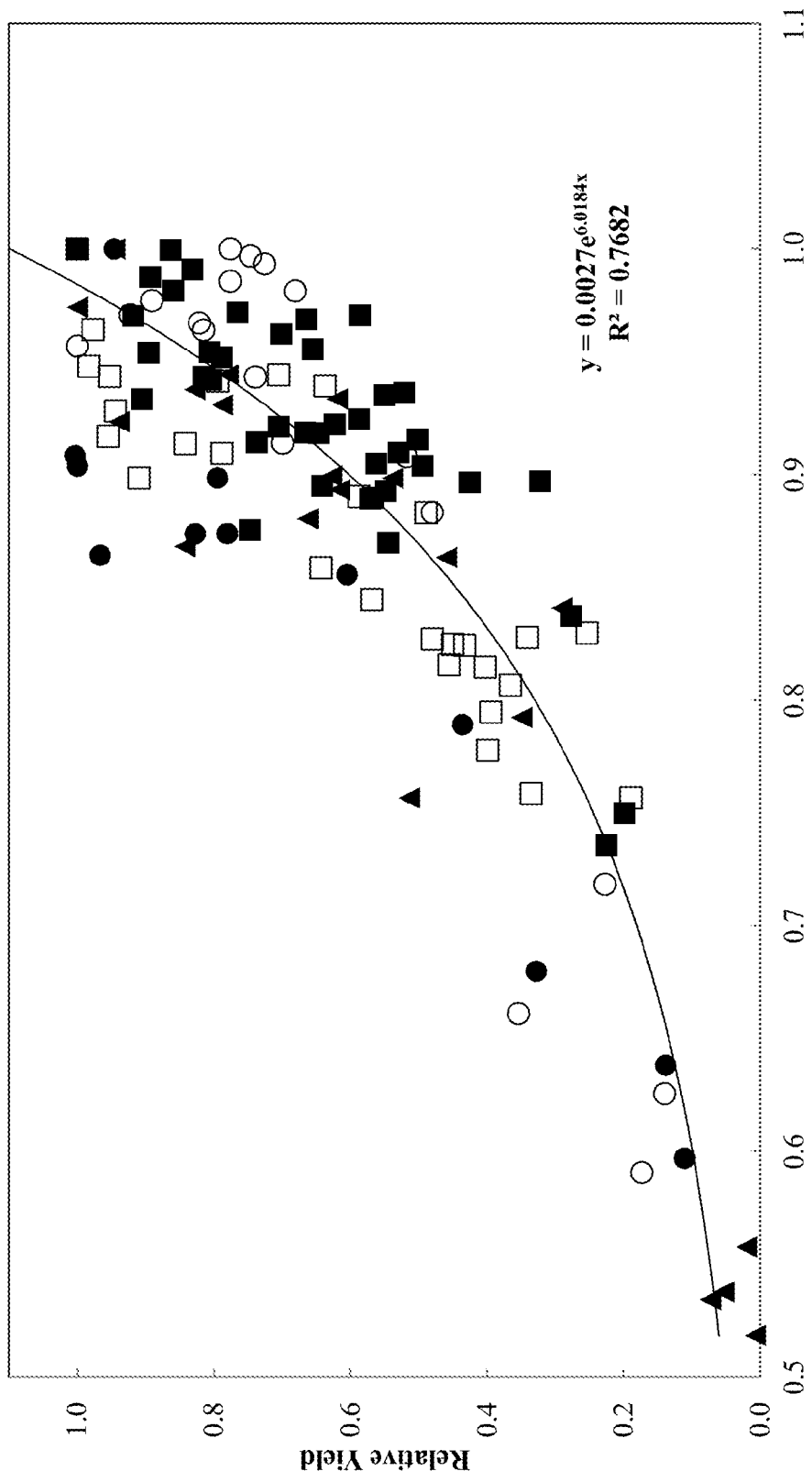
FIGS. 8A and 8B are graphical illustration of the response of relative yield of the crop to an increase in the relative DGCI value (FIG. 8A) and the relative SPAD value (FIG. 8B) sampled at tasseling for all five (5) field locations.
Figure 8B:
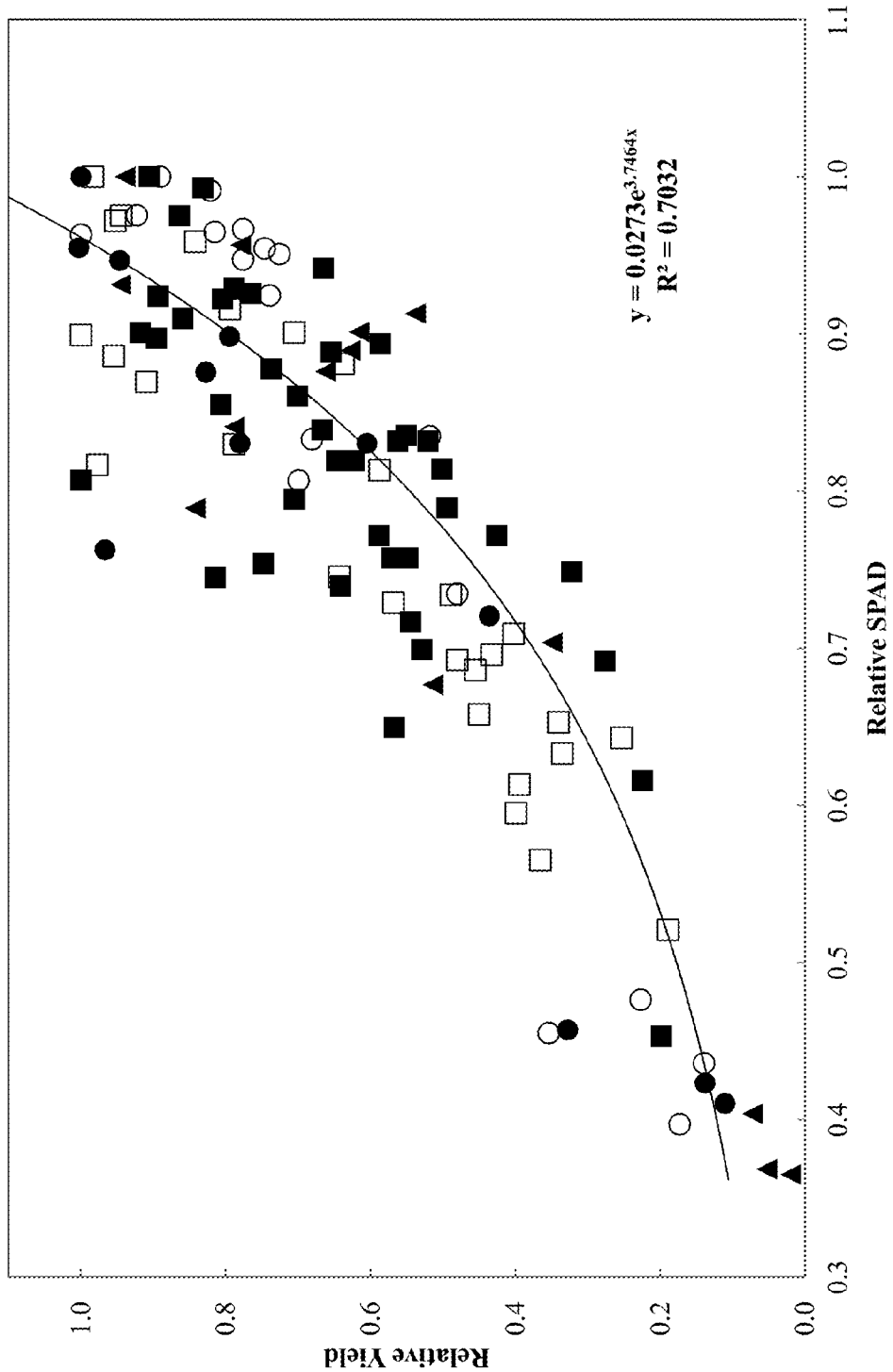

Corn Field Results: Relationship of DGCL SPAD, and Leaf Nitrogen Concentration to Yield DGCI and SPAD measurements taken at tasseling were closely associated with yield with coefficients of determination ranging from 0.67 to 0.88 for DGCI, and from 0.56 to 0.90 for SPAD. The two (2) lowest $r^2$ values for DGCI and SPAD were from the Fayetteville 1 location and occurred because the field was very sloped and nitrogen runoff was apparent. Plots were noticeably greener at the lower end of the field and resulted in abnormally high DGCI and SPAD values; furthermore, yield from plots with unknown amounts of available nitrogen could have caused coefficients of determination to be much lower than other the field locations. Average $r^2$ values of DGCI and SPAD plotted against yield for locations excluding Fayetteville 1 were 0.84 for DGCI and 0.86 for SPAD. The relative values of DGCI and SPAD plotted against relative yield for all field locations can be seen in FIGS. 8A and 8B, with FIG. 8A demonstrating the response of relative yield to increasing relative DGCI sampled at tasseling for all field locations and FIG. 8B illustrating the response of relative yield to increasing relative SPAD sampled at tasseling for all field locations.

Wheat Field Study

A field study was conducted to evaluate the relationship between leaf nitrogen concentration, the normalized difference vegetation index (NDVI), and DGCI values for soft red winter wheat. Delta King 9577 (Armor Seeds LLC, Jonesboro, Ariz.) was planted at the Arkansas Agricultural Research Extension Center in Fayetteville, Ariz. Soil was a Captina silt loam (fine-silty, siliceous, active, Mesic Typic Fragiudults). Plots consisted of six rows, 25 cm apart and 3 m long.

Soil nutrient amendments were applied according to University of Arkansas Extension recommendations with the exception of nitrogen. Nitrogen treatments were applied at rates of 0, 45, 90, 135, 180, or 225 kg ha$^{-1}$, either as pre-emergence, post-emergence, or an even split between the two, all prior to sampling. Nitrogen was applied in the form of urea (46-0-0) prills treated with dicyandiamide and nitrogen-(n-butyl) thiophosphotictriamide (Agrotain®, AGROTAIN International, St. Louis, Mo.). Experimental design was a randomized complete block with four replications.

Wheat was sampled twice, once at the Feekes 2-3, and again at approximately the Feekes 5 stage. The DGCI sampling was similar to the method described for corn: during midday, digital images were taken overhead of each entire plot. Included in each image was a prepared 0.5 m×1 m plywood board serving as the contrasting standard that supplied the necessary comparative color standard disks. NDVI measurements were made on the same plots using a GreenSeeker® 505 Handheld Sensor (Trimble Navigation Ltd., Westminister, Colo.). The sensor was set to take consecutive measurements by holding the sensor 0.5 m above the crop canopy in the center of the plot and walking at a steady pace for the length of the plot. Finally, ten (10) representative upper-most leaf samples were cut from each plot, dried, and analyzed for total nitrogen concentration with a LECO FP428 Nitrogen Analyzer (LECO Corporation, St. Joseph, Mich.) by the Agricultural Diagnostic Laboratory (University of Arkansas, Fayetteville).

Wheat Results

Figure 10A:
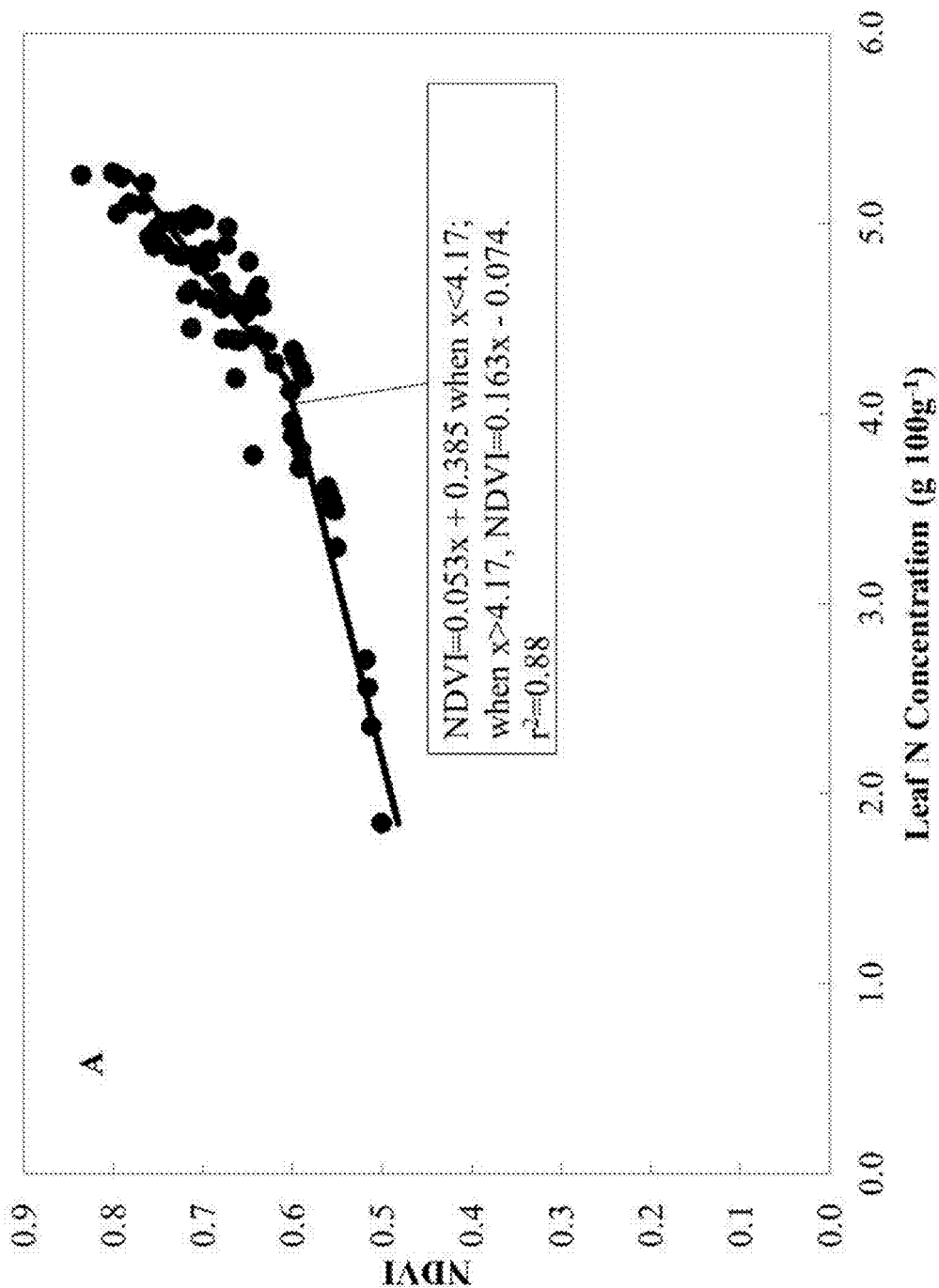
FIGS. 10A and 10B are graphical illustrations of the relationship between NDVI and leaf nitrogen concentration in winter wheat in 2011 at the Fayetteville site from (FIG. 10A) Mar. 17 and (FIG. 10B) Apr. 6, 2011.
Figure 10B:
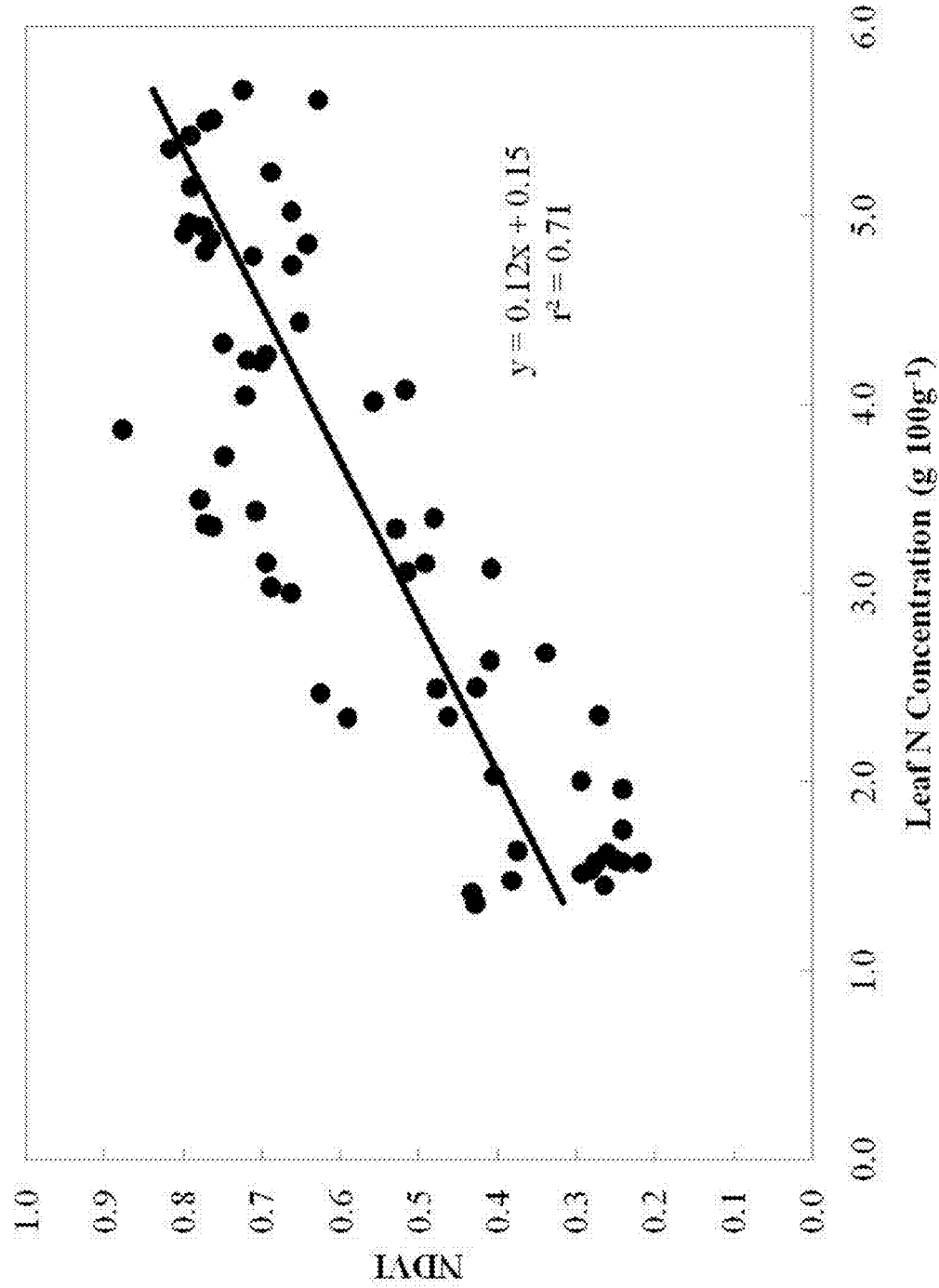
Figure 11A:
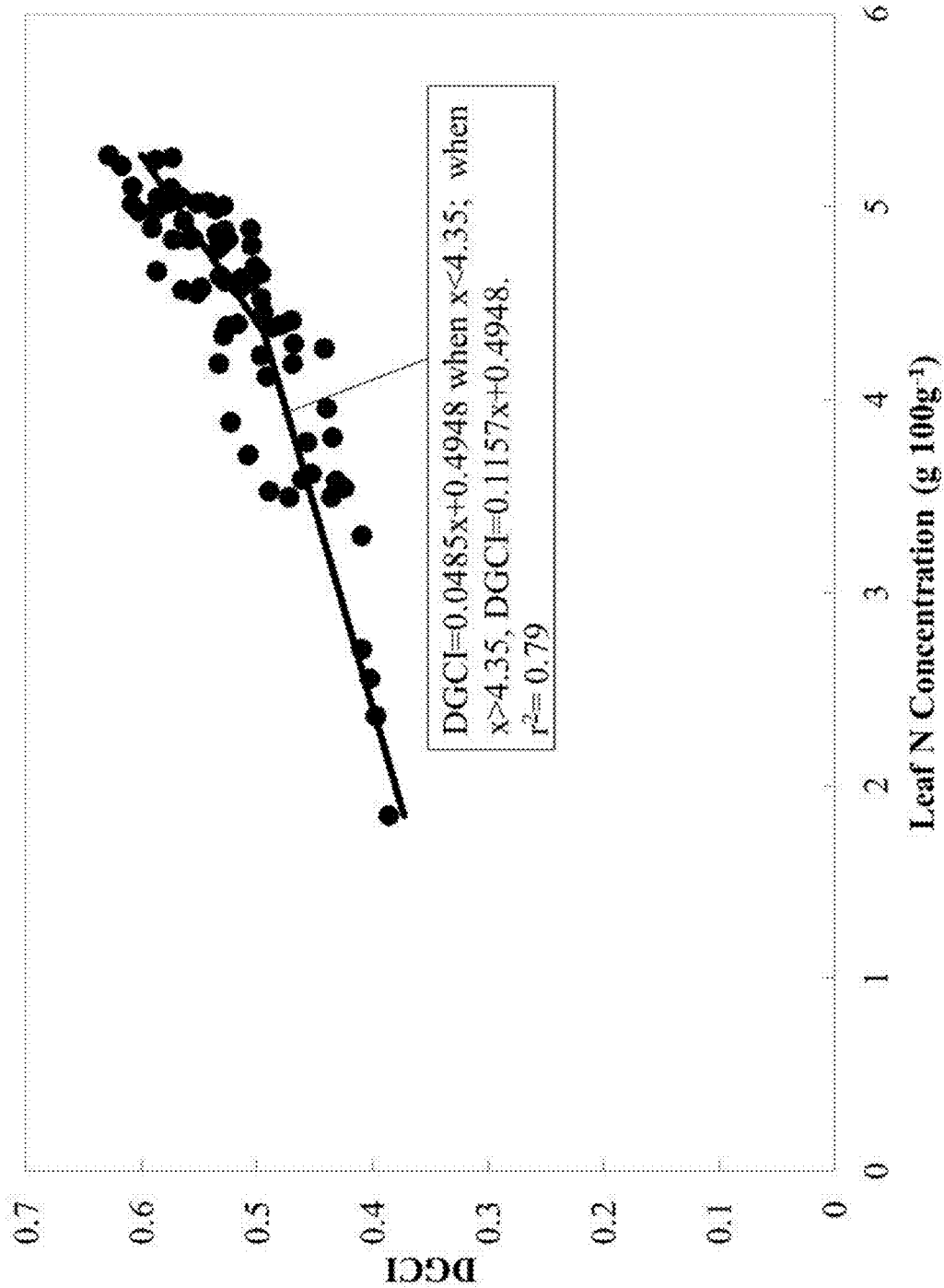
FIGS. 11A and 11B are graphical illustrations of the relationship between DGCI and leaf nitrogen concentration in winter wheat in 2011 at the Fayetteville site from (FIG. 11A) Mar. 17 and (FIG. 11B) Apr. 6, 2011.
Figure 11B:
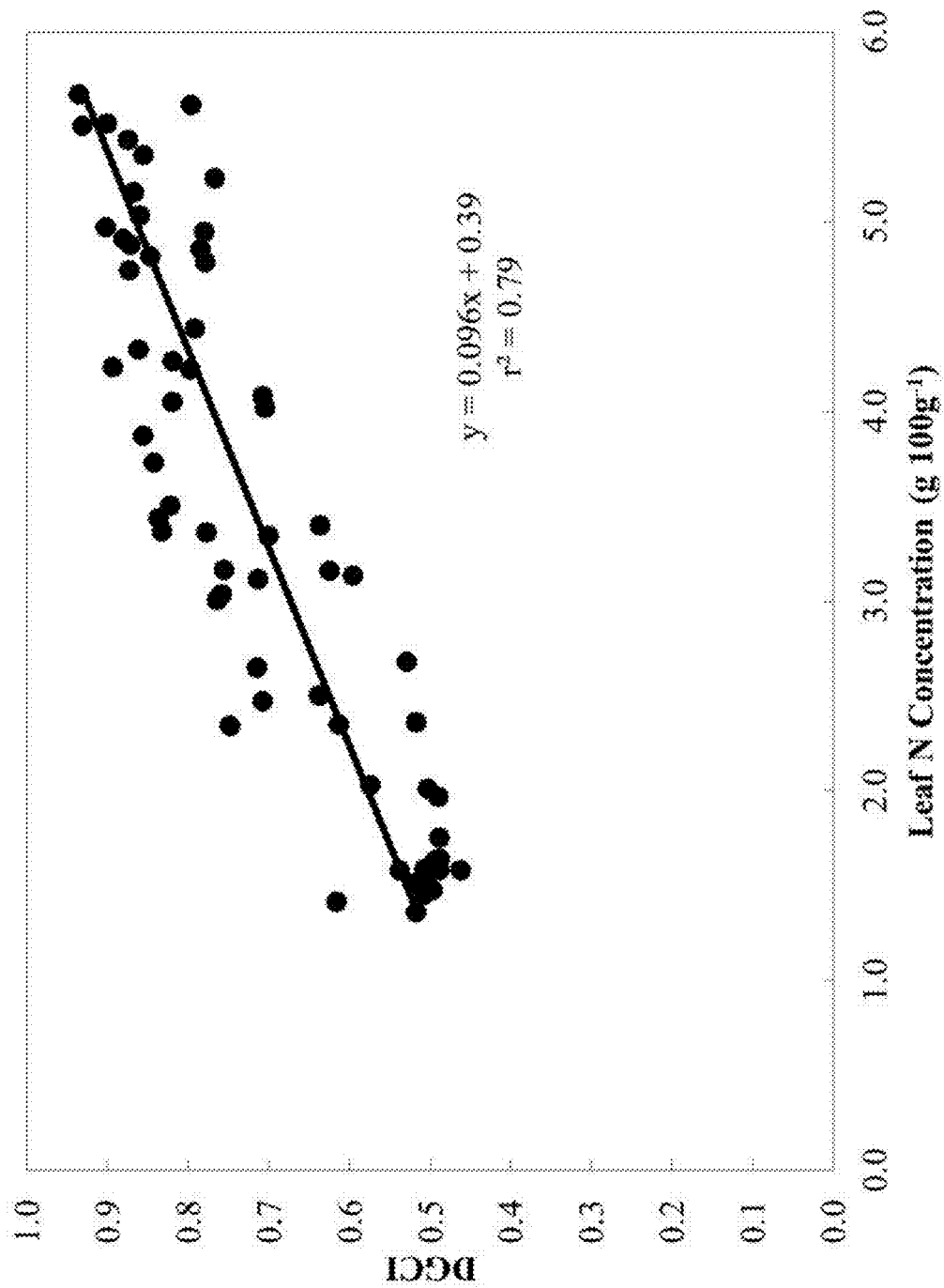
Figure 12A:
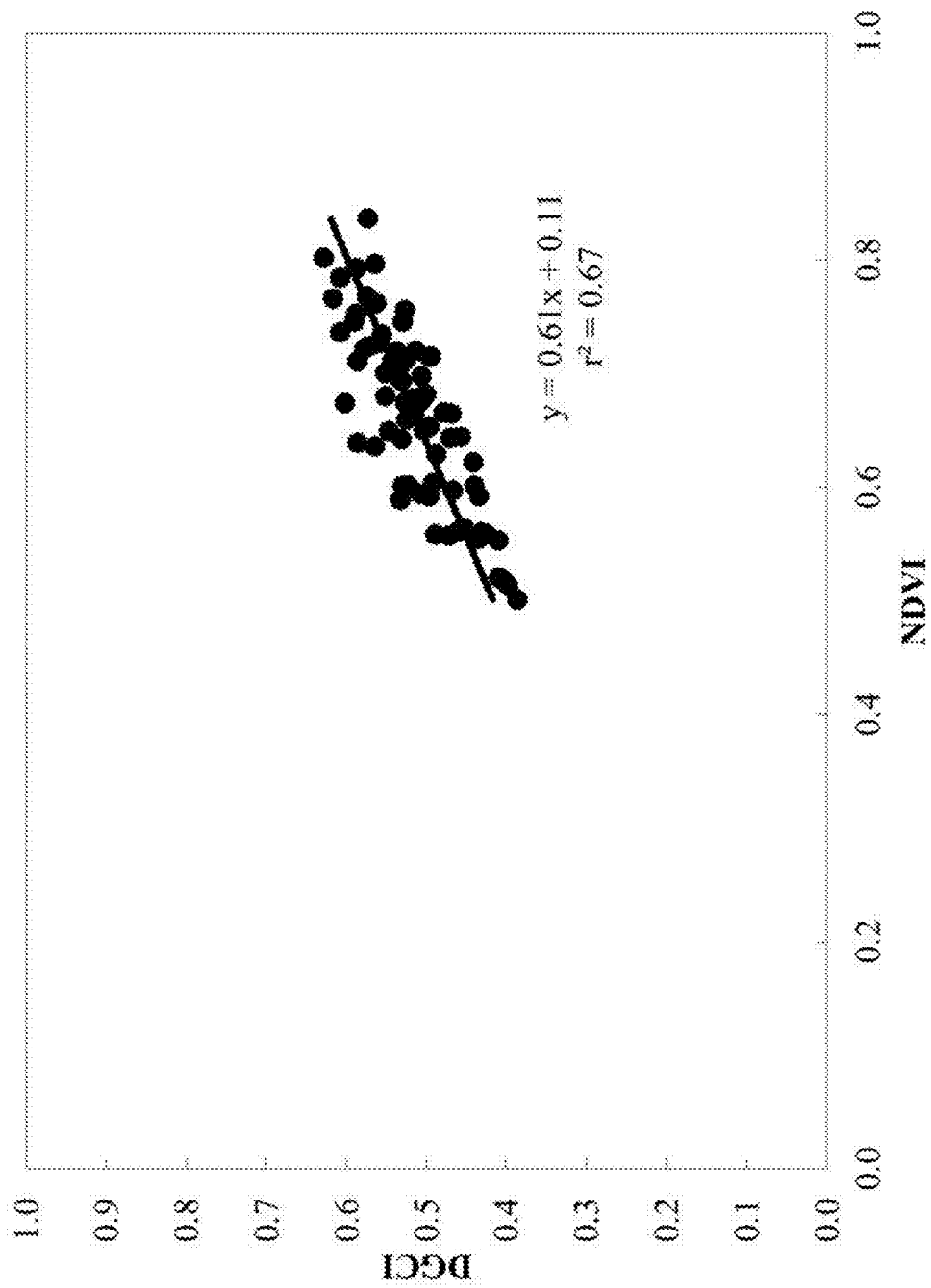
FIGS. 12A and 12B are graphical illustrations of the relationship between DGCI and NDVI in winter wheat in 2011 at the Fayetteville site from (FIG. 12A) Mar. 17 and (FIG. 12B) Apr. 6, 2011)
Figure 12B:
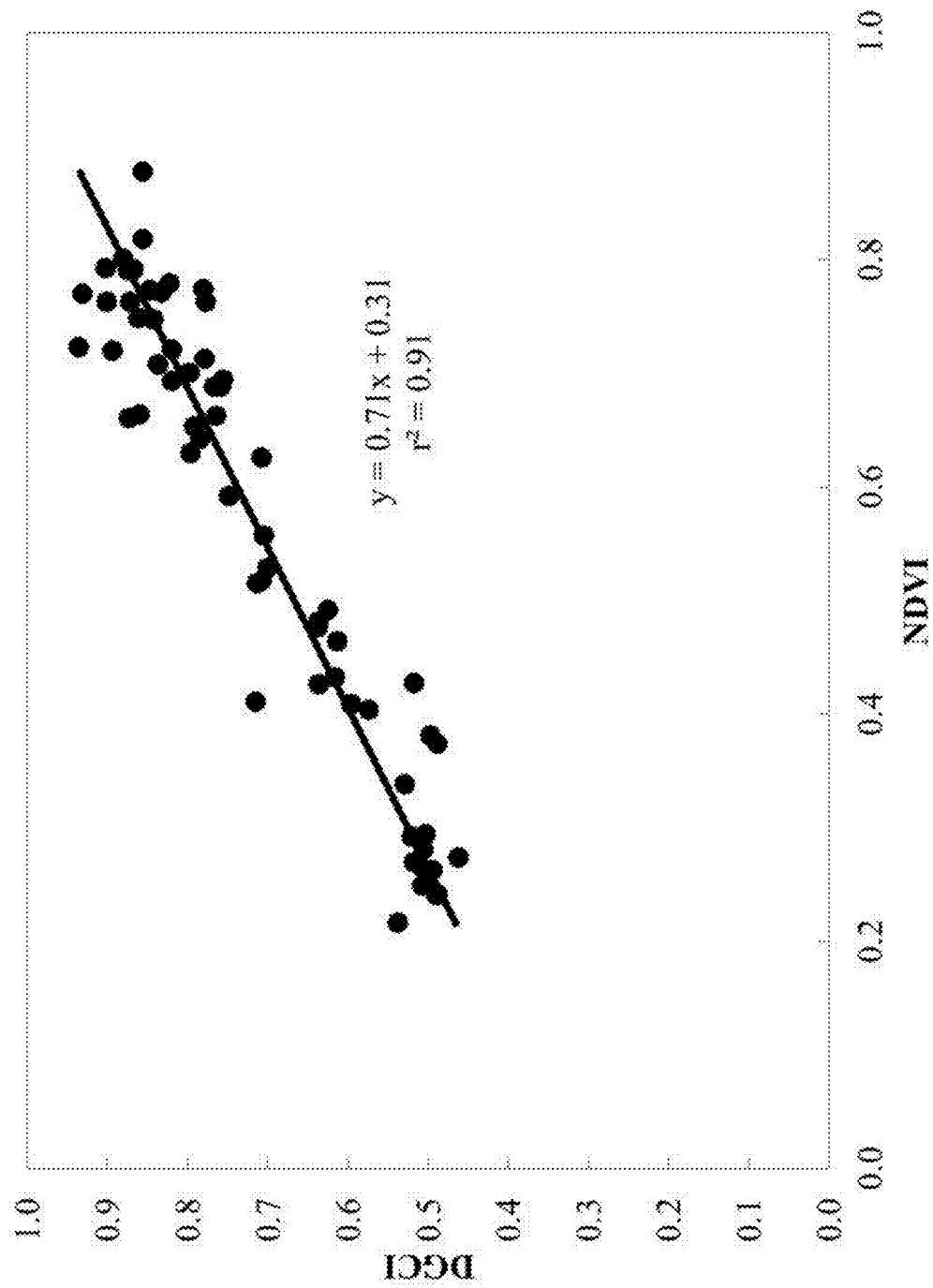

Data were comparable between the two (2) sampling dates with regards to leaf nitrogen, DGCI, and NDVI relationships. At the first sampling, Feekes 2-3 growth stage, there were good relationships between both NDVI and leaf nitrogen concentration ($r^2$=0.88, p<0.0001, FIG. 10A) and DGCI ($r^2$=0.74, p<0.0001, FIG. 11A) with leaf nitrogen concentration. For both groups of measurements taken on this first date, the data fit to a segmented linear regression with a breakpoint between 4.2 and 4.4 g nitrogen 100 g$^{-1}$. Similar observations were made on the second sampling date (FIGS. 10B and 11B), though the data did not warrant a segmented regression. Though the measurements for the first sampling date showed a more narrow range of leaf nitrogen concentration, DGCI, and NDVI, the segmented regression suggests nitrogen stress differentiation may have resulted from different factors between sample dates. The DGCI and NDVI measurements were closely associated with each other, increasing in strength from the first to second sampling dates. (FIGS. 12A and 12B).

Turf

Commercial varieties of creeping bentgrass (variety G-2), 'Riviera' Bermudagrass (*Cynodon dactylon* (L.) Pers.), and 'Rebel Exeda' tall fescue (*Festuca arundinacea* L.) were examined to evaluate the relationship between leaf nitrogen concentration and DGCI in Fayetteville, Ariz. Soil was a Captina silt loam (fine-silty, siliceous, active, Mesic Typic Fragiudults).

Soil nutrient amendments and irrigation were applied according to University of Arkansas extension recommendations with the exception of nitrogen, which was applied at rates of 0, 25, 50, 75, or 100 kg ha$^{-1}$. The bermudagrass observed was part of a larger study that evaluated an adjuvant, NutriLife® (NLAF, Advanced Microbial Solutions, Pilot Point, Tex.), which was applied at three rates of 0, 4.2 (1.0×), and 6.3 (1.5×) ml kg$^{-1}$ with the nitrogen fertilizer.

Sampling occurred 7 to 10 days after fertilizer application. DGCI data were collected by taking digital images as described previously. Leaf samples were taken concurrently and analyzed for total nitrogen concentration.

Turf Results

Figure 13:
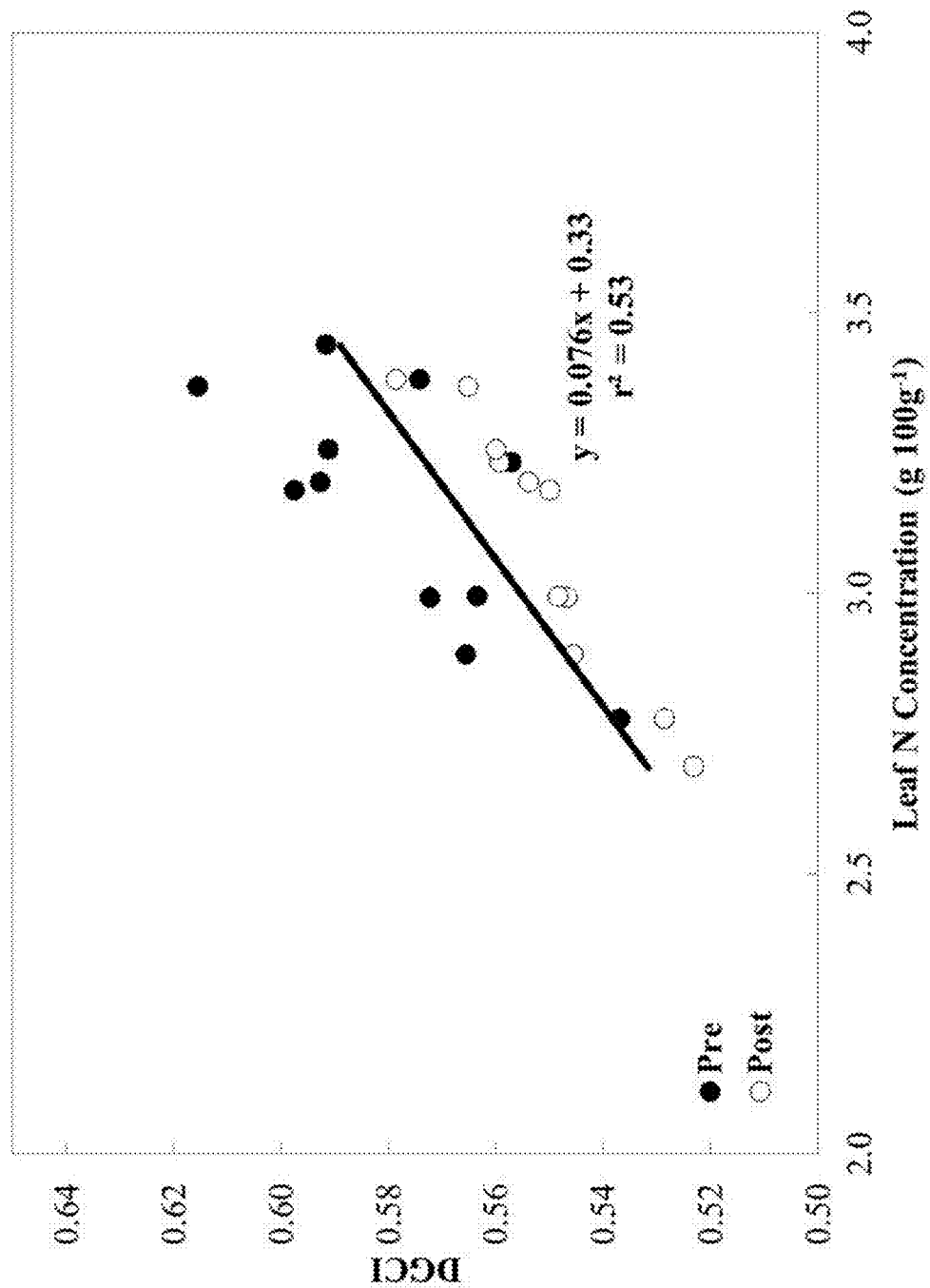
FIG. 13 is a graphical illustration of the relationship between leaf nitrogen concentration and DGCI from samples of tall fescue taken both pre- and post-mowing, though covariate analysis revealed no significant differences between the two sample groups.

Measurements were conducted on a small number of samples of tall fescue (n=11) and bentgrass (n=11). DGCI measurements were made twice on a group of tall fescue plots, once before and once after mowing. (FIG. 13). Leaf clippings from the mowing were immediately submitted for total nitrogen analysis. Covariate analysis revealed no significant differences in slope or intercept between the two sample groups (mowed and unmowed), which together had an $r^2$ of 0.53 (p<0.0001).

Figure 14:
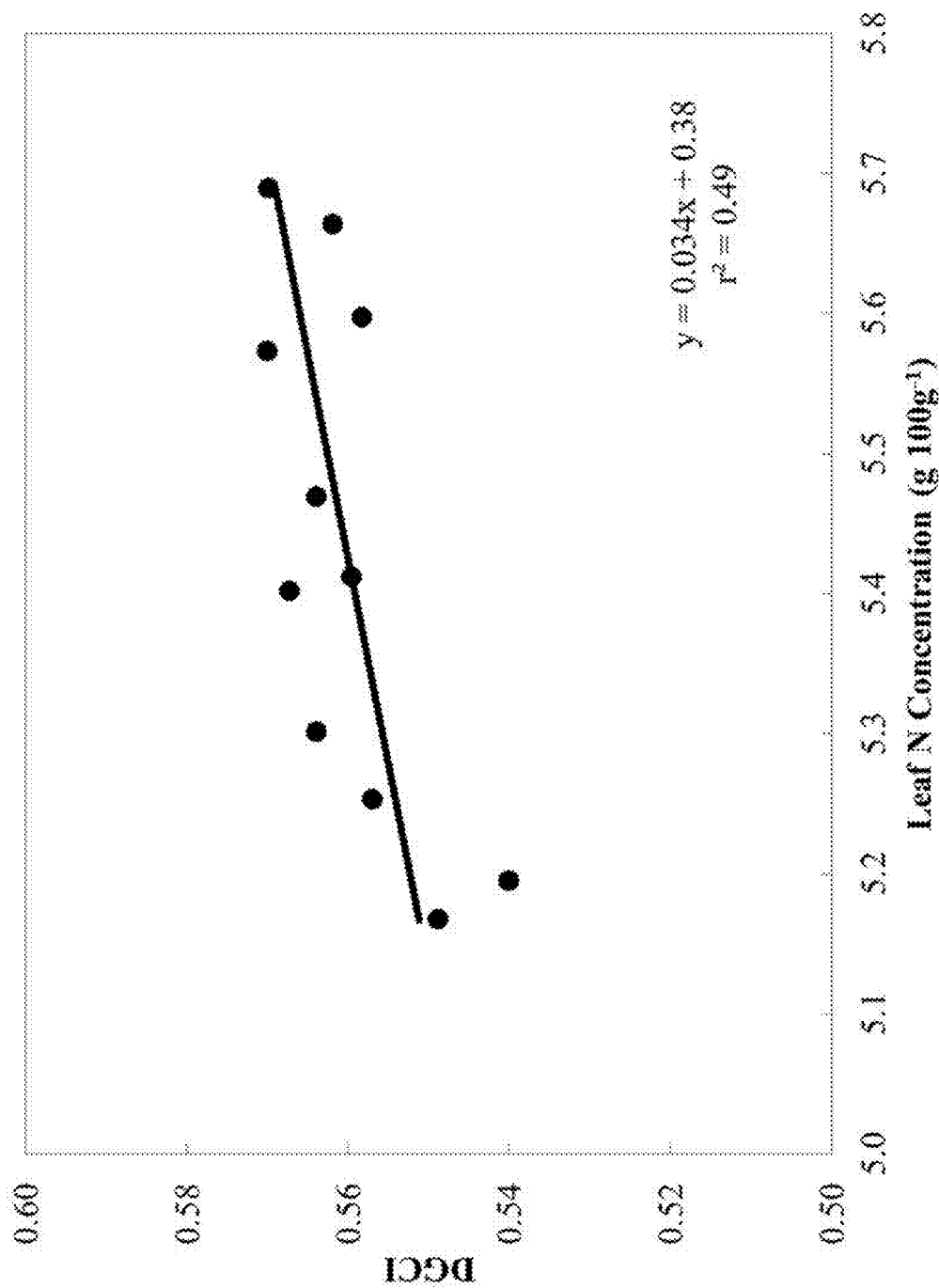
FIG. 14 is a graphical illustration of the relationship between leaf nitrogen concentration and DGCI values for bentgrass plots in 2011 at the Fayetteville site.

There was little difference in nitrogen concentration of bentgrass samples, with a range from 4.9 to 5.7 g 100 g$^{-1}$. As with tall fescue, there was a narrow range of DGCI, from 0.54 to 0.57. Nevertheless, there was a significant relationship ($r^2$ of 0.49, p<0.0001) between DGCI and leaf nitrogen concentration. (FIG. 14).

Figure 15:
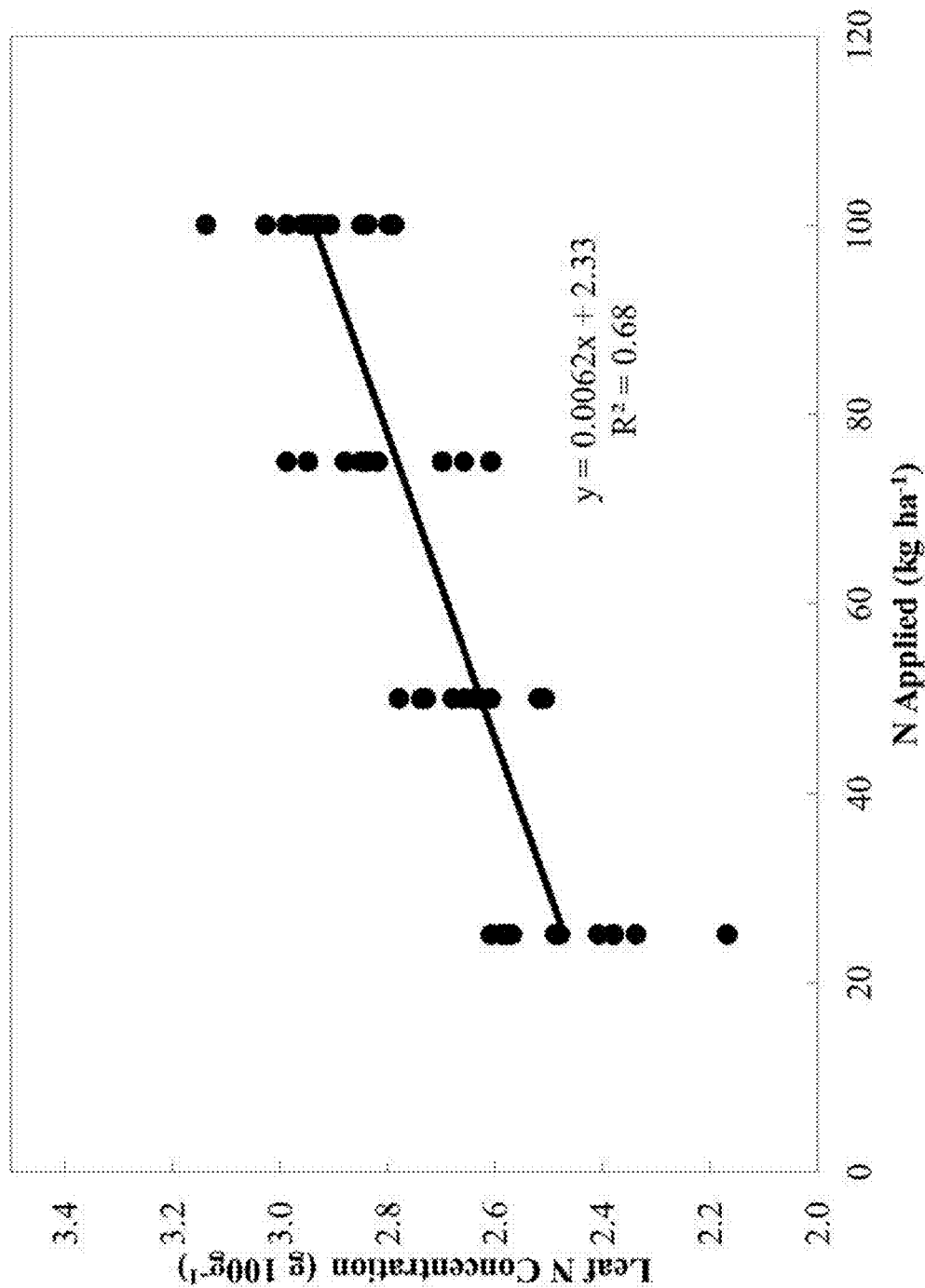
FIG. 15 is a graphical illustration of the relationship between leaf nitrogen concentration and amount of nitrogen applied to Bermudagrass in Fayetteville, 2011. Applications were made with three different levels of NutriLife (soil amendment containing 3% nitrogen and several strains of *Bacillus* bacteria intended to catalyze nitrogen uptake), though covariate analysis found no significant difference between NLAF rates. Data points are averages for all replications of each nitrogen rate.

As the bermudagrass was fertilized with an adjuvant, NLAF, the response of leaf nitrogen concentration and DGCI among the three NLAF treatments was examined using covariate analysis. No significant treatment effect was observed for NLAF application rates with regards to the leaf nitrogen-concentration response to nitrogen application rates. Therefore, leaf nitrogen concentration response to amount of nitrogen fertilizer applied had similar intercepts and slopes regardless of the NLAF adjuvant ($R^2$ of 0.68, p<0.0001, FIG. 15).

Figure 16:
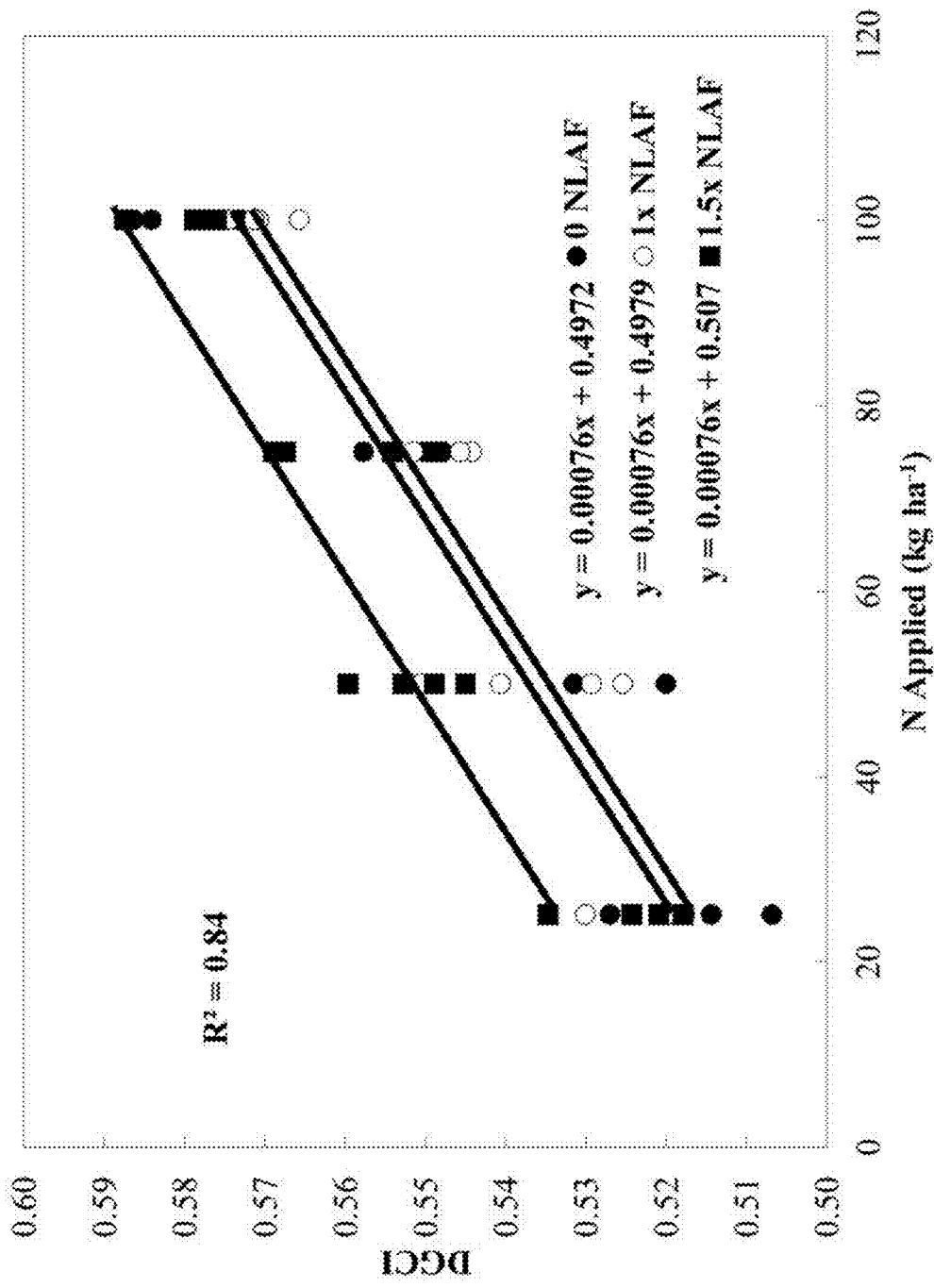
FIG. 16 is a graphical illustration of the relationship between DGCI measurements and amount of nitrogen applied to bermudagrass in Fayetteville in 2011. Treatment blocks were initially divided among those receiving various levels of NutriLife (a soil amendment containing 3% nitrogen and several strains of *Bacillus* bacteria intended to catalyze nitrogen uptake). Covariate analysis revealed responses with differing intercepts but a common slope. Data points are average values for each N rate within a treatment block.
Figure 17:
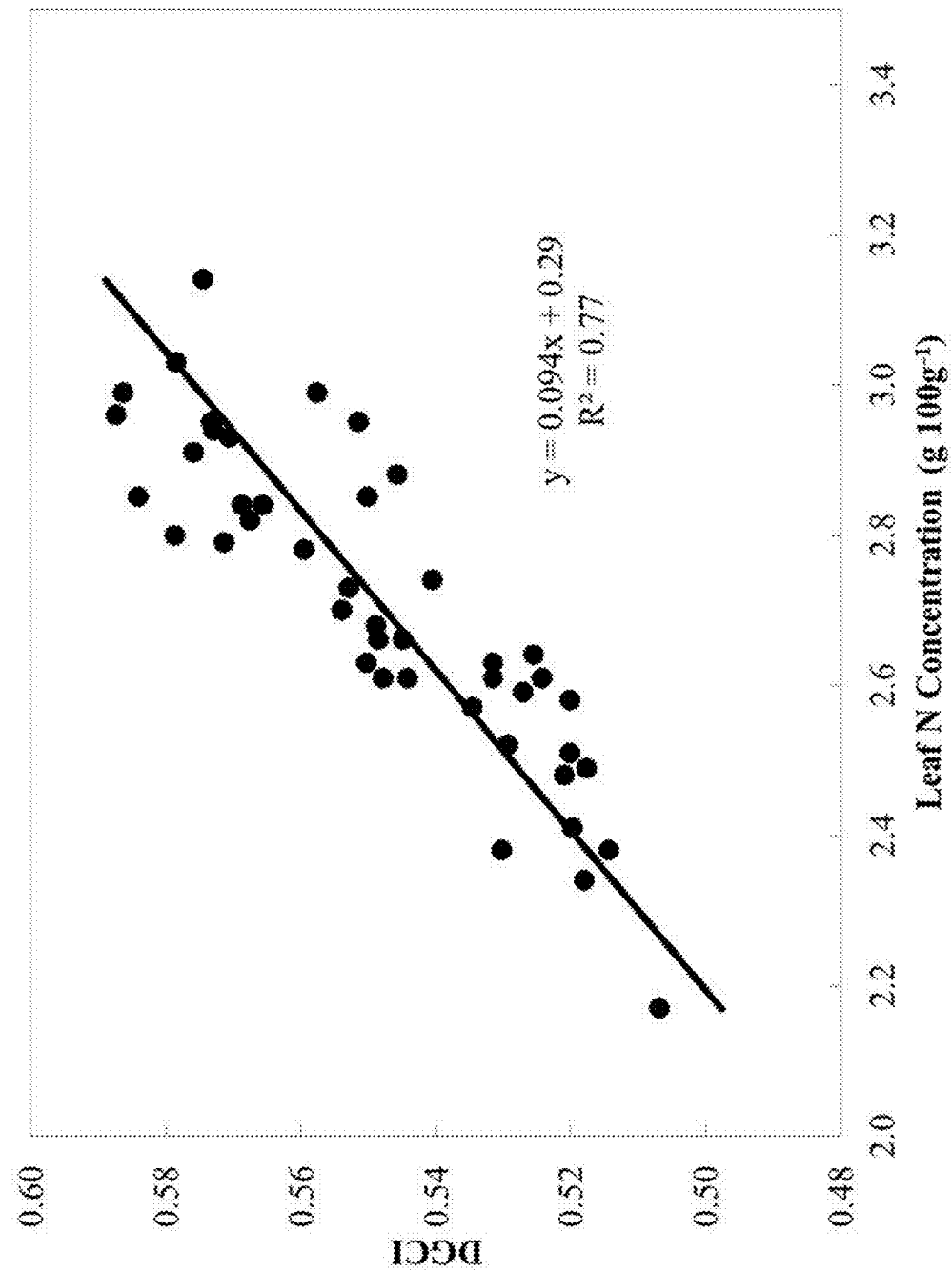
FIG. 17 is a graphical illustration of the relationship between DGCI measurements and leaf nitrogen concentration in bermudagrass from field experiments in Fayetteville in 2011. Treatment blocks were initially divided among those receiving various levels of NutriLife (a soil amendment containing 3% nitrogen and several strains of *Bacillus* bacteria intended to catalyze nitrogen uptake), though covariate analysis found no significant difference between NLAF treatment levels.

Covariate analysis indicated that the response of DGCI to the amount of nitrogen applied had similar slopes for the NLAF treatments but different intercepts ($R^2$ of 0.84, p<0.0001, FIG. 16). The highest rate of NLAF (1.5×) resulted in higher DGCI values than the control and 1.0× treatment. Covariate analysis revealed no significant effects of the three NLAF rates on the DGCI response to leaf nitrogen concentration (FIG. 17). There was a linear increase in DGCI as leaf nitrogen increased, regardless of NLAF treatment ($R^2$ of 0.77, p<0.0001).

The wheat and turf species evaluated had strong relationships between DGCI values and leaf nitrogen concentration, similar to that observed in corn. In the case of wheat, the DGCI method compared favorably to concurrent NDVI measurements. DGCI and NDVI also had a strong relationship with each other ($r^2$=0.91, FIG. 12B) at the later sampling date, suggesting that the methods are effective in similar situations, such as when canopy coverage is greater at mid-vegetative states.

In-Season Nitrogen Measurement and Fertilization of Non-Legume Crops from Digital Image Analysis The invention, in a second aspect, generally relates to the system and method of in-season nitrogen measurement and fertilization of non-leguminous crops from digital image analysis. The systems and methods quantify relationships among yield, leaf nitrogen concentration, SPAD, and DGCI and provide calibration curves relating DGCI or SPAD to subsequent nitrogen applications for achieving target yields. Measurement data below was collected by planting corn at five (5) locations over two (2) years in Arkansas, and then subjecting the crops to varied early season and midseason nitrogen applications. The relative nitrogen sufficiencies or deficiencies were estimated using DGCI, SPAD, and leaf nitrogen. Data over both years reveal a significant relationship at midseason (V6 to V10) between DGCI and SPAD ($r^2$=0.48 to 0.87), DGCI and leaf nitrogen concentration ($r^2$=0.56 to 0.70), and SPAD and leaf nitrogen concentration ($r^2$=0.43 to 0.80) in corn. Crops with varying early-season nitrogen deficiencies demonstrated a non-linear, quadratic response to midseason nitrogen applications. Combining the responses of yield to midseason nitrogen application rates with concurrent mid-season DGCI measurements allowed for the development of calibration equations. These data were used to develop calibration curves for DGCI taken indoors ($r^2$=0.65), DGCI taken outdoors ($r^2$=0.83), SPAD ($r^2$=0.57), and leaf nitrogen concentration ($r^2$=0.64). These calibrations equations of the systems and methods disclosed herein provide prediction tools to allow corrective, mid-season nitrogen applications to be made based on an observed value, which allows for the recovery of 90 or 95% of the crop's yield potential.

Crop Management

Commercial corn hybrids (treated with Cruiser Extreme® 250 fungicide and insecticide, genetically modified to express the crylF gene, and resistant to glyphosate, see Table 2 for hybrid information) were planted at eight fields in Arkansas over the course of two (2) years.

Corn was planted at the Arkansas Agricultural Research and Extension Center in Fayetteville, Ariz. Seed was sown at a rate of 74,000 kernels ha$^{-1}$ in a Captina silty loam (fine-silty, siliceous, active, Mesic Typic Fragiudults). Plots consisted of four rows, 101.6 cm apart and 7.6 m in length. Prior to planting, plots received nutrient amendments to meet soil-test recommendations for all nutrients except for nitrogen. Soil nitrogen had been minimized by planting, mowing, and removing at heading a cover crop of rye (*Secale cereale* L.). Numerous soil core samples had been taken throughout the field at depths of 0-15 cm and 15-30 cm, dried, and analyzed using the Mehlich-3 procedure to establish baseline field soil nitrogen levels (Table 2); levels were similar across locations. Irrigation was applied using sprinklers when the soil-moisture deficit reached a deficit maximum of 32 mm as determined by an irrigation scheduling program. The experimental design was a randomized complete block design with four replications.

Field management was similar at other locations and other years (Table 2). At locations other than Fayetteville, potassium, zinc, and sulfur (as potassium sulfate and zinc sulfate) amendments were applied concurrent with the emergence nitrogen application as determined necessary by soil test recommendations. At maturity, the inner 5 m of the middle two rows were harvested by a plot combine. Grain was weighed and moisture content determined, and yield was expressed at a moisture content of 15.5 g 100 g$^{-1}$.

TABLE 2

Production and management information for corn nitrogen-response experiments in 2010 and 2011 at four locations in Arkansas.

| | 2010 | | | |
|---|---|---|---|---|
| Location | Fayetteville | Stuttgart | Marianna | Keiser |
| lat, long | 36.09, −94.17 | 34.46, −91.41 | 34.73, −90.76 | 35.67, −90.08 |
| Hybrid | Pioneer 33D49 | Pioneer 33D49 | Pioneer 31D59 | Pioneer 33D49 |
| Planting Date | 29 April | 22 April | 27 April | 7 May |
| Irrigation Method | sprinkler | furrow | furrow | furrow |
| Row Spacing, cm | 101.6 | 76.2 | 96.5 | 96.5 |
| Plot Length, m | 6.1 | 6.1 | 6.1 | 6.1 |
| Total soil nitrogen, mg kg$^{-1}$ | 714 ± 65 | 744 ± 102 | 688 ± 55 | 759 ± 69 |
| n, plots | 72 | 72 | 72 | 84 |

| | 2011 | | | |
|---|---|---|---|---|
| Location | Fayetteville | Rohwer | Marianna | Keiser |
| lat, long | 36.09, −94.17 | 33.81, −90.76 | 34.73, −90.76 | 35.67, −90.08 |
| Hybrid | Pioneer 1184HR | Pioneer2023HR | Pioneer 31P42 | Pioneer1615HR |
| Planting Date | 6 May | 14 April | 12 May | 12 May |
| Irrigation Method | sprinkler | furrow | furrow | furrow |
| Row Spacing, cm | 91.4 | 96.5 | 96.5 | 96.5 |
| Plot Length, m | 6.1 | 5.8 | 6.1 | 6.1 |

TABLE 2-continued

Production and management information for corn nitrogen-response experiments in 2010 and 2011 at four locations in Arkansas.

| | | | | |
|---|---|---|---|---|
| Total soil nitrogen, mg kg$^{-1}$ | 800 ± 19 | 733 ± 146 | NA‡ | 771 ± 34 |
| n, plots | 84 | 84 | 84 | 84 |

‡Pre-plant soil nitrogen samples were not taken in Marianna in 2011.

Nitrogen Treatments

Nitrogen treatments were applied in two splits at all locations (Table 3). Nitrogen was broadcast to each row by hand. Urea fertilizer (46-0-0) was used for all applications, and in every location, except Fayetteville in 2010, the urea prills were treated with dicyandiamide and nitrogen-(n-butyl) thiophosphotictriamide (Agrotain®, AGROTAIN International, St. Louis, Mo.). Agrotain® was applied to urea prills the subsequent year in Fayetteville due to revised experimental design.

At or near emergence for each location, plots received three nitrogen fertilizer treatments. In the study year 2010, the Stuttgart location was treated at approximately V5 while the Keiser location received treatment at V3. In 2011, Marianna received a similarly late initial treatment at V4. These belated treatments were due to travel delays or field conditions preventing earlier application. One third of the plots received 84 kg ha$^{-1}$ of urea broadcast by hand. One third of the plots received 168 kg ha$^{-1}$ of urea broadcast by hand. The final third of plots received no nitrogen fertilizer. In 2010, when the plots receiving the highest nitrogen rate reached the V6-V10 growth stage, plots from each emergence nitrogen treatment received urea applications of 0, 28, 56, 84, 112 or 168 kg ha$^{-1}$. At Keiser, an additional treatment rate of 224 kg ha$^{-1}$ (2010 and 2011) was applied to ensure that sufficient nitrogen was available to maximize yield and not be immobilized by the clay soil. In 2011, the V6-V10 applications were 0, 14, 18, 70, 112, 168, and 224 kg ha$^{-1}$ (Table 3).

In 2010, urea application in Fayetteville was immediately followed by irrigation. As the other locations received urea plus Agrotain (urease inhibitor), these locations were not irrigated until after a rainfall event had occurred in order to prevent nitrogen movement via furrow flooding; if a rainfall event did not occur within several days of application, irrigation was applied to ensure nutrient availability coincident with target growth stage.

Sampling Methods

Plots were sampled twice during the growing season and once again at harvest. The initial sampling was made when plants in the highest nitrogen-rate plots were rated at the V6-V10 stage. At this point, a corn plant from the center of each of the middle two rows of the plot was selected for sampling and was assumed to be representative of the plot overall. In 2011, following establishment of correct sampling protocols, an additional digital image was taken in situ of the upper portion of plants selected for analysis. These images were later used to make comparisons with images of the same plants taken under controlled lighting conditions. Both excised leaves and plants in the field were photographed against a plywood board that was painted pink (to provide contrast in subsequent image processing) and two internal color standards that were included in each image. These internal color standards were disks colored with a paint of a known DGCI value (0.5722 for green and 0.0733 for yellow). The inclusion of the color standards in each image allowed for corrections of minor vacillations in light and shadow that may occur.

Images were taken at a resolution of 320×240 with a Canon Powershot S5IS Digital Camera (Canon USA, Inc., Lake Success, N.Y.). After images were taken, the uppermost collared leaf of each plant was removed. These leaves were immediately placed in a sealed plastic bag and put on ice. After the entire field had been sampled, an image was made of the selected leaves indoors under fluorescent lighting conditions. Four chlorophyll meter readings were taken from each leaf sampled and then averaged. The leaves were subsequently dried and analyzed for total nitrogen concentration via LECO FP428 nitrogen Analyzer (LECO Corporation, St. Joseph, Mich.) by the Soil Test and Plant Analysis Lab (University of Arkansas, Fayetteville). All sampling was conducted prior to a concurrently scheduled nitrogen fertilizer application.

TABLE 3

Nitrogen treatment information for corn nitrogen-response experiments in 2010 and 2011 at four locations in Arkansas.

| | 2010 | | | |
|---|---|---|---|---|
| Location | Fayetteville | Stuttgart | Marianna | Keiser |
| | Emergence Treatment | | | |
| Rates, kg ha$^{-1}$ | 0, 84, 168 | 0, 84, 168 | 0, 84, 168 | 0, 84, 168 |
| Date | 9 May | 26 May | 28 May | 25 May |
| Stage | V1 | V5 | V1 | V3 |
| | Mid-season Treatment | | | |
| Rates, kg ha$^{-1}$ | 0, 28, 56, 84, 112, 168 | 0, 28, 56, 84, 112, 168 | 0, 28, 56, 84, 112, 168 | 0, 28, 56, 84, 112, 168, 224 |
| Date | 17 June | 18 June | 19 June | 21 June |
| Stage | V7 | V10 | V10 | V7 |
| | 2011 | | | |
| Location | Fayetteville | Rohwer | Marianna | Keiser |
| | Emergence Treatment | | | |
| Rates, kg ha$^{-1}$ | 0, 84, 168 | 0, 84, 168 | 0, 84, 168 | 0, 84, 168 |
| Date | 17 May | 7 May | 27 May | 27 May |
| Stage | V1 | V2 | V4 | V1 |
| | Mid-season Treatment | | | |
| Rates, kg ha$^{-1}$ | 0, 14, 28, 70, 112, 168, 224 | 0, 14, 28, 70, 112, 168, 224 | 0, 14, 28, 70, 112, 168, 224 | 0, 14, 28, 70, 112, 168, 224 |
| Date | 20 June | 7 June | 27 June | 21 June |
| Stage | V6 | V9 | V10 | V6 |

Grain yield was determined by first removing 1 m from each end of the rows within a plot to account for edge effects. The remainder of the interior two rows was then harvested. Moisture was noted and then each sample weight was adjusted for a standard 15.5% moisture content. The result was then multiplied by the two-row harvest area to attain a kg ha$^{-1}$ value for grain yield.

A representative sample of the grain from each plot was ground and analyzed for nitrogen concentration using a LECO FP428 nitrogen Analyzer. The total nitrogen content of the grain was calculated as:

$N$ Content of Grain=Yield×$N$ Concentration of Grain    Equation 7

Grain nitrogen recovery was determined as:

Grain $N$ Recovery=[($N$ Content of Grain–$N$ Content of Grain Receiving no $N$)/$N$ Applied]×100    Equation 8

Post-sampling analysis was conducted on each digital image using SigmaScan Pro 5 (SPSS, 1998, San Jose, Calif.) using the macro described above. Image color thresholds were set at ranges of 30 to 130 for hue and 0 to 100 for saturation. Leaf DGCI values were corrected with comparative color standard values to yield a corrected DGCI value.

Leaf nitrogen concentration, DGCI, and yield values showed no significant differences among different soil types and hybrids; however, relative values were used for pertinent analyses to more fully account for some of the variation that occurred among fields. The relative value for a measurement was obtained by finding the highest value of a particular measurement for a certain location and then dividing all other measurements of a similar type at that location by that value.

Calibration of Nitrogen Response

Figure 18:
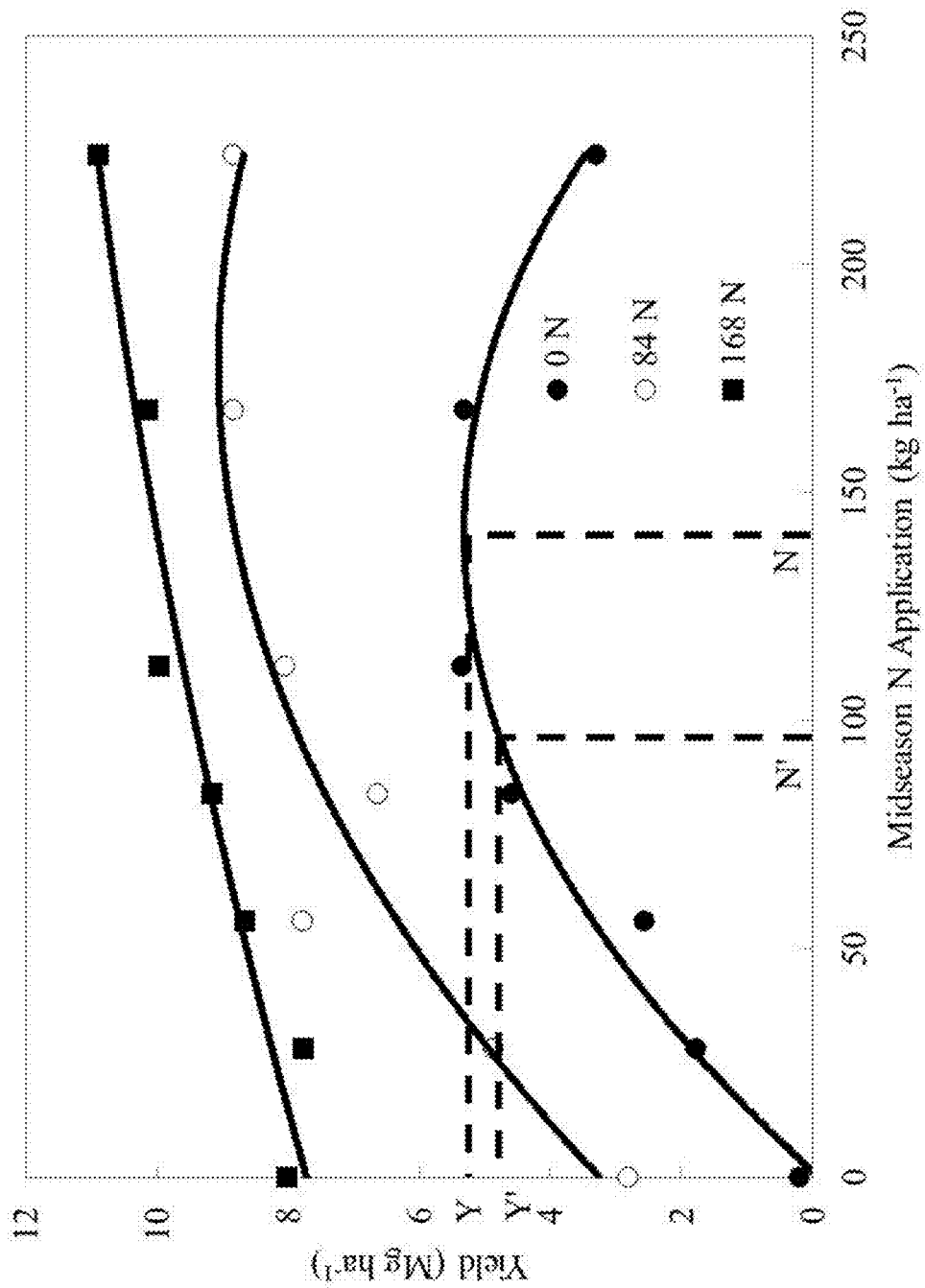
FIG. 18 is a graphical illustration of the yield response to mid-season (V6-V10) nitrogen applications for the three emergence nitrogen application rates during the study year 2010 at the Keiser, Ark. experimental location. Data points represent average values for all replications. The quadratic response for the 0 nitrogen emergence treatment follows the equation $y=-0.27x^2+76.49x-90.86$. Adjusting yield goals from 100% of theoretical maximum yield to 90% of maximum yield would result in a yield loss of 0.53 Mg ha$^{-1}$ (Y–Y') and a reduction in nitrogen rate of 44.5 kg ha$^{-1}$ (nitrogen-nitrogen')

Regression analysis was used to relate grain yield response to nitrogen applied at V6-V10 for each emergence nitrogen rate and at each location and year. Linear and quadratic models were both examined; in almost every instance, the quadratic model was significant and thus they were used for further calculations (Table 4). This was not the case for the 168 kg nitrogen ha$^{-1}$ treatment in Stuttgart in 2010 and Keiser in 2011, which showed no significance fit to either linear or quadratic models. The quadratic model for each location was described by an equation in the form $f(x)=ax^2+bx+c$. By setting the first derivative to zero and solving for x, the amount of nitrogen that need be applied to achieve theoretical maximum yield can be determined for that emergence nitrogen rate, location, and year. In several instances, the calculated amount of nitrogen needed to achieve theoretical maximum yield was greater than that applied in the course of the experiment; in such cases, the maximum amount actually applied was used instead for further calculations. From there, the amount of nitrogen needed to attain 90% and 95% of the theoretical maximum yield was calculated by finding the respective percentages of the determined theoretical maximum yield and solving for x, as illustrated in FIG. 18.

Furthermore, because each plot receiving a mid-season nitrogen application was also sampled for DGCI, SPAD, and leaf nitrogen immediately prior to fertilizing, they represent the current nitrogen status of the corn that gave the particular yield response to the nitrogen application. It can thus be said that applying nitrogen fertilizer in amounts of x (or 0.95x or 0.9x) mid-season to a corn plant having the observed DGCI, SPAD, or leaf nitrogen value would yield the theoretical maximum potential yield (or 95% or 90% of it, respectively). These latter values are of interest, because a relatively small decrease in yield of 5 to 10% requires substantially less nitrogen than that required for maximum yield.

Figure 19:
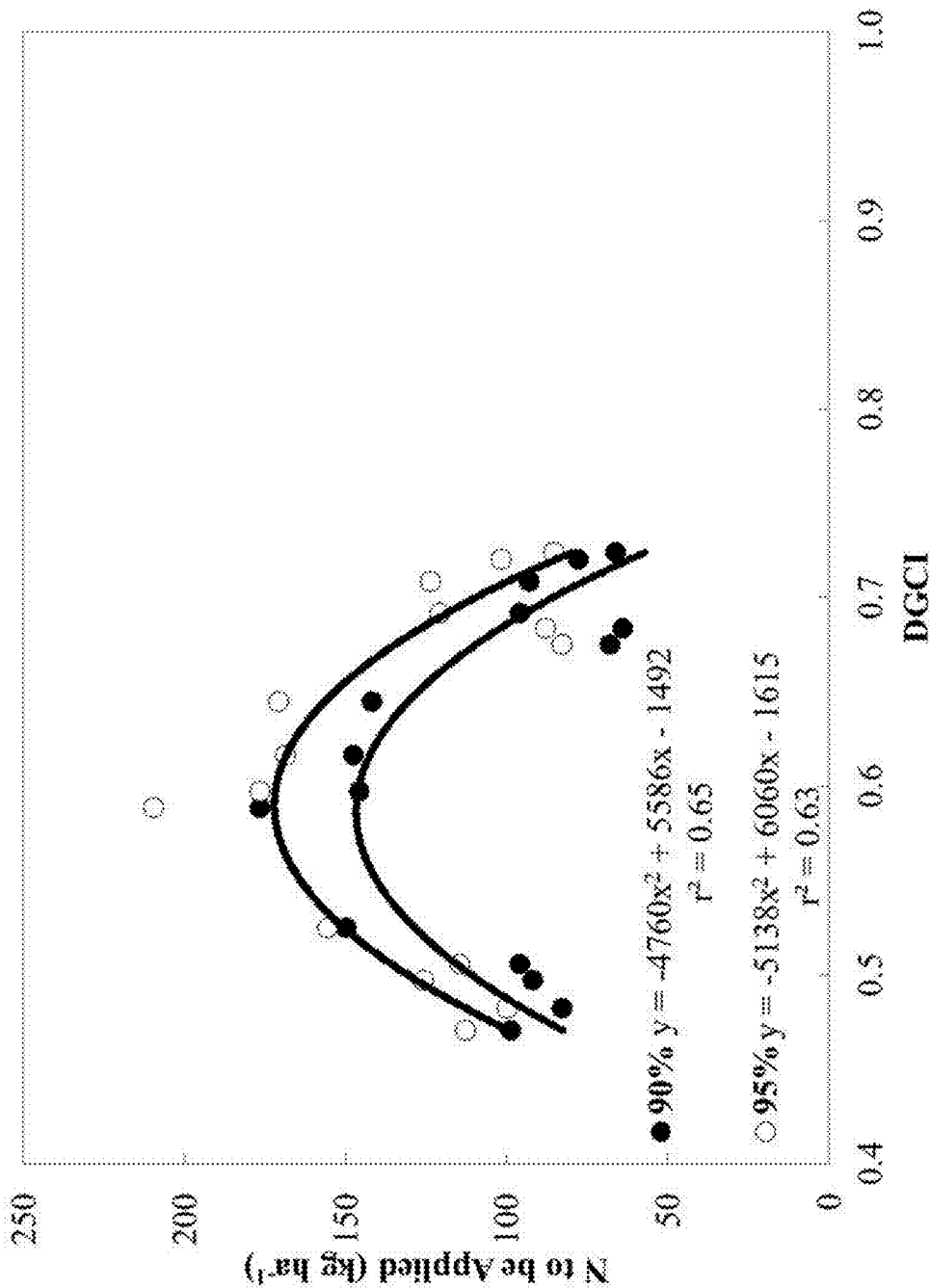
FIG. 19 is a graphical illustration of the calibration curve for the amount of nitrogen to be applied at midseason (V6-V10) to recover 90 or 95% of maximum yield versus dark green color index (DGCI) values measured at V6-V10. The DGCI values were made on the topmost collared leaf and photographed indoors. Data are included from both 2010 and 2011.

The derived data was used to develop a calibration curve where each location and year had three different nitrogen rates applied near emergence. Combining these gives a broad range of mid-season nitrogen conditions, the corresponding DGCI measurements, and the nitrogen needed to attain a given percentage of the theoretical maximum yield. The DGCI measurements and nitrogen needed can be plotted to attain a calibration curve, as illustrated in FIG. 19. Similar calculations were made for creating calibration curves based on SPAD and leaf nitrogen concentration measurements.

TABLE 4

Quadratic equations describing yield response to midseason nitrogen application for all emergence nitrogen rates, locations, and years. The rightmost two columns describe values for each equation maxima.

| Year | Location | Emg N kg ha$^{-1}$ | a | b | c | $r^2$ | Yield at max kg ha$^{-1}$ | N rate at max kg ha$^{-1}$ |
|---|---|---|---|---|---|---|---|---|
| 2010 | Fayetteville | 0 | −0.22 | 68.21 | 2,992 | 0.90 | 8,279 | 155 |
|  |  | 84 | −0.10 | 37.47 | 6,047 | 0.66 | 10,075 | 168‡ |
|  |  | 168 | −0.11 | 33.64 | 7,714 | 0.45 | 10,309 | 154 |
|  | Keiser | 0 | −0.29 | 76.19 | −86 | 0.74 | 5,332 | 142 |
|  |  | 84 | −0.18 | 65.22 | 3,251 | 0.81 | 9,076 | 179 |
|  |  | 168 | −0.02 | 19.38 | 7,721 | 0.37 | 10,941 | 224‡ |
|  | Marianna | 0 | −0.12 | 55.92 | 61 | 0.52 | 5,726 | 168‡ |
|  |  | 84 | −0.14 | 61.47 | 3,554 | 0.66 | 9,714 | 168‡ |
|  |  | 168 | −0.08 | 40.35 | 5,539 | 0.54 | 9,767 | 168‡ |
|  | Stuttgart | 0 | −0.02 | 19.88 | 24 | 0.74 | 2,936 | 168‡ |
|  |  | 84 | −0.15 | 37.49 | 2,367 | 0.45 | 4,476 | 129 |
|  |  | 168† | — | — | — | — | — | — |
| 2011 | Fayetteville | 0 | −0.17 | 72.70 | 426 | 0.91 | 8,386 | 219 |
|  |  | 84 | −0.15 | 53.60 | 5,840 | 0.69 | 10,693 | 181 |
|  |  | 168 | −0.15 | 47.67 | 6,309 | 0.54 | 10,147 | 161 |
|  | Keiser | 0 | −0.18 | 85.16 | 6,585 | 0.82 | 16,770 | 224‡ |
|  |  | 84 | −0.24 | 69.16 | 10,231 | 0.60 | 15,213 | 144 |
|  |  | 168† | — | — | — | — | — | — |
|  | Rohwer | 0 | −0.08 | 45.00 | 1,307 | 0.80 | 7,436 | 224‡ |
|  |  | 84 | −0.07 | 40.41 | 2,803 | 0.81 | 8,629 | 224‡ |
|  |  | 168 | −0.05 | 27.66 | 4,761 | 0.81 | 8,821 | 216 |

†Quadratic responses were significant, except for the 168 kg ha$^{-1}$ emergence rates for Stuttgart in 2010 and Keiser in 2011 ($p < 0.01$). These two locations showed no linear response as well.
‡If calculated nitrogen rate at maximum exceeded the maximum amount of nitrogen applied at midseason (168 kg ha$^{-1}$), the maximum amount applied at midseason was used.

2010 Results

Across all locations, yields were generally highest for corn fertilized with the highest nitrogen rates at emergence and at the subsequent, mid-season date (Table 5). As each emergence nitrogen rate was intended to simulate a relative nitrogen sufficiency or deficiency by the time the crop reached the crucial mid-season stage of nitrogen uptake, varying responses should be expected for each of the three nitrogen levels, as was illustrated by FIG. 18. For almost all of the locations and rates, a quadratic regression response was more appropriate than linear for these data (Table 4) based on p values. This was not the case for the 168 kg ha$^{-1}$ nitrogen rate applied near emergence at Stuttgart, which failed to show a significant linear or quadratic response, and was subsequently disregarded in further calculations. The observed quadratic responses were more pronounced within individual locations for the year, as illustrated in FIG. 18.

The 2010 results led to two suppositions, both supported within the literature (Binder, 2000). Firstly, that perhaps the emergence nitrogen rates that demonstrated the flattest response to mid-season applications may not have received a high enough mid-season rate to produce maximum yield. Secondly, that early season nitrogen availability and uptake will affect potential yield despite mid-season-ameliorating-nitrogen applications, thus resulting in a point at which the application of additional nitrogen units would exhibit a diminishing marginal effect on grain yield.

also shown in Table 5. Grain nitrogen recovery was largely by corn receiving the lowest amounts of nitrogen at emergence and at V6-V10.

Figure 20A:
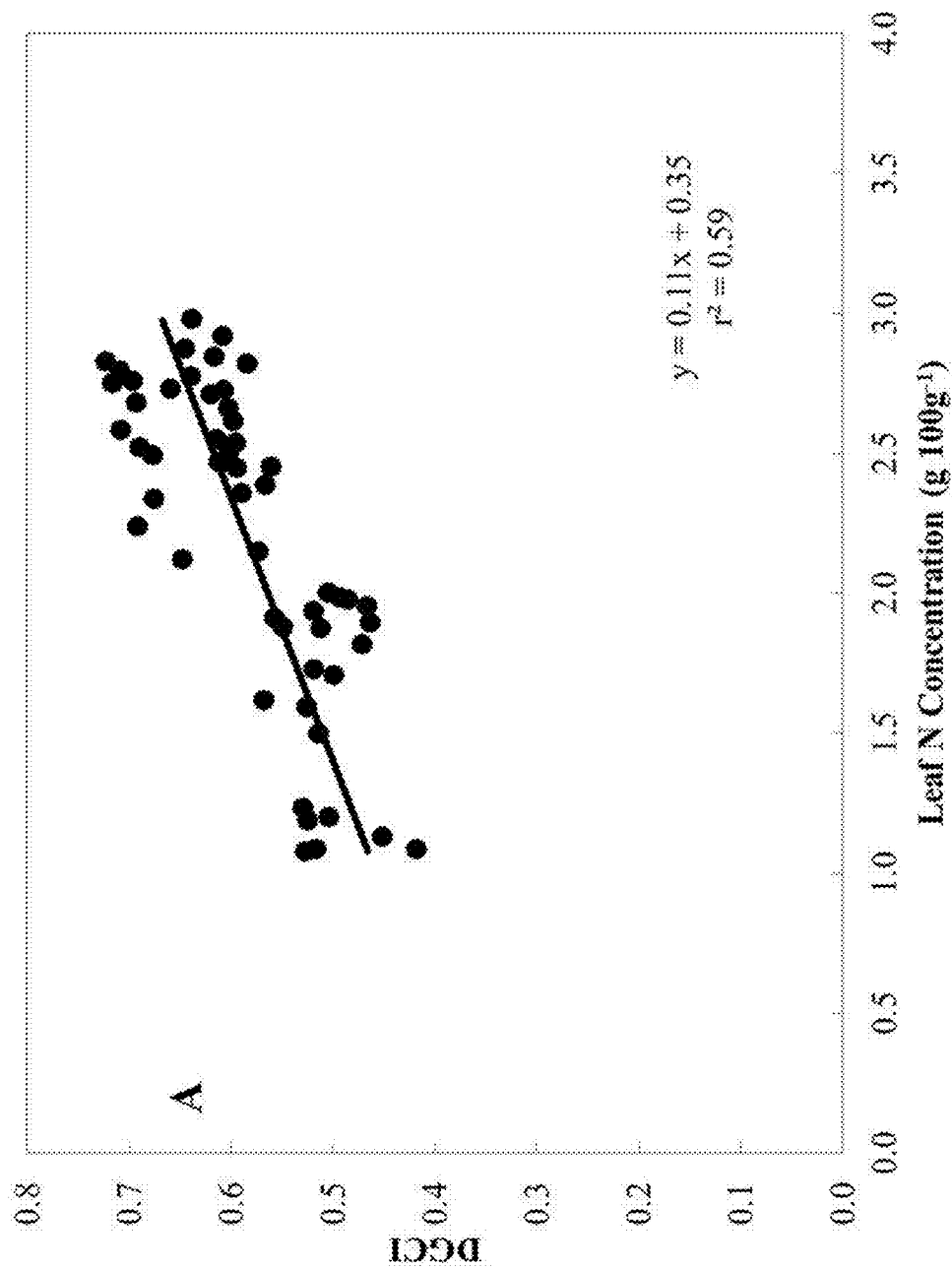
FIGS. 20A and 20B are graphical illustrations of the relationship of DGCI versus leaf nitrogen concentration over the study years 2010 (Fayetteville, Keiser, Marianna) at V6-V10 (FIG. 20A) and 2011 (Fayetteville, Keiser, Rohwer) at V6-V10 (4 rep avgs) (FIG. 20B)
Figure 20B:
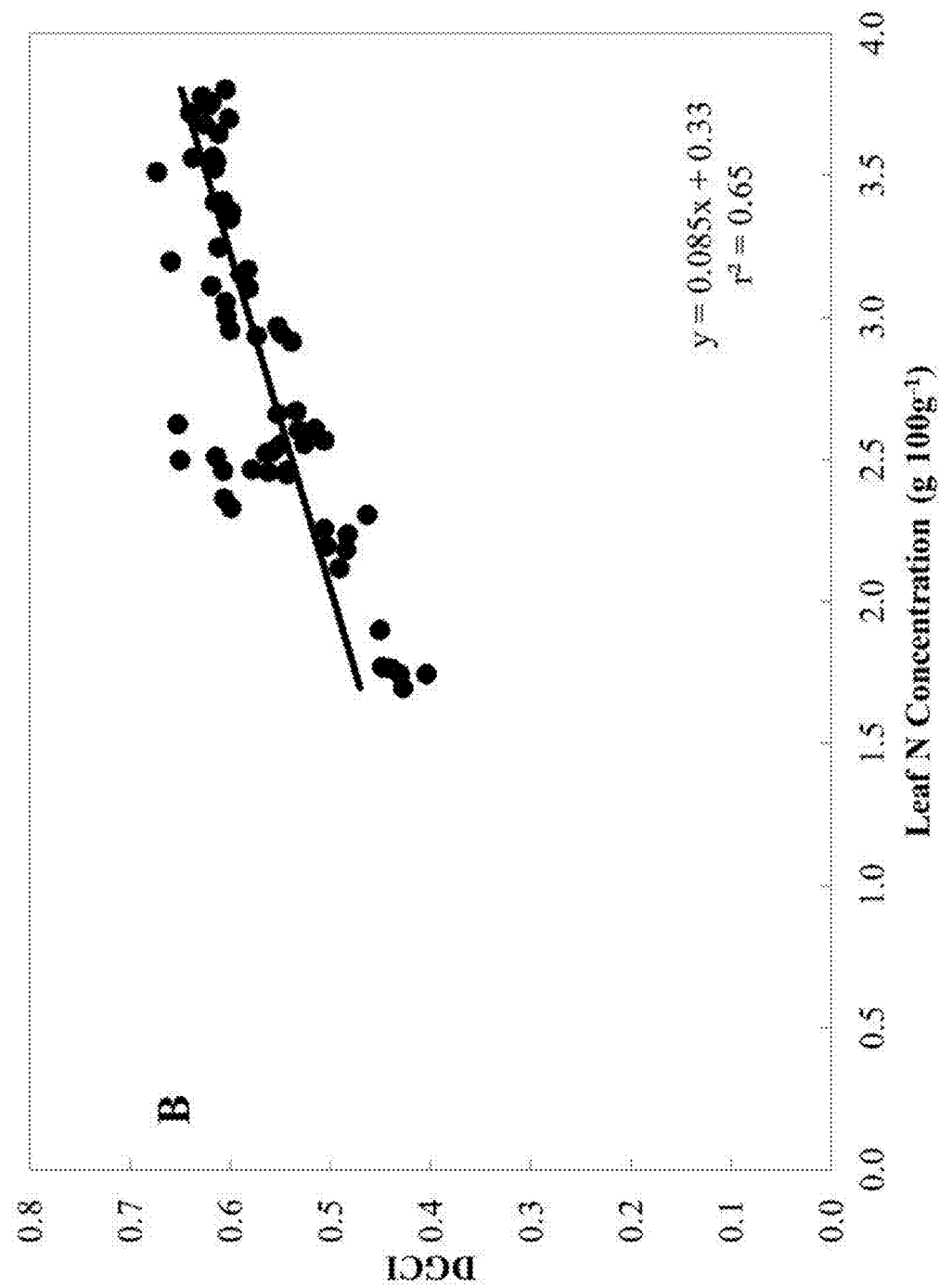

In 2010, DGCI, SPAD and leaf nitrogen concentrations at the V6-V10 stage had a close relationship within all individual locations ($r^2$ values ranging from 0.74 to 0.91) except Keiser. Though a significant relationship ($r^2$=0.87) existed between DGCI and SPAD at Keiser, neither measurement bore any strong relationship to the nitrogen concentration in the leaves sampled on the same date, whereas all other locations over both years demonstrated a relationship of some kind among DGCI, SPAD, and leaf nitrogen concentration (FIGS. 20A and 20B). Based on these anomalies, data relating to leaf nitrogen concentration at Keiser for the first sampling date were removed from further analysis.

2011 Results

A confluence of factors including timing, weather, and weed encroachment resulted in conditions at the Marianna location in 2011 that left the data gathered there unsuitable for further analysis. Spring of 2011 saw massive flooding along the Mississippi river, including the Arkansas Delta. This created a shortage of manpower and access to fields, resulting in an emergence nitrogen application at Marianna occurring at V4, closer to what should have been the second application stage than the first. Subsequent lack of rain or irrigation to incorporate the urea prills may have exacerbated this prob-

TABLE 5

Summary of grain yield and nitrogen recovery for all locations in 2010.

| | | Grain Yield | | | Grain N Recovery | | |
|---|---|---|---|---|---|---|---|
| | V6-V10 | Emergence N Application, kg ha$^{-1}$ | | | | | |
| Location | N App., kg ha$^{-1}$ | 0 | 84 kg ha$^{-1}$ | 168 | 0 | 84 % | 168 |
| Fayetteville | 0 | 2925 g† | 5653 efd | 7949 bc | — | 34 efd | 32 efd |
| | 28 | 4840 f | 7439 cd | 8248 bc | 78 a | 46 becd | 32 ef |
| | 56 | 6145 efd | 8127 bc | 7456 cd | 62 ba | 45 ecd | 25 f |
| | 84 | 7099 ecd | 9566 ba | 9530 ba | 62 ba | 49 bcd | 37 ed |
| | 112 | 7847 bcd | 8232 bc | 10690 a | 58 bc | 35 efd | 35 efd |
| | 168 | 8242 bc | 11048 a | 10103 a | 45 ecd | 45 ecd | 30 ef |
| Marianna | 0 | 3762 fde | 4471 fdec | 4085 fdec | — | 13 dc | 4 dc |
| | 28 | 5809 bdec | 3483 fe | 3755 fde | 116 a | −3 dc | 2 dc |
| | 56 | 6965 bdac | 3926 fdec | 5797 bdec | 93 ba | 9 dc | 17 dc |
| | 84 | 5937 bdec | 1312 f | 4206 fdec | 44 bc | −19 d | 6 dc |
| | 112 | 4981 bdec | 5333 bdec | 7146 bac | 23 dc | 16 dc | 21 dc |
| | 168 | 8089 ba | 9712 a | 5620 bdec | 49 bc | 45 bc | 13 dc |
| Stuttgart | 0 | 114 e | 2567 dc | 4785‡ | — | 27 bac | 35‡ |
| | 28 | 776 e | 5049 ba | 3890‡ | 21 bc | 44 a | 27‡ |
| | 56 | 1163 de | 5240 ba | 5278‡ | 18 bc | 35 ba | 33‡ |
| | 84 | 1147 de | 5649 a | 4870‡ | 12 c | 34 ba | 28‡ |
| | 112 | 3130 c | 5731 a | 3464‡ | 29 bac | 31 ba | 18‡ |
| | 168 | 3654 bc | 6052 a | 5110‡ | 22 bc | 27 bac | 22‡ |
| Keiser | 0 | 223 h | 2837 g | 8029 dc | — | 39 fe | 49 fed |
| | 28 | 1792 hg | 4878 fe | 7783 dc | 75 a | 52 fedc | 48 fed |
| | 56 | 2588 g | 7797 dc | 8680 bc | 57 bdc | 71 bac | 42 fed |
| | 84 | 4595 fe | 6658 de | 9172 bc | 71 ba | 48 fed | 46 fed |
| | 112 | 5367 fe | 8065 dc | 9983 ba | 55 bec | 50 fed | 41 fed |
| | 168 | 5327 fe | 8851 bc | 10164 ba | 42 fed | 47 fed | 41 fed |
| | 224 | 2658 g | 8857 bc | 10915 a | 16 g | 40 fed | 37 f |

†Means with the same letter within a location are not significantly different as determined by an LSD ($p \leq 0.05$).
‡Apparent sampling errors for the 168 kg ha$^{-1}$ rate at Stuttgart led to that data being excluded from analysis of variance. Data is included here for completeness.

These determinations gave rise to several minor changes in the experimental design for the second year of the study, as discussed herein. The purpose of the higher addition of nitrogen fertilizer at V6-V10 was to reach the maxima of the response curve. Grain nitrogen recovery for each location is lem. Additionally, the northern half of the field was heavily infested with pigweed (*Amaranthus palmeri*) which required several applications of herbicide to effectively treat. By the time the field was approached for a mid-season nitrogen application, it was apparent that not only had the initial nitrogen application failed to create any discernible color or height variation among plots, but that it was well past the target V6 application stage. Although the application was made, the field was monitored throughout the rest of the season and determined to be unsuitable for experimental inclusion. As a result, that location was not considered the second year.

Overall, and also within individual locations, the yield responses to mid-season nitrogen applications was slightly different than those of 2010 (Table 6). Those plots that did not receive any nitrogen at emergence showed less curvature in the quadratic response to mid-season applications. This suggests that midseason nitrogen applications to corn with severe early nitrogen deficiencies can have a dramatic effect on yield, and, when compared to the other emergence nitrogen rates for the year, illustrates the effect of emergence nitrogen availability has on midseason nitrogen application response and setting yield potential. The higher two emergence applications demonstrated decidedly more curvature in the quadratic response. The lone exception to this was the plots in Keiser receiving the highest emergence nitrogen rate, which showed neither a linear nor a quadratic response. Moreover, mean comparisons showed a greater range of yields than had been seen in the previous year (Table 6), indicating that the application of additional lower and higher mid-season rates to the experimental design may have had the desired outcome. As in 2010, soil type and corn hybrid seemed to have no significant effect on observations made at the V6-V10 growth stage.

As discussed earlier, the field in Marianna received the first and second nitrogen application much later than would be suitable for the study and was subsequently eliminated from further analysis. The trend of weaker relationships held true when all remaining locations were combined, except for the relationships between DGCI and leaf nitrogen concentration ($r^2$=0.70), which had a greater fit than that of the previous year.

Calibration of Yield Data

For each year, location, and emergence nitrogen rate, the quadratic response of yield to nitrogen applied at V6-V10 is described in Table 4. In all but two instances of ANOVA, the quadratic response was significant at $p<0.001$. At Stuttgart in 2010 and Keiser in 2011, the corn receiving 168 kg nitrogen $ha^{-1}$ at emergence were deemed non-significant for both quadratic and linear regression models.

For the remaining data, the nitrogen rate required to attain a theoretical maximum yield can be found by setting the first derivative to zero and solving for x. That value can, in turn, be substituted for x in the equation and then solved to arrive at the maximum theoretical yield for that particular location and emergence nitrogen rate. These calculated values are presented in the rightmost columns of Table 4. Once maximum theoretical yield has been established, percentages of that figure can be calculated to tailor to an individual yield goal; in the case of this experiment, 90% and 95% of theoretical

TABLE 6

Summary of grain yield and nitrogen recovery for Fayetteville, Rohwer, and Keiser in 2011.

| | | Grain Yield | | | Grain N Recovery | | |
|---|---|---|---|---|---|---|---|
| | V6-V10 | Emergence N Application, kg ha$^{-1}$ | | | | | |
| Location | N App., kg ha$^{-1}$ | 0 | 84 kg ha$^{-1}$ | 168 | 0 | 84 % | 168 |
| Fayetteville | 0 | 1363 d† | 7162 bac | 6289 bc | . | 88 a | 43 bc |
| | 14 | 1958 d | 7011 bac | 6745 bac | 44 bc | 72 ba | 40 bc |
| | 28 | 2375 d | 6767 bac | 7662 bac | 40 bc | 54 bac | 44 bc |
| | 70 | 4998 dc | 8058 ba | 7941 ba | 64 bac | 58 bac | 38 bc |
| | 112 | 6640 bac | 7295 bac | 9343 a | 59 bac | 44 bc | 41 bc |
| | 168 | 7591 bac | 8610 ba | 8878 ba | 52 bac | 42 bc | 36 bc |
| | 224 | 7611 bac | 9276 a | 8220 ba | 41 bc | 35 bc | 26 c |
| Rohwer | 0 | 369 i | 2156 figh | 3134 feg | — | 29 ba | 21 ba |
| | 14 | 850 igh | 2011 igh | 3620 fedc | 21 ba | 9 b | 27 ba |
| | 28 | 451 ih | 2539 figh | 4727 fedc | 12 ba | 23 ba | 22 ba |
| | 70 | 3054 fegh | 3839 fed | 6232 bac | 43 a | 25 ba | 33 ba |
| | 112 | 4761 fedc | 5766 bdc | 4779 bedc | 44 a | 29 ba | 25 ba |
| | 168 | 4295 fedc | 7216 ba | 7528 a | 36 a | 39 a | 33 ba |
| | 224 | 7362 bac | 4824 bdec | 6229 ba | 32 ba | 25 ba | 33 ba |
| Keiser | 0 | — | 4668 c | 85‡ | — | 14 c | 14‡ |
| | 14 | 4672 c | 7996 bac | 15349‡ | 81 a | 56 bac | 72‡ |
| | 28 | 5299 bc | 7928 bac | 16941‡ | 70 ba | 50 bac | 75‡ |
| | 70 | 6447 bac | 9072 ba | 15008‡ | 61 bac | 48 bac | 66‡ |
| | 112 | 6429 bac | 8697 bac | 13533‡ | 45 bac | 40 bac | 49‡ |
| | 168 | 8899 bac | 9866 a | 10830‡ | 50 bac | 40 bc | 55‡ |
| | 224 | 9972 a | 6788 bac | 6781‡ | 45 bac | 19 c | 24‡ |

†Means with the same letter within a location are not significantly different as determined by an LSD ($p \leq 0.05$).
‡Apparent sampling errors for the 168 kg ha$^{-1}$ rate at Keiser led to that data being excluded from analysis of variance. Data is included here for completeness.

Grain nitrogen recovery for each location is shown in Table 7. Grain nitrogen recovery among experimental plots showed less variation compared to the previous year. In 2011, the most efficient plots for both Fayetteville and Rohwer were those that received no nitrogen at emergence and then a mid-level amount at the V6-V10 application.

maximum yield was calculated as an example. These adjusted theoretical yields can then be applied to the quadratic equation for the location rate to determine the amount of nitrogen to be applied to achieve those yields. These calculated yields were then paired with observed DGCI values and used to develop the calibration curve seen in FIG. 19.

FIG. 19 graphically illustrates data taken from photographs made indoors, under controlled lighting conditions, of corn leaf samples taken from the field just prior to the mid-season nitrogen application. Ultimately, the yield data showed strong relationships in the form of the developed calibration curve ($r^2$=0.63 and 0.65 for the 95% and 90% curves, respectively).

Figure 21:
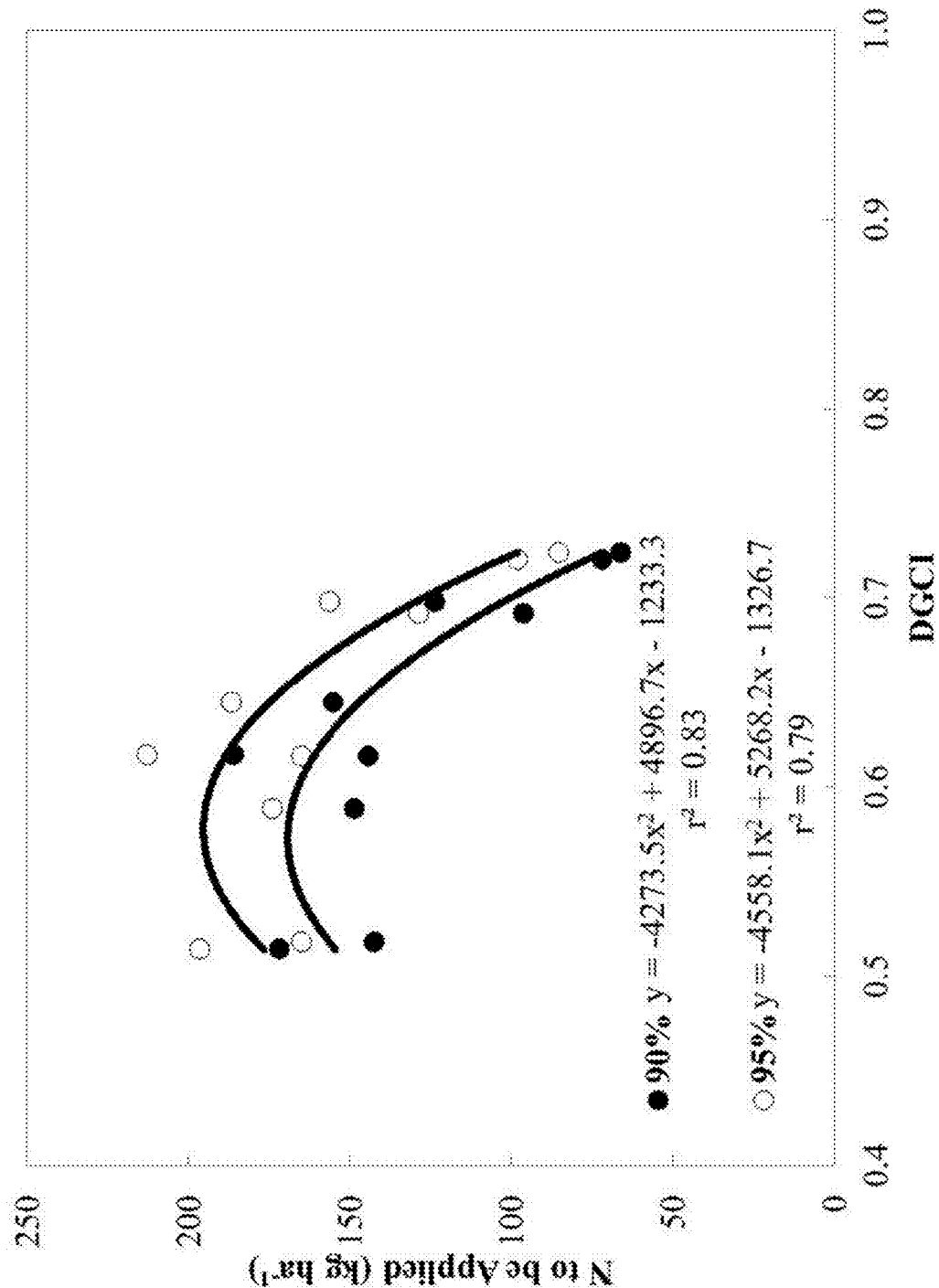
FIG. 21 is a graphical illustration of the calibration curve for the amount of nitrogen to be applied at midseason (V6-V10) to recover 90 and 95% of maximum yield versus dark green color index values measured at V6-V10. DGCI values were made on the upper portion of the plant and photographed outdoors. Data are included from 2011.

DGCI data derived from outdoor photographs in 2011 were used to develop a calibration curve (FIG. 21). Though the range of DGCI values observed in outdoor photographs (0.51-0.72) was slightly narrower than those indoors (0.49-0.73), the range of recommended nitrogen to be applied was generally similar. The outdoor calibration curve showed a closer fit ($r^2$=0.83 and 0.79 for achieving the 95% and 90% yield potential), it resulted in higher recommendations on the lower end of the DGCI range as compared to the indoor photographs.

Figure 22:
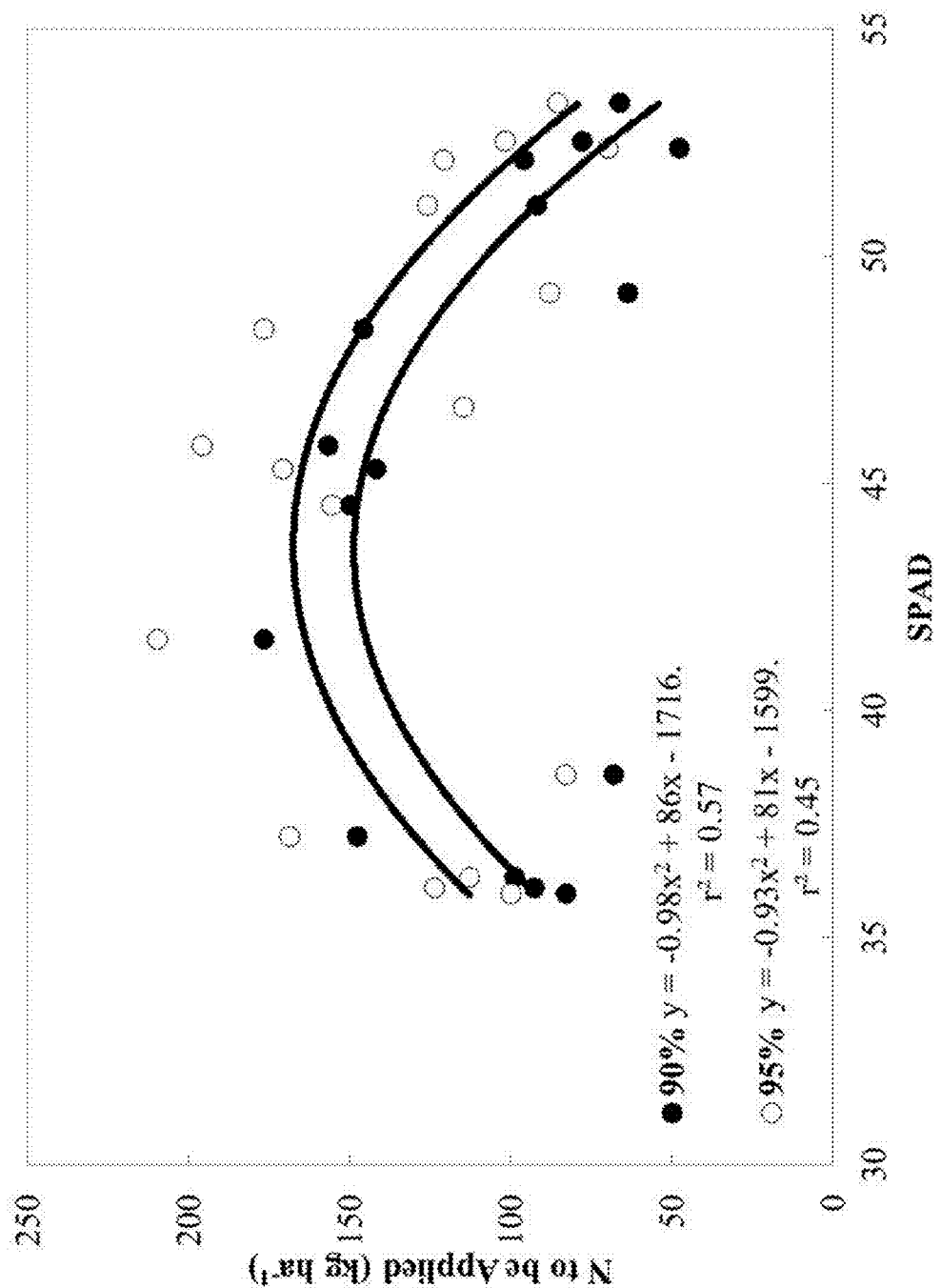
FIG. 22 is a graphical illustration of the SPAD calibration curve developed from the 2010 and 2011 data. Observed SPAD values were used to determine subsequent nitrogen mid-season applications to attain 90 and 95% of theoretical maximum potential yield. This calibration curve is based on SPAD values taken at V6-V10.
Figure 23:
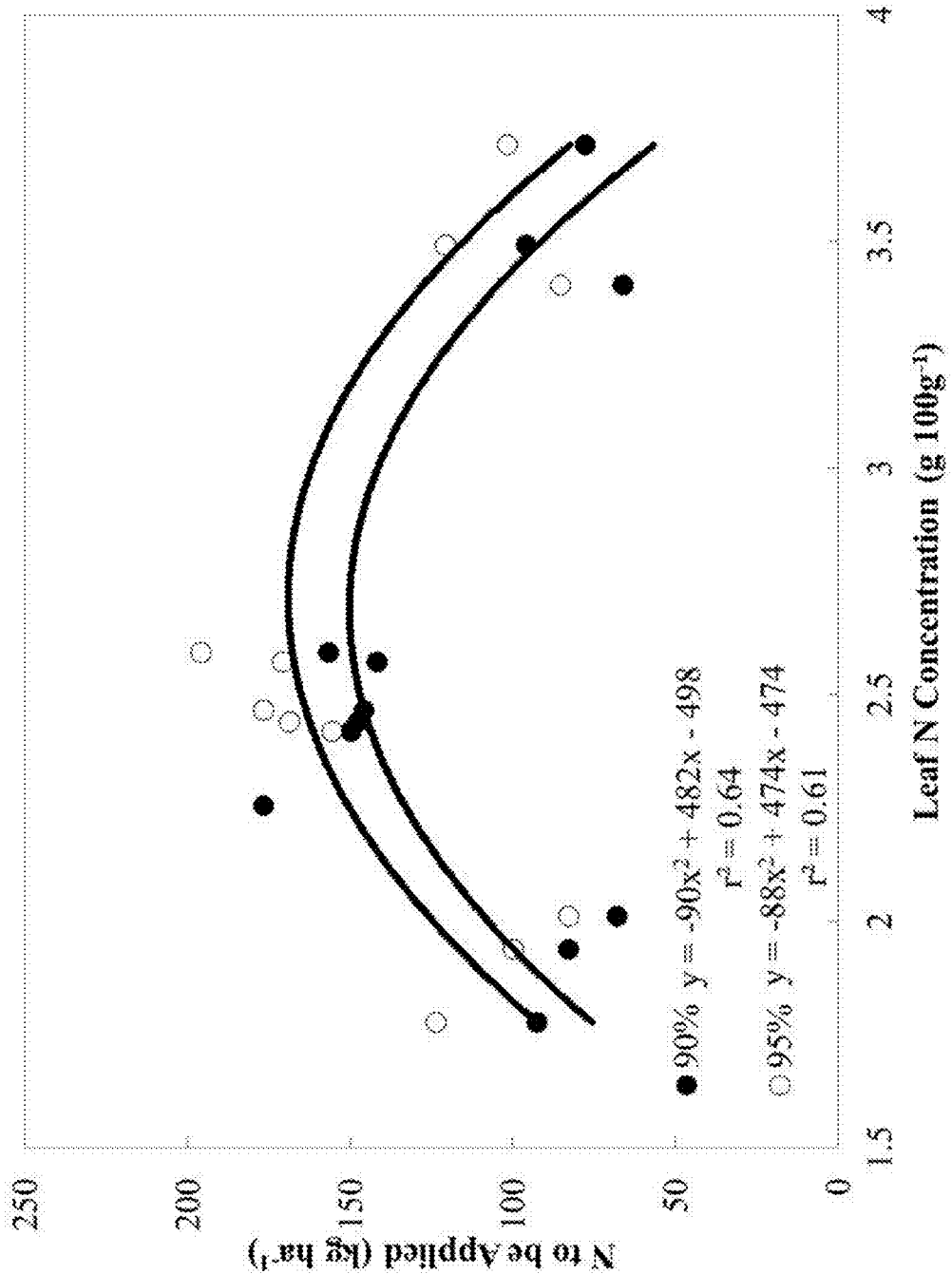
FIG. 23 is a graphical illustration of the leaf nitrogen concentration calibration curve developed from 2010 and 2011 data. Observed leaf nitrogen concentration measurements were used to determine subsequent nitrogen mid-season applications to attain 90 and 95% of theoretical maximum potential yield. This calibration curve includes data from both years of the study and is based on leaf samples taken at V6-V10. Partial data loss of leaf nitrogen samples in Marianna in 2010 account for the lower number of data points compared to the other two calibration curves.

SPAD (FIG. 22) and leaf nitrogen concentration (FIG. 23) calibration curves are presented for comparison. The SPAD calibration curve had the least goodness of fit compared to leaf nitrogen concentration and DGCI, though it ultimately recommended similar nitrogen rate applications (75 to 160 kg ha$^{-1}$) to achieve target yields across a range of mid-season nitrogen crop statuses. The leaf nitrogen concentration calibration curve bore the strongest resemblance to the DGCI curve, with equivalent $r^2$ values for the 95% curves and a deviation of 0.09 between the $r^2$ values of the 90% curve. The recommended range to attain a maximum yield was similar, between 60-160 kg ha$^{-1}$.

Figure 24A:
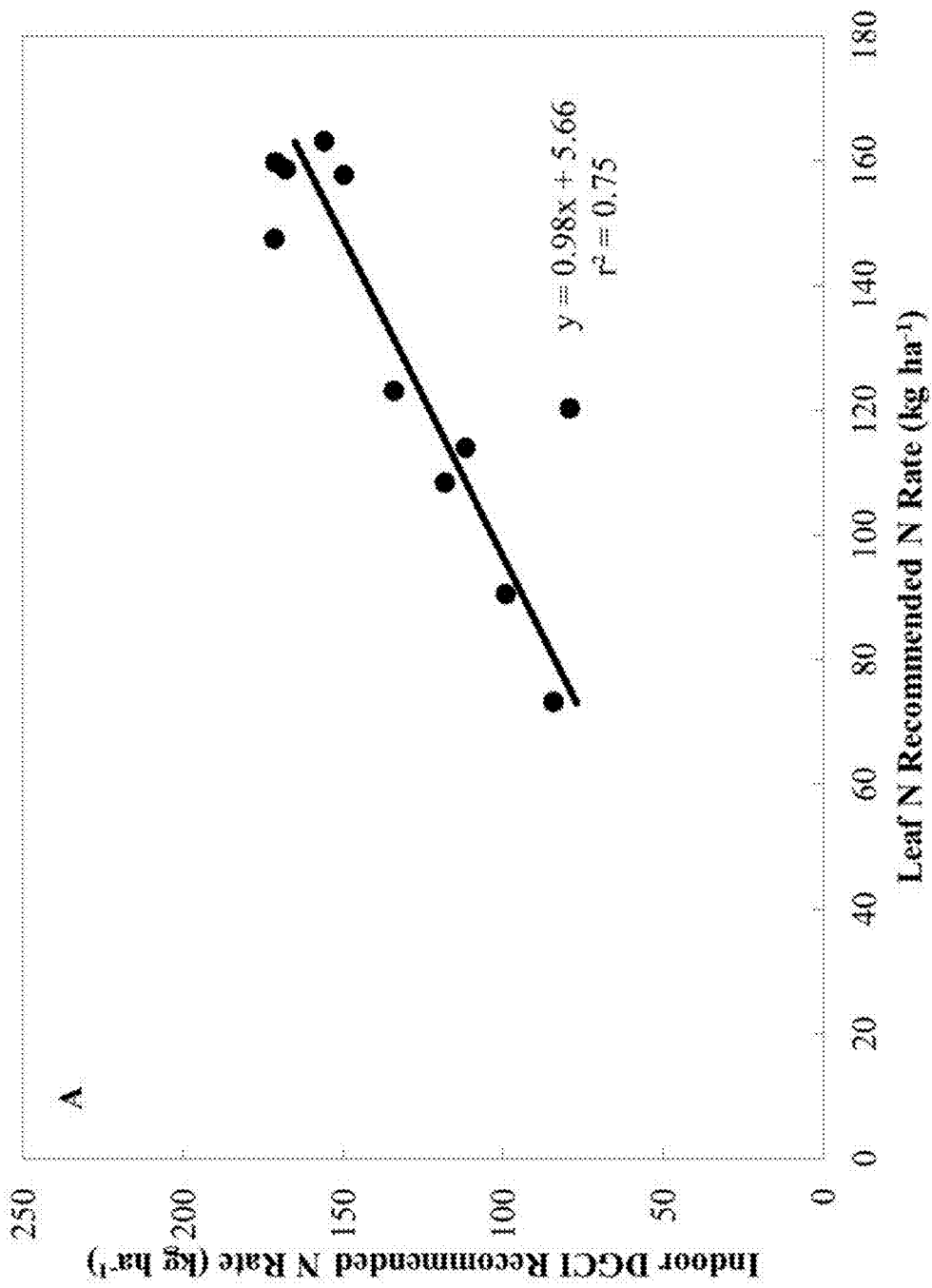
FIGS. 24A and 24B are graphical illustrations of the relationships between nitrogen application recommendations made by the calibration curves (90% maximum yield) of indoor DGCI (FIG. 24A) and outdoor DGCI (FIG. 24B) with leaf nitrogen concentration.
Figure 24B:
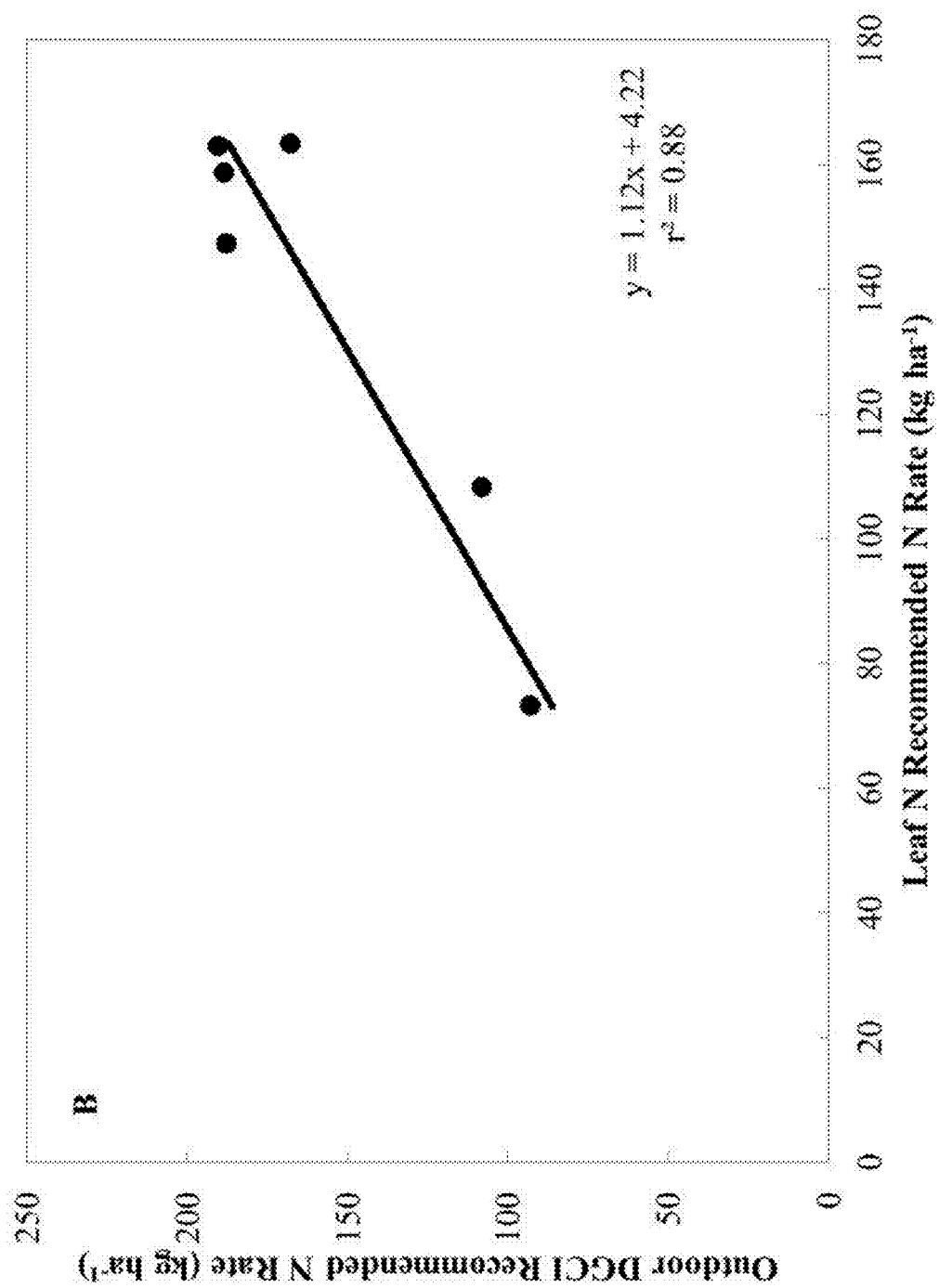

Relationships between the nitrogen recommendations made by the various calibration curves showed high $r^2$ values among DGCI and leaf nitrogen concentration, with no significant relationship discernible between SPAD and leaf nitrogen concentration. FIGS. 24A and 24B illustrate the DGCI and leaf nitrogen concentration relationships, with an $r^2$ value of 0.75 and 0.88 for the measurements taken indoor and outdoor, respectively. The outdoor chart has fewer data points, as matching sets needed for comparison were not as complete as with the indoor sets. The slope of both graphs (0.98 and 1.12 for indoor and outdoor), which demonstrates the similarities between the level of recommendations for the DGCI method compared with those derived from leaf nitrogen concentration analysis.

In summation, the relationship between the DGCI method, SPAD values, and leaf nitrogen analysis was strong at the V6-V10 stage. The DGCI was closely associated with leaf nitrogen concentration at the V6-V10 stages in both years ($r^2$ of 0.45 in 2010 and 0.70 in 2011). The diagnosis and treatment of nitrogen deficient corn at an early stage can prevent yield loss by corrective nitrogen fertilization or prevent over-application of nitrogen fertilizer. The SPAD and DGCI were closely associated with respect to each location and each year.

There was a marked increase in yield as the levels of emergence nitrogen rate increased indicating that early season nitrogen deficits reduced corn grain yield potential for the season, despite any amount of remedial nitrogen fertilizer that was applied as a corrective measure mid-season.

The shape of the quadratic response and the effect that the changes in the experimental design had on the response between the two years suggest that, while yield responses to mid-season nitrogen applications may initially appear to have only slightly quadratic characteristics, this only occurs at lower rates. Sufficiently high nitrogen rates will demonstrate the overall quadratic nature of the response in corn. The quadratic model of the systems and methods disclosed herein can indeed result in increasingly higher rates, which eventually lead to reduced yields due to over-application. From a practical standpoint, the maxima in the quadratic response curves indicate the very limit of economic return on further nitrogen applications for the producer. Indeed, the maximum net profit will most likely occur for a producer at a point below the nitrogen rate required to attain 100% of the maximum potential yield. The economics depend on trends in nitrogen fertilizer prices, corn prices, other variables and fixed costs. The calibration curve of the systems and methods disclosed herein make these adjustments possible in real-time.

Whereas, the systems and methods have been described in relation to the drawings and claims, it should be understood that other and further modifications, apart from those shown or suggested herein, may be made within the spirit and scope of this invention.

What is claimed is:

1. A computer-implemented method of determining an in-season nitrogen fertilization rate for a non-legume crop using digital image analysis, said method comprising the steps of:
   a. receiving a dark green color index obtained from analysis of a digital image of said crop, where said dark green color index is equal to DGCI=[(H−60)/60+(1−S)+(1−B)]/3, where DGCI is equal to said dark green color index, H is equal to an average hue value, S is equal to an average saturation value, and B is equal to an average brightness value;
   b. determining a corrected dark green color index from said dark green color index;
   c. determining said nitrogen fertilization rate from said corrected dark green color index; and
   d. providing said nitrogen fertilization rate to achieve a predetermined yield potential for said crop.

2. The method of claim 1 further comprising the steps of:
   a. acquiring said image of a colored leaf from said crop of non-legume plants, said image comprising a comparative standard to account for differences in cameras or lighting conditions or both, said image further comprising a contrasting standard having a color in a portion of the visible spectrum away from the visible spectrum of the color of said leaf; and
   b. performing an algorithm to determine said dark green color index of said leaf in said image.

3. The method of claim 2 further comprising the step of placing said comparative standard a distance away from said crop to minimize any shadows between said crop and said comparative standard.

4. The method of claim 2 wherein said comparative standard is a plurality of standardized color disks having a predetermined shape and a color representing a color value ranging from severely nitrogen deficient to nitrogen sufficient of said crop.

5. The method of claim 4 wherein said standardized color disks further comprise a first standardized color disk having a yellow color representing a severely nitrogen deficient leaf and a second standardized disk having a dark green color representing a nitrogen sufficient leaf.

6. The method of claim 4 wherein said algorithm recognizes said shape of said standardized color disks and uses said standardized color disks as said comparative standard to adjust for different cameras or lighting conditions or both.

7. The method of claim 2 wherein said color of said contrasting standard is pink.

8. The method of claim 2 wherein said algorithm further comprises the steps of:
   a. calculating said dark green color index of said leaf in said image;

b. calculating said dark green color index of said comparative standard in said image; and
c. calculating said corrected dark green color index from said dark green color index of said leaf and said dark green color index of said comparative standard.

9. The method of claim 8 wherein said step of calculating said dark green color index of said leaf in said image further comprises the steps of:
   a. obtaining absolute red, green and blue values of said leaf in said image;
   b. converting said absolute red, green and blue values to percentage red, green and blue values of said leaf in said image;
   c. converting said percentage red, green and blue values to absolute hue, saturation and brightness values of said leaf in said image;
   d. calculating said average hue, saturation and brightness values from said absolute hue, saturation and brightness values of said leaf in said image; and
   e. converting said average hue, saturation and brightness values to said dark green color index of said leaf in said image.

10. The method of claim 9 wherein said dark green color index of said leaf in said image encompasses a dark green color on a scale of zero (0) to one (1) with values closer to one (1) representing a darker green.

11. The method of claim 8 wherein said step of calculating said dark green color index of said comparative standard in said image further comprises the steps of:
   a. obtaining absolute red, green and blue values of said comparative standard in said image;
   b. converting said absolute red, green and blue values to percentage red, green and blue values of said comparative standard in said image;
   c. converting said percentage red, green and blue values to absolute hue, saturation and brightness values of said comparative standard in said image;
   d. calculating said average hue, saturation and brightness values from said absolute hue, saturation and brightness values of said comparative standard in said image; and
   e. converting said average hue, saturation and brightness values to said dark green color index of said comparative standard in said image.

12. The method of claim 11 wherein said dark green color index of said comparative standard in said image encompasses a dark green color on a scale of zero (0) to one (1) with values closer to one (1) representing a darker green.

13. The method of claim 1 further comprising the step of determining nitrogen sufficiency or deficiency of said leaf in said image from said dark green color index.

14. The method of claim 13 wherein said leaf in said image is a corn leaf at tasseling.

15. The method of claim 13 further comprising transmitting said leaf nitrogen sufficiency or deficiency through a network connection.

16. The method of claim 13 further comprising the step of estimating yield of said crop from said image based on said leaf nitrogen sufficiency or deficiency.

17. The method of claim 16 wherein said crop is corn at V6 through V10 development stage.

18. The method of claim 1 wherein said non-legume plant is selected from the group consisting of corn, wheat, rice, cotton, potatoes sugarcane, turfgrass or forage grass species.

19. The method of claim 1 further comprising the step of estimating potential yield of said crop from said image as a function of said dark green color index.

20. The method of claim 1 further comprising the step of transmitting said dark green color index through a network connection.

21. The method of claim 1 further comprising the step of transmitting said nitrogen fertilization rate through a network connection.

22. The method of claim 1 further comprising the step of providing a recommended amount of nitrogen per unit area to be applied at in-season based on said nitrogen fertilization rate in order to maximize said predetermined yield potential for said crop.

23. The method of claim 1 further comprising the step of providing a recommended amount of nitrogen per unit area to be applied during mid-season at V6 through V10 development stage in order to maximize said predetermined yield potential for a corn crop based on said nitrogen fertilization rate.

24. The method of claim 1 wherein said step of determining said nitrogen fertilization rate further comprises the step of providing a mathematical model forming a yield potential response curve as a function of said nitrogen fertilization rate.

25. The method of claim 24 wherein said model of said yield potential response curve is a quadratic expression.

26. The method of claim 25 wherein said quadratic expression is a function of $f(x)=ax^2+bx+c$, where $f(x)$ is equal to said predetermined yield potential, x is equal to said nitrogen fertilization rate, a is equal to a quadratic coefficient to said nitrogen fertilization rate, b is equal to a linear coefficient to said nitrogen fertilization rate, and c is equal to said predetermined yield potential when said nitrogen fertilization rate is equal to 0.

27. The method of claim 1 wherein said step of determining said nitrogen fertilization rate further comprises the step of performing an algorithm providing said nitrogen fertilization rate as a function of said dark green color index.

28. The method of claim 27 wherein said algorithm is a quadratic relationship of said nitrogen fertilization rate with respect to said dark green color index.

29. A system, comprising:
   a portable electronic device comprising a camera for taking a digital image of a vegetative plant; and
   a processor in communication with said portable electronic device, said processor operable for calculating a nitrogen fertilization rate to achieve a predetermined yield potential for said plant as a function of a corrected dark green color index of said image, where said function is in the form of $f(x)=ax^2+bx+c$, where $f(x)$ is equal to said predetermined yield potential, x is equal to said nitrogen fertilization rate, a is equal to a quadratic coefficient to said nitrogen fertilization rate, b is equal to a linear coefficient to said nitrogen fertilization rate, and c is equal to said predetermined yield potential when said nitrogen fertilization rate is equal to 0.

30. The system of claim 29 further comprising a memory accessible by said processor for storing corrected dark green color indexes.

31. The system of claim 29 further comprising an application program loaded on said portable electronic device.

32. The system of claim 29 further comprising a central processing unit communicably attached to said electronic device via a network connection for performing an algorithm to estimate said nitrogen fertilization rate based on said corrected dark green color index.

33. The system of claim 29 further comprising a comparative standard to account for differences in cameras or lighting conditions or both and a contrasting standard having a color in a portion of the visible spectrum away from the visible spectrum of the color of said plant.

34. The system of claim 33 wherein said comparative standard has a predetermined shape and a color representing a color value ranging from severely nitrogen deficient to nitrogen sufficient of said plant.

35. The system of claim 34 wherein said comparative standard further comprises a first comparative standard having a yellow color representing a severely nitrogen deficient leaf and a second comparative standard having a dark green color representing a nitrogen sufficient leaf.

36. A process for providing an in-season nitrogen fertilization rate, said process comprising the steps of:
   a. receiving a corrected dark green color index of a digital image of a crop;
   b. determining said nitrogen fertilization rate for said crop from said corrected dark green color index of said image using a quadratic function in the form of $f(x)=ax^2+bx+c$, where $f(x)$ is equal to said predetermined yield potential, x is equal to said nitrogen fertilization rate, a is equal to a quadratic coefficient to said nitrogen fertilization rate, b is equal to a linear coefficient to said nitrogen fertilization rate, and c is equal to said predetermined yield potential when said nitrogen fertilization rate is equal to 0; and
   c. providing said nitrogen fertilization rate to achieve said predetermined yield potential for said crop.

37. The process of claim 36 further comprising the step of acquiring said digital image of a colored leaf from said crop, a comparative standard to account for differences in cameras or lighting conditions or both, and a contrasting standard having a color in a portion of the visible spectrum away from the visible spectrum of the color of said leaf.

38. The process of claim 37 wherein said comparative standard is a plurality of standardized color disks having a predetermined shape and a color representing a color value ranging from severely nitrogen deficient to nitrogen sufficient of said crop.

39. The process of claim 38 wherein said standardized color disks further comprise a first standardized color disk having a yellow color representing a severely nitrogen deficient leaf and a second standardized disk having a dark green color representing a nitrogen sufficient leaf.

40. The process of claim 37 wherein said color of said contrasting standard is pink.

41. The process of claim 37 further comprising the steps of:
   a. calculating a dark green color index of said leaf in said image;
   b. calculating a dark green color index of said comparative standard in said image; and
   c. calculating said corrected dark green color index from said dark green color index of said leaf and said dark green color index of said comparative standard.

42. The process of claim 41 wherein said step of calculating said dark green color index of said leaf in said image and/or said step of calculating said dark green color index of said comparative standard in said image further comprises the steps of:
   a. obtaining absolute red, green and blue values in said image;
   b. converting said absolute red, green and blue values to percentage red, green and blue values in said image;
   c. converting said percentage red, green and blue values to absolute hue, saturation and brightness values in said image;
   d. calculating average hue, saturation and brightness values from said absolute hue, saturation and brightness values in said image; and
   e. converting said average hue, saturation and brightness values to said dark green color index in said image.

43. The process of claim 42 further comprising converting said average hue, saturation and brightness values to said dark green color index in said image using the following equation:

$$DGCI=[(H-60)/60+(1-S)+(1-B)]/3$$

where DGCI is equal to dark green color index, H is equal to said average hue value, S is equal to said average saturation value, and B is equal to said average brightness value.

44. The process of claim 43 wherein said dark green color index in said image encompasses a dark green color on a scale of zero (0) to one (1) with values closer to one (1) representing a darker green.

45. The process of claim 37 further comprising the step of determining nitrogen sufficiency or deficiency of said leaf in said image from said dark green color index.

46. The process of claim 45 further comprising the step of estimating potential yield of said crop from said image based on said leaf nitrogen sufficiency or deficiency.

* * * * *